United States Patent
Abraham

(10) Patent No.: US 8,119,128 B2
(45) Date of Patent: Feb. 21, 2012

(54) ANTIBODIES THAT BIND UROKINASE-TYPE PLASMINOGEN ACTIVATOR AND EPITOPES THEREFOR

(75) Inventor: Edward Abraham, Denver, CO (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 618 days.

(21) Appl. No.: 11/718,094

(22) PCT Filed: Oct. 28, 2005

(86) PCT No.: PCT/US2005/039108
§ 371 (c)(1), (2), (4) Date: Apr. 26, 2007

(87) PCT Pub. No.: WO2006/050177
PCT Pub. Date: May 11, 2006

(65) Prior Publication Data
US 2009/0232799 A1    Sep. 17, 2009

Related U.S. Application Data

(60) Provisional application No. 60/623,188, filed on Oct. 29, 2004.

(51) Int. Cl.
*A61K 39/00* (2006.01)
(52) U.S. Cl. .................................. 424/130.1; 424/133.1
(58) Field of Classification Search .......................... None
See application file for complete search history.

(56) References Cited

U.S. PATENT DOCUMENTS

| | | | |
|---|---|---|---|
| 6,488,927 B2 | 12/2002 | Muzykantov et al. | |
| 6,750,201 B1 | 6/2004 | Cines et al. | |
| 6,833,357 B2 * | 12/2004 | Cines et al. | 514/12.1 |
| 7,041,287 B2 | 5/2006 | Muzykantov et al. | |
| 7,172,760 B2 | 2/2007 | Muzykantov et al. | |
| 2002/0131964 A1 | 9/2002 | Cines et al. | |
| 2003/0152563 A1 | 8/2003 | Muzykantov et al. | |
| 2004/0126885 A1 | 7/2004 | Cines et al. | |
| 2004/0254115 A1 | 12/2004 | Cines et al. | |
| 2005/0158300 A1 | 7/2005 | Cines et al. | |
| 2007/0031392 A1 | 2/2007 | Cines et al. | |

OTHER PUBLICATIONS

Ossowski et al., Cancer Research, 1991, vol. 51, p. 274-281.*
Kipriyanov et al. Molecular Biotechnology, vol. 12, p. 173-201, 1999.*
International Search Report and Written Opinion for Application No. PCT/US05/39108 of the Regents of the University of Colorado, mailed Jun. 12, 2007.
Campbell, "Monoclonal antibody technology;" vol. 13 of Laboratory Techniques in Biochemistry and Molecular Biology, Elsevier Science Publishers B.V., Amsterdam, 1984, pp. 1-32.

* cited by examiner

*Primary Examiner* — Yunsoo Kim
(74) *Attorney, Agent, or Firm* — Faegre Baker Daniels LLP

(57) ABSTRACT

Anti-uPA antibodies and antigen-binding regions thereof, as well as pharmaceutical compositions comprising such antibodies and antigen-binding regions, are described. Also described are methods of using such antibodies and antigen-binding regions to bind uPA epitopes and activate uPA function, such as inhibition of uPA mediated inflammation. Epitopes that can be used to activate uPA function and anti-inflammation activity are also described, as well as methods of identifying compounds that can bind them.

10 Claims, 7 Drawing Sheets

SEQUENCE LISTING

<160> NUMBER OF SEQ ID NOS: 18

<210> SEQ ID NO 1
<211> LENGTH: 431
<212> TYPE: PRT
<213> ORGANISM: Homo sapiens

<400> SEQUENCE: 1

```
Met Arg Ala Leu Leu Ala Arg Leu Leu Leu Cys Val Leu Val Val Ser
1               5                   10                  15

Asp Ser Lys Gly Ser Asn Glu Leu His Gln Val Pro Ser Asn Cys Asp
            20                  25                  30

Cys Leu Asn Gly Gly Thr Cys Val Ser Asn Lys Tyr Phe Ser Asn Ile
        35                  40                  45

His Trp Cys Asn Cys Pro Lys Lys Phe Gly Gly Gln His Cys Glu Ile
    50                  55                  60

Asp Lys Ser Lys Thr Cys Tyr Glu Gly Asn Gly His Phe Tyr Arg Gly
65                  70                  75                  80

Lys Ala Ser Thr Asp Thr Met Gly Arg Pro Cys Leu Pro Trp Asn Ser
                85                  90                  95

Ala Thr Val Leu Gln Gln Thr Tyr His Ala His Arg Ser Asp Ala Leu
            100                 105                 110

Gln Leu Gly Leu Gly Lys His Asn Tyr Cys Arg Asn Pro Asp Asn Arg
        115                 120                 125
```

```
Arg Arg Pro Trp Cys Tyr Val Gln Val Gly Leu Lys Pro Leu Val Gln
130                 135                 140

Glu Cys Met Val His Asp Cys Ala Asp Gly Lys Lys Pro Ser Ser Pro
145                 150                 155                 160

Pro Glu Glu Leu Lys Phe Gln Cys Gly Gln Lys Thr Leu Arg Pro Arg
                165                 170                 175

Phe Lys Ile Ile Gly Gly Glu Phe Thr Thr Ile Glu Asn Gln Pro Trp
            180                 185                 190

Phe Ala Ala Ile Tyr Arg Arg His Arg Gly Gly Ser Val Thr Tyr Val
        195                 200                 205

Cys Gly Gly Ser Leu Met Ser Pro Cys Trp Val Ile Ser Ala Thr His
210                 215                 220

Cys Phe Ile Asp Tyr Pro Lys Lys Glu Asp Tyr Ile Val Tyr Leu Gly
225                 230                 235                 240

Arg Ser Arg Leu Asn Ser Asn Thr Gln Gly Glu Met Lys Phe Glu Val
                245                 250                 255

Glu Asn Leu Ile Leu His Lys Asp Tyr Ser Ala Asp Thr Leu Ala His
            260                 265                 270

His Asn Asp Ile Ala Leu Leu Lys Ile Arg Ser Lys Glu Gly Arg Cys
        275                 280                 285

Ala Gln Pro Ser Arg Thr Ile Gln Thr Ile Cys Leu Pro Ser Met Tyr
290                 295                 300

Asn Asp Pro Gln Phe Gly Thr Ser Cys Glu Ile Thr Gly Phe Gly Lys
305                 310                 315                 320

Glu Asn Ser Thr Asp Tyr Leu Tyr Pro Glu Gln Leu Lys Met Thr Val
                325                 330                 335

Val Lys Leu Ile Ser His Arg Glu Cys Gln Gln Pro His Tyr Tyr Gly
            340                 345                 350

Ser Glu Val Thr Thr Lys Met Leu Cys Ala Ala Asp Pro Gln Trp Lys
        355                 360                 365

Thr Asp Ser Cys Gln Gly Asp Ser Gly Gly Pro Leu Val Cys Ser Leu
370                 375                 380

Gln Gly Arg Met Thr Leu Thr Gly Ile Val Ser Trp Gly Arg Gly Cys
385                 390                 395                 400

Ala Leu Lys Asp Lys Pro Gly Val Tyr Thr Arg Val Ser His Phe Leu
                405                 410                 415

Pro Trp Ile Arg Ser His Thr Lys Glu Glu Asn Gly Leu Ala Leu
            420                 425                 430

<210> SEQ ID NO 2
<211> LENGTH: 86
<212> TYPE: PRT
<213> ORGANISM: Homo sapiens

<400> SEQUENCE: 2

Ser Lys Thr Cys Tyr Glu Gly Asn Gly His Phe Tyr Arg Gly Lys Ala
1               5                   10                  15

Ser Thr Asp Thr Met Gly Arg Pro Cys Leu Pro Trp Asn Ser Ala Thr
                20                  25                  30

Val Leu Gln Gln Thr Tyr His Ala His Arg Ser Asp Ala Leu Gln Leu
            35                  40                  45

Gly Leu Gly Lys His Asn Tyr Cys Arg Asn Pro Asp Asn Arg Arg Arg
        50                  55                  60

Pro Trp Cys Tyr Val Gln Val Gly Leu Lys Pro Leu Val Gln Glu Cys
65                  70                  75                  80
```

```
Met Val His Asp Cys Ala
             85

<210> SEQ ID NO 3
<211> LENGTH: 1296
<212> TYPE: DNA
<213> ORGANISM: Homo sapiens

<400> SEQUENCE: 3
atgagagccc tgctggcgcg cctgcttctc tgcgtcctgg tcgtgagcga ctccaaaggc      60
agcaatgaac ttcatcaagt tccatcgaac tgtgactgtc taaatggagg aacatgtgtg     120
tccaacaagt acttctccaa cattcactgg tgcaactgcc caagaaaatt cggagggcag     180
cactgtgaaa tagataagtc aaaaacctgc tatgagggga atggtcactt ttaccgagga     240
aaggccagca ctgacaccat gggccggccc tgcctgccct ggaactctgc cactgtcctt     300
cagcaaacgt accatgccca cagatctgat gctcttcagc tgggcctggg gaaacataat     360
tactgcagga acccagacaa ccggaggcga ccctggtgct atgtgcaggt gggcctaaag     420
ccgcttgtcc aagagtgcat ggtgcatgac tgcgcagatg gaaaaaagcc ctcctctcct     480
ccagaagaat taaaatttca gtgtggccaa aagactctga ggccccgctt taagattatt     540 ggggagaat tcaccaccat cgagaaccag ccctggtttg cggccatcta caggaggcac     600 cggggggct ctgtcaccta cgtgtgtgga ggcagcctca tcagcccttg ctgggtgatc     660
agcgccacac actgcttcat tgattaccca aagaaggagg actacatcgt ctacctgggt     720
cgctcaaggc ttaactccaa cacgcaaggg gagatgaagt ttgaggtgga aaacctcatc     780
ctacacaagg actacagcgc tgacacgctt gctcaccaca cgacattgc cttgctgaag     840 atccgttcca aggagggcag gtgtgcgcag ccatcccgga ctatacagac catctgcctg     900
ccctcgatgt ataacgatcc ccagtttggc acaagctgtg agatcactgg ctttggaaaa     960
gagaattcta ccgactatct ctatccggag cagctgaaaa tgactgttgt gaagctgatt    1020
tcccaccggg agtgtcagca gccccactac tacggctctg aagtcaccac caaaatgctg    1080
tgtgctgctg acccacagtg gaaaacagat tcctgccagg gagactcagg ggacccctc     1140 gtctgttccc tccaaggccg catgactttg actggaattg tgagctgggg ccgtggatgt    1200
gccctgaagg acaagccagg cgtctacacg agagtctcac acttcttacc ctggatccgc    1260
agtcacacca aggaagagaa tggcctggcc tctag                               1296

<210> SEQ ID NO 4
<211> LENGTH: 21
<212> TYPE: DNA
<213> ORGANISM: Mus musculus

<400> SEQUENCE: 4
gctgaaagct ctccacctca a                                                21

<210> SEQ ID NO 5
<211> LENGTH: 22
<212> TYPE: DNA
<213> ORGANISM: Mus musculus

<400> SEQUENCE: 5
tcgttgcttg gttctccttg ta                                               22

<210> SEQ ID NO 6
<211> LENGTH: 33
<212> TYPE: DNA
```

-continued

<213> ORGANISM: Mus musculus

<400> SEQUENCE: 6
cagaatatca accaagtgat attctccatg agc                          33

<210> SEQ ID NO 7
<211> LENGTH: 16
<212> TYPE: DNA
<213> ORGANISM: Mus musculus

<400> SEQUENCE: 7
tgtgacgccc ccagga                                             16

<210> SEQ ID NO 8
<211> LENGTH: 21
<212> TYPE: DNA
<213> ORGANISM: Mus musculus

<400> SEQUENCE: 8 aacttttga ccgcccttga g                                        21

<210> SEQ ID NO 9
<211> LENGTH: 25
<212> TYPE: DNA
<213> ORGANISM: Mus musculus

<400> SEQUENCE: 9
tgcgcccaga cagaagtcat agcca                                   25

<210> SEQ ID NO 10
<211> LENGTH: 22
<212> TYPE: DNA
<213> ORGANISM: Mus musculus

<400> SEQUENCE: 10
ctgtagccca cgtcgtagtc aa                                      22

<210> SEQ ID NO 11
<211> LENGTH: 24
<212> TYPE: DNA
<213> ORGANISM: Mus musculus

<400> SEQUENCE: 11
ctcctggtat gagatagcaa atcg                                    24

<210> SEQ ID NO 12
<211> LENGTH: 23
<212> TYPE: DNA
<213> ORGANISM: Mus musculus

<400> SEQUENCE: 12
tgccccgact acgtgctcct cac                                     23

<210> SEQ ID NO 13
<211> LENGTH: 21
<212> TYPE: DNA
<213> ORGANISM: Homo sapiens

<400> SEQUENCE: 13
cacgatgcac ctgtacgatc a                                       21

<210> SEQ ID NO 14
<211> LENGTH: 23
<212> TYPE: DNA

-continued

```
<213> ORGANISM: Homo sapiens

<400> SEQUENCE: 14
agacatcacc aagcttttt gct                                          23

<210> SEQ ID NO 15
<211> LENGTH: 23
<212> TYPE: DNA
<213> ORGANISM: Homo sapiens

<400> SEQUENCE: 15
tgaactgcac gctccgggac tca                                         23

<210> SEQ ID NO 16
<211> LENGTH: 20
<212> TYPE: DNA
<213> ORGANISM: Homo sapiens

<400> SEQUENCE: 16
tcttctcgaa ccccgagtga                                             20

<210> SEQ ID NO 17
<211> LENGTH: 18
<212> TYPE: DNA
<213> ORGANISM: Homo sapiens

<400> SEQUENCE: 17
ggagctgccc ctcagctt                                               18

<210> SEQ ID NO 18
<211> LENGTH: 29
<212> TYPE: DNA
<213> ORGANISM: Homo sapiens

<400> SEQUENCE: 18
agcctgtagc ccatgttgta gcaaaccct                                   29
```

ANTIBODIES THAT BIND UROKINASE-TYPE PLASMINOGEN ACTIVATOR AND EPITOPES THEREFOR

TECHNICAL FIELD OF THE INVENTION

The present invention relates to antibodies that bind Urokinase-Type Plasminogen Activator (uPA) and to binding epitopes of uPA used to produce such antibodies. The invention also relates to methods of using such antibodies to inhibit uPA mediated inflammation.

BACKGROUND OF THE INVENTION

Urokinase-type plasminogen activator (uPA) is a serine protease that catalyzes the conversion of plasminogen to plasmin. In addition to its proteolytic properties, uPA induces cellular migration and activation of intracellular signaling pathways through mechanisms that are independent of proteolysis. uPA potentiates neutrophil functions important for host defense, including priming for superoxide production and chemotaxis. uPA enhances LPS-induced neutrophil responses, including proinflammatory cytokine expression, activation of intracellular signaling pathways involving the kinases Akt and c-Jun N-terminal kinase (JNK), and nuclear translocation of NF-κB. Transgenic mice unable to produce uPA have been shown to be protected from endotoxemia-induced, neutrophil dependent lung injury.

uPA is secreted by many cell populations, including neutrophils, endothelial and epithelial cells, as a single-chain proenzyme that possesses little or no proteolytic activity. Single chain uPA (scuPA) is converted after single cleavage between $Lys^{158}$ and $Ile^{159}$ into the proteolytically active dual chain enzyme, consisting of an $NH_2$-terminal A chain and a proteolytic domain-containing B chain. uPA is composed of three structurally independent components: (1) a growth factor domain (GFD, amino acids 1-46), (2) a kringle domain (KD, amino acids 47-135), and (3) a proteolytic domain (PD, amino acids 159-411). The GFD is responsible for the interaction of urokinase with the uPAR/CD87 receptor. The PD includes the catalytically active site of the enzyme. Enzymatic digestion of single chain uPA (scuPA) yields an amino terminal fragment (ATF), which consists of the GFD and KD, and a low molecular weight fragment (LMW-uPA). Both single chain and cleaved, two chain uPA, as well as the amino terminal fragment (ATF) of uPA, which is contains the GFD, can bind to the uPAR/CD87 receptor. uPA lacking the GFD fails to interact with uPAR/CD87, but can bind to other cell surface receptors, including integrins and those belonging to the low density lipoprotein receptor (LDLR) family either through the KD or PD.

Human uPA also enhances inflammatory responses mediated by activation of murine neutrophils exposed to submaximal stimulatory doses of LPS. The fact that human uPA is unable to bind to murine uPAR suggests that receptors other than uPAR are involved in potentiating neutrophil responses. Moreover, because the uPA GFD is known to be responsible for interactions with uPAR, uPA domains other than GFD are likely responsible for the proinflammatory effects of uPA on neutrophils.

Understanding the mechanism by which uPA mediates its proinflammatory activities could provide important information useful in selectively inhibiting uPA mediated inflammation, while retaining thrombolytic activities of uPA mediated by other mechanisms.

There is an undeveloped need to identify new agents that specifically bind or uPA and inhibit uPA mediated inflammation. Such agents would be useful for diagnostic screening and therapeutic intervention in disease states that are associated with uPA activity.

Accordingly, it is an object of the present invention to provide specific binding agents of uPA that inhibit uPA mediated inflammation. Such agents of the present invention take the form of antibodies and fragments thereof that specifically bind to uPA epitopes.

The disclosure all patents, patent applications, and other documents cited herein are hereby expressly incorporated by reference in their entirety.

SUMMARY OF THE INVENTION

In accordance with the above objectives, the inventors of the present invention have identified the region of uPA responsible for activating uPA mediated inflammatory responses, and disclose antibodies that bind this region of uPA and inhibit the ability of this region to activate uPA mediated inflammatory response.

One aspect of the present invention is directed to antibodies against uPA, or antigen-binding regions thereof, that bind to uPA epitopes involved in mediating inflammatory responses. The antibodies can be used for treatment of uPA mediated inflammation and related diseases. In particular embodiments, the antibodies or antigen-binding regions thereof are derived from human antibodies or antigen-binding regions thereof. In other embodiments, the antibodies or antigen-binding fragments thereof are selected from the group consisting of scFv, Fab, $F(ab')_2$, Fv, and single chain antibodies, and can in particular be scFv fragments, and more particularly an scFv-Fc fusion. In another particular embodiment, the antibody or antigen-binding region thereof is a in IgG isotype, such as an IgG2 isotype.

Another aspect of the present invention is directed to isolated antibodies or antigen-binding regions thereof that bind to a uPA epitope defined by the Kringle Domain (KD) of uPA. In a particular embodiment, the antibodies of the present invention include isolated antibodies or antigen-binding regions thereof that specifically bind to a human uPA KD epitope defined by the polypeptide sequence of SEQ ID NO:2. In yet another embodiment, the antibodies of the present invention include isolated antibodies or antigen-binding regions thereof that competitively inhibit binding of the above monoclonal antibodies to a human uPA KD epitope defined by the polypeptide sequence of SEQ ID NO:2.

Another aspect of the present invention is directed to hybridoma cells and transfectoma cells which produce the antibody or antigen binding region thereof of the present invention, and antibodies or antigen-binding region thereof produced by such hybridoma and transfectoma cells. A hybridoma may include a B cell obtained from a transgenic non-human animal having a genome comprising a human heavy chain transgene and a human light chain transgene fused to an immortalized cell. A transfectoma may include nucleic acids encoding a human heavy chain and a human light chain.

Yet another aspect of the present invention is directed to a transgenic non-human animal which expresses the antibody or antigen-binding region thereof of the present invention, wherein the transgenic non-human animal has a genome comprising a human heavy chain transgene and a human light chain transgene.

Another aspect of the present invention is directed to a method of producing an antibody or antigen binding region thereof that specifically binds to a human uPA KD epitope defined by the sequence of SEQ ID NO:2, comprising: immunizing a transgenic non-human animal having a genome comprising a human heavy chain transgene and a human light chain transgene with a human uPA KD epitope defined by the sequence of SEQ ID NO:2, or a cell expressing such human uPA KD epitope, such that antibodies are produced by B cells of the animal; isolating B cells of the animal; and fusing the B cells with myeloma cells to form immortal, hybridoma cells that secrete the antibody or antigen binding region thereof.

Still another aspect of the present invention is directed to a pharmaceutical composition comprising the antibody or antigen binding region thereof of the antibodies or antigen-binding regions thereof and a carrier pharmaceutically acceptable in humans. A particular embodiment provides an antibody or antigen binding region thereof present in a therapeutically effective amount, such as in a concentration of at least about 10 µg/ml.

Yet another aspect of the present invention is directed to a method for inhibiting uPA mediated inflammation comprising administering to a patient in need thereof a therapeutically effective amount of an antibody or antigen-binding region thereof of the present invention.

Yet another aspect of the present invention is directed to uPA epitopes that mediate uPA inflammatory activity. uPA epitopes of the present invention include isolated polypeptides comprising the amino acid sequence of SEQ ID NO:2, or any fragment thereof that binds to an antibody or antigen-binding region thereof of the present invention, wherein the polypeptide does not include amino acids derived from uPA other than the amino acids of SEQ ID NO:2. In another embodiment, the present invention provides an isolated polypeptide consisting of the polypeptide sequence of SEQ ID NO:2 or any fragment thereof that binds to an antibody or antigen-binding region thereof of the present invention. In yet another embodiment, the present invention provides an isolated polypeptide consisting essentially of the polypeptide sequence of SEQ ID NO:2, or any fragment thereof that binds to an antibody or antigen-binding region thereof of the present invention.

Yet another aspect of the present invention is directed to an immunoassay comprising the steps of: (a) contacting a test sample with a first monoclonal antibody or antigen-binding region thereof capable of being competitively inhibited in its binding to a polypeptide sequence of SEQ ID NO:2 by a second monoclonal antibody or antigen-binding region thereof that specifically binds to an epitope defined by the polypeptide sequence of SEQ ID NO:2; and (b) determining the presence of human uPA in the test sample. In a particular embodiment of the above immunoassay, the first antibody or antigen-binding region inhibits uPA mediated inflammation.

Yet another aspect of the present invention is directed to a method for identifying a compound that specifically binds to an epitope defined by the polypeptide sequence of SEQ ID NO:2, comprising: contacting a test compound with the epitope for a time sufficient to form a complex and detecting the formation of a complex by detecting the epitope or the compound in the complex, so that if a complex is detected, a compound that binds to the epitope is identified.

Yet another aspect of the present invention is directed to a method for identifying a compound that specifically binds to an epitope defined by the polypeptide sequence of SEQ ID NO:2, comprising: providing atomic coordinates defining a three-dimensional structure of the epitope, and designing or selecting compounds capable of binding the epitope based on the atomic coordinates.

DETAILED DESCRIPTION OF THE INVENTION

Figure 1:
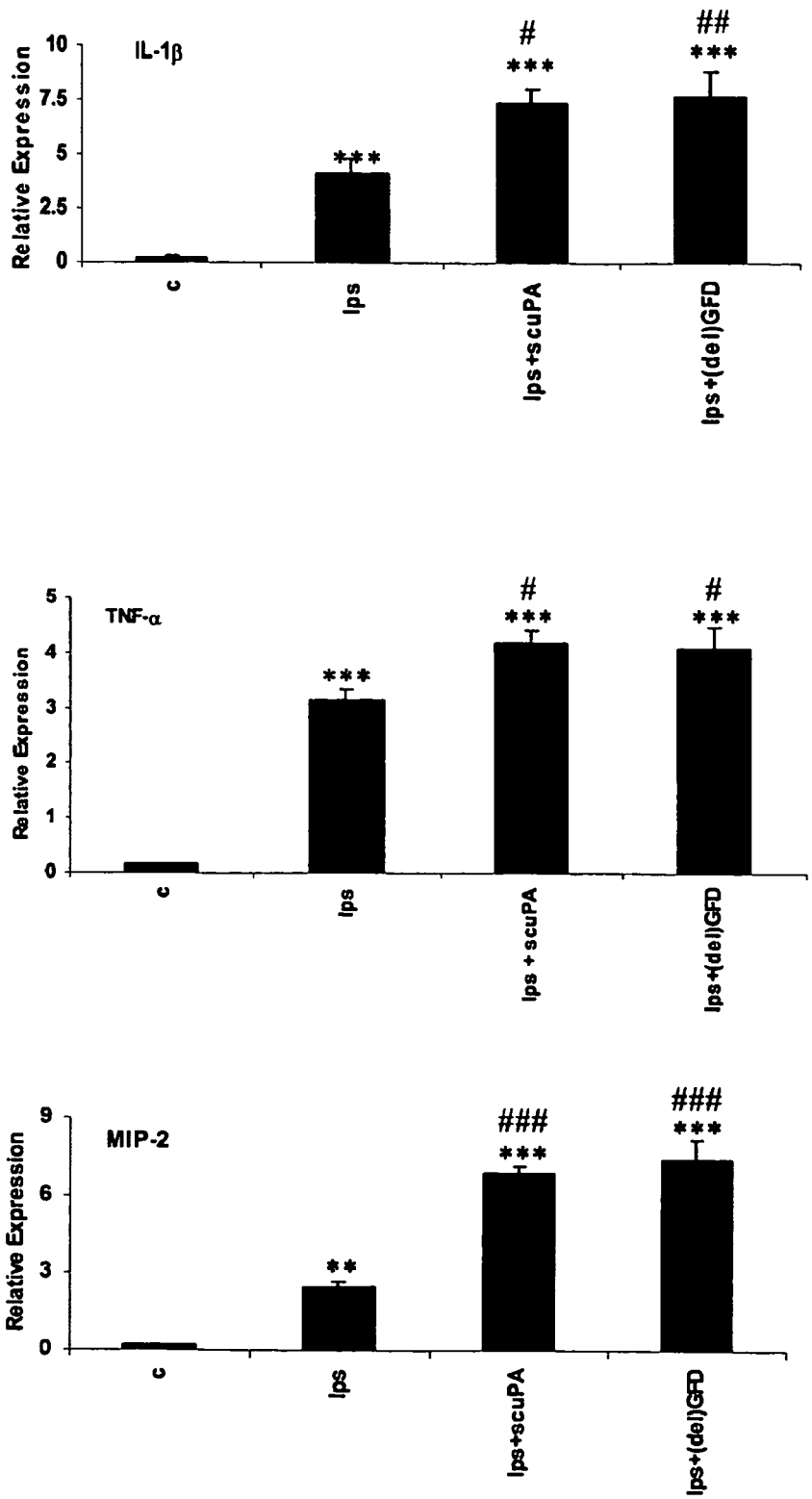
FIG. 1 indicates that the GFD of uPA is not required for enhancement of LPS-induced cytokine expression in neutrophils. Neutrophils were incubated without (Control) or with LPS 10 ng/ml (LPS) and single chain uPA (scuPA) or a deletion mutant of scuPA lacking the GFD [(del)GFD] 10 nM for 4 hours. Cytokine mRNA levels were determined by quantitative RT-PCR normalized to GAPDH. $p<0.01$ and *$p<0.001$ versus Control. #$p<0.05$, ##$p<0.01$, and ###$p<0.001$ versus LPS alone.

In order that the present invention may be more readily understood, certain terms are first defined. Additional definitions are set forth throughout the detailed description.

DEFINITIONS

Units, prefixes, and symbols may be denoted in their SI accepted form. Unless otherwise indicated, nucleic acids are written left to right in 5' to 3' orientation; amino acid sequences are written left to right in amino to carboxy orientation. Numeric ranges recited herein are inclusive of the numbers defining the range and include and are supportive of each integer within the defined range. Amino acids may be referred to herein by either their commonly known three letter symbols or by the one-letter symbols recommended by the IuPAC-IUBMB Nomenclature Commission. Nucleotides, likewise, may be referred to by their commonly accepted single-letter codes. Unless otherwise noted, the terms "a" or "an" are to be construed as meaning "at least one of". The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose. In the case of any amino acid or nucleic sequence discrepancy within the application, the figures control.

Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)), which is incorporated herein by reference. The nomenclatures utilized in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

The term "human uPA" is the protein referred to as human urokinase-type plasminogen activator, as disclosed in Blood 102, 3600-8, 2003; J Biol Chem 275:16450, 2000, and *J. Biol. Chem.* 277(43):40499-504, 2002), the contents of which are incorporated herein by reference, including allelic variants thereof. By "kringle domain" or "KD" of human uPA is meant the portion of human uPA localized between about residues 47-135 of NCBI (National Center for Biotechnology Information) Accession No. AAP36055 (version AAP36055.1), submitted May 13, 2003, incorporated by reference herein and available on the intranet.

The term "antibody" includes both glycosylated and non-glycosylated immunoglobulins of any isotype or subclass or combination thereof, including human (including CDR-grafted antibodies), humanized, chimeric, multi-specific, monoclonal, polyclonal, and oligomers thereof, irrespective of whether such antibodies are produced, in whole or in part, via immunization, through recombinant technology, by way of in vitro synthetic means, or otherwise. Thus, the term "antibody" includes those that are prepared, expressed, created or isolated by recombinant means, such as (a) antibodies isolated from an animal (e.g., a mouse) that is transgenic for human immunoglobulin genes or a hybridoma prepared therefrom, (b) antibodies isolated from a host cell transfected to express the antibody, e.g., from a transfectoma, (c) antibodies isolated from a recombinant, combinatorial antibody library, and (d) antibodies prepared, expressed, created or isolated by any other means that involve splicing of immunoglobulin gene sequences to other DNA sequences. Such antibodies have variable and constant regions derived from germline immunoglobulin sequences of two distinct species of animals. In certain embodiments, however, such antibodies can be subjected to in vitro mutagenesis (or, when an animal transgenic for human immunoglobulin sequences is used, in vivo somatic mutagenesis) and thus the amino acid sequences of the VH and VL regions of the antibodies are sequences that, while derived from and related to the germline VH and VL sequences of a particular species (e.g., human), may not naturally exist within that species' antibody germline repertoire in vivo.

A whole antibody is a glycoprotein comprising at least two heavy (H) chains and two light (L) chains inter-connected by disulfide bonds, or an antigen-binding region thereof. Each heavy chain is comprised of a heavy chain variable region (abbreviated herein as VH) and a heavy chain constant region, comprised of three domains (abbreviated herein as CH1, CH2 and CH3). Each light chain is comprised of a light chain variable region (abbreviated herein as VL) and a light chain constant region, comprised of one domain (abbreviated herein as CL). The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system. An amino acid sequence which is substantially the same as a heavy or light chain CDR exhibits a considerable amount or extent of sequence identity when compared to a reference sequence and contributes favorably to specific binding of an antigen bound specifically by an antibody having the reference sequence. Such identity is definitively known or recognizable as representing the amino acid sequence of the particular human monoclonal antibody. Substantially the same heavy and light chain CDR amino acid sequence can have, for example, minor modifications or conservative substitutions of amino acids so long as the ability to bind a particular antigen is maintained. The term "human monoclonal antibody" is intended to include a monoclonal antibody with substantially human CDR amino acid sequences produced, for example, by recombinant methods, by lymphocytes or by hybridoma cells.

The term "antigen-binding region" of an antibody means one or more fragments of an antibody that retain the ability to specifically bind to an antigen (e.g., uPA) that is specifically bound by a reference antibody, as disclosed herein. An "antigen-binding regions" of an antibody may include, for example, polypeptides comprising individual heavy or light chains and fragments thereof, such as VL, VH and Fd regions; monovalent fragments, such as Fv, Fab, and Fab' regions; bivalent fragments such as F(ab')$_2$; single chain antibodies, such as single chain Fv (scFv) regions; Fc fragments; diabodies; Fd (consisting of the VH and CH1 domains), maxibodies (bivalent scFV fused to the amino terminus of the Fc (CH2-CH3 domains) of IgG1) and complementarity determining region (CDR) domains. Such terms are described, for example, in Harlow and Lane, Antibodies: A Laboratory Manual, Cold Spring Harbor Laboratory, N.Y. (1989); Molec. Biology and Biotechnology: A Comprehensive Desk Reference (Myers, R. A. (ed.), New York: VCH Publisher, Inc.); Huston et al., Cell Biophysics, 22:189-224 (1993); Pluckthun and Skerra, Meth. Enzymol., 178:497-515 (1989) and in Day, E. D., Advanced Immunochemistry, Second Ed., Wiley-Liss, Inc., New York, N.Y. (1990), which are incorporated herein by reference. The term "antigen-binding region" also includes, for example, fragments produced by protease digestion or reduction of a human monoclonal antibody and by recombinant DNA methods known to those skilled in the art. One skilled in the art knows that the exact boundaries of a fragment of a human monoclonal antibody can be variable, so long as the fragment maintains a functional activity. Using well-known recombinant methods, one skilled in the art can engineer a nucleic acid to express a functional fragment with any endpoints desired for a particular application. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding region" of an antibody. These antibody fragments are obtained using conventional techniques known to those with skill in the art, and the fragments are screened for utility in the same manner as are intact antibodies. Such fragments include those obtained by amino-terminal and/or carboxy-terminal deletions, but where the remaining amino acid sequence is substantially identical to the corresponding positions in the naturally-occurring sequence deduced, for example, from a full-length cDNA sequence. Antigen binding regions also include fragments of an antibody which retain at least one (e.g., 1, 2, 3 or more) heavy chain sequences and/or at least one (e.g., 1, 2, 3 or more) light chain sequences for a particular complementarity determining region (CDR) (i.e., at least one or more of CDR1, CDR2, and/or CDR3 from the heavy and/or light chain). Fusions of CDR containing sequences to an Fc region (or a constant heavy 2 (CH2) or constant heavy 3 (CH3) containing region thereof) are included within the scope of this definition including, for example, scFV fused, directly or indirectly, to an Fc are included herein. An antigen binding region is inclusive of, but not limited to, those derived from an antibody or fragment thereof (e.g., by enzymatic digestion or reduction of disulfide bonds), produced synthetically using recombinant methods (e.g., transfectomas), created via in vitro synthetic means (e.g., Merrifield resins), combinations thereof, or through other methods. Antigen-binding regions may also comprise multiple fragments, such as CDR fragments, linked together synthetically, chemically, or otherwise, in the form of oligomers. Thus, antigen binding regions of the present invention include polypeptides produced by any number of methods which comprise at least one CDR from a VH or VL chain of the present invention (e.g., Ab-1 through Ab-8).

The term "$V_L$ fragment" means a fragment of the light chain of a human monoclonal antibody which includes all or part of the light chain variable region, including the CDRs. A VL fragment can further include light chain constant region sequences.

The term "Fd fragment" means a fragment of the heavy chain of a human monoclonal antibody which includes all or part of the VH heavy chain variable region, including the CDRS. An Fd fragment can further include CH1 heavy chain constant region sequences.

The term "Fv fragment" means a monovalent antigen-binding fragment of a human monoclonal antibody, including all or part of the variable regions of the heavy and light chains, and absent of the constant regions of the heavy and light chains. The variable regions of the heavy and light chains include, for example, the CDRs. For example, an Fv fragment includes all or part of the amino terminal variable region of about 110 amino acids of both the heavy and light chains.

The term "Fab fragment" means a monovalent antigen-binding fragment of an antibody consisting of the VL, VH, CL and CH1 domains, which is larger than an Fv fragment. For example, an Fab fragment includes the variable regions, and all or part of the first constant domain of the heavy and light chains. Thus, a Fab fragment additionally includes, for example, amino acid residues from about 110 to about 220 of the heavy and light chains.

The term "Fab' fragment" means a monovalent antigen-binding fragment of a human monoclonal antibody that is larger than a Fab fragment. For example, a Fab' fragment includes all of the light chain, all of the variable region of the heavy chain, and all or part of the first and second constant domains of the heavy chain. For example, a Fab' fragment can additionally include some or all of amino acid residues 220 to 330 of the heavy chain.

The term "F(ab')$_2$ fragment" means a bivalent antigen-binding fragment of a human monoclonal antibody comprising two Fab fragments linked by a disulfide bridge at the hinge region. An F(ab')$_2$ fragment includes, for example, all or part of the variable regions of two heavy chains and two light chains, and can further include all or part of the first constant domains of two heavy chains and two light chains.

The term "dAb fragment" means a fragment consisting of the VH domain, as described by Ward et al., (1989) Nature 341:544-546).

The term "CDR" means the non-contiguous antigen combining sites found within the variable region of both heavy and light chain polypeptides. This particular region has been described by Kabat et al., U.S. Dept. of Health and Human Services, "Sequences of Proteins of Immunological Interest" (1983) and by Chothia et al., J. Mol. Biol. 196:901-917 (1987) and additionally by MacCallum et al., J. Mol. Biol. 262:732-745 (1996), which are incorporated herein by reference, where the definitions include overlapping or subsets of amino acid residues when compared against each other. Nevertheless, application of either definition to refer to a CDR of an antibody or functional fragment thereof is intended to be within the scope of the term as defined and used herein. The exact amino acid residue numbers which encompass a particular CDR will vary depending on the structure of the CDR. Those skilled in the art can routinely determine which residues comprise a particular CDR given the variable region amino acid sequence of the antibody. Those skilled in the art can compare two or more antibody sequences by defining regions or individual amino acid positions of the respective sequences with the same CDR definition.

The term "CDR-grafted" refers to an antibody or antigen binding region in which the CDRs derived from one species are inserted into the framework of a different species, such as murine CDRs grafted on a human framework (a "human" antibody).

The term "analog" means polypeptides which are comprised of a segment of at least 25 amino acids that has substantial identity to a portion of a deduced amino acid sequence and which has at least one of the following properties: (1)

specific binding to uPA, under suitable binding conditions, (2) ability to block uPA ligands or receptors from binding to uPA, or (3) ability to inhibit uPA mediated inflammation. Typically, polypeptide analogs comprise a conservative amino acid substitution (or addition or deletion) with respect to the naturally-occurring sequence. Analogs typically are at least 20 amino acids long, preferably at least 50 amino acids long or longer, and can often be as long as a full-length naturally-occurring polypeptide.

The term "isolated" means separated from one or more compound that is found with the antibody or polypeptide in nature or in a synthetic reaction used to produce the antibody including, for example, a reagent, precursor or other reaction product, and preferably substantially free from any other contaminating mammalian polypeptides that would interfere with its therapeutic or diagnostic use. An isolated agent also includes a substantially pure agent. The term can include naturally occurring molecules such as products of biosynthetic reactions or synthetic molecules. An antibody is also considered "isolated," for example, when it is substantially free of other antibodies having different antigenic specificities. Also, a substance is "isolated" if it is bound or conjugated to a polypeptide or other substance to which is not bound in nature.

The term "substantially pure" means a substance that is the predominant species present (i.e., on a molar basis it is more abundant than any other individual species in the composition) and comprises at least about 50 percent (on a molar basis) of all macromolecular species present. Generally, a substantially pure composition will comprise more than about 80 percent of all macromolecular species present in the composition, or alternatively more than about 85%, 90%, 95%, and 99%. A substance is purified to essential homogeneity (contaminant species cannot be detected in the composition by conventional detection methods) wherein the composition consists essentially of a single macromolecular species. Similarly, a substance is "isolated" if in the course of manufacture or formulation it is "isolated" or "substantially pure" as described above, and then combined with other agents in a well-defined composition, notwithstanding the substance in the well-defined composition is not the predominant species present.

As used herein, the terms "specifically binds" and "specific binding" mean that a compound preferentially or selectively recognizes and binds mature, full-length or partial-length epitope of uPA, or an ortholog thereof, such that its affinity (as determined by, e.g., Affinity ELISA or BIAcore assays) or its neutralization capability (as determined by e.g., Neutralization ELISA assays, or similar assays) is at least 10 times as great, but optionally 50 times as great, 100, 250 or 500 times as great, or even at least 1000 times as great as the affinity or neutralization capability of the same for any other polypeptide, wherein the peptide portion of the peptibody is first fused to a human Fc moiety for evaluation in such assay. Typically, the antibody binds with an affinity of at least about $1\times10^7$ $M^{-1}$, and binds to the predetermined antigen with an affinity that is at least two-fold greater than its affinity for binding to a non-specific antigen (e.g., BSA, casein) other than the predetermined antigen or a closely-related antigen. As used herein, an antibody "recognizing" or "specific for" an antigen is considered equivalent to "binding specifically" to an antigen. An antibody that specifically binds to a specified epitope, isoform or variant of human uPA may, however, still have cross-reactivity to other related antigens, e.g., from other species (e.g., uPA species homologs) and still be considered to "specifically bind" the specified uPA epitope.

The term "epitope" refers to that portion of any molecule capable of being recognized by and bound by a specific binding agent, e.g., an antibody, at one or more of the binding agent's antigen binding regions. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents. An antibody is considered to specifically bind an antigen when the dissociation constant is less than or equal to about 1 μM, preferably less than or equal to about 100 nM and most preferably less than 10 nM. The antibodies and antigen-binding regions of such antibodies of the present invention include antibodies and antigen-binding regions thereof that are generated using the epitopic determinants defined herein, or that are generated using epitopic determinants having substantial identity to the epitopic determinants defined herein. In this context, the term "substantial identity" means that the sequences share sufficient identity that an antibody that binds to the modified epitopic determinant competitively inhibits binding of an antibody to the epitopic determinants described herein.

The phrase "competitively inhibits binding" means that an antibody recognizes, binds to or has immunospecificity for the same, or substantially the same, epitope or fragment thereof as another antibody or antigen-binding region thereof. In the context of the present invention, an isolated antibody or antigen-binding region thereof that competitively inhibits binding of a monoclonal antibody that specifically binds to a human uPA epitope defined by the sequence of SEQ ID NO:2, is able to measurably compete for binding to uPA. Typically, competitive inhibition is measured by determining the amount of a reference antibody or antigen binding region which is bound to the target protein (e.g., human uPA) in the presence of the tested antibody or antigen binding region thereof. Usually the tested antibody or tested antigen binding region is present in excess, such as 5-, 10-, 25-, or 50-fold excess. Competitively bound antibodies or antigen binding regions will, when present in excess, inhibit specific binding of a reference antibody or antigen binding region to the human uPA by a statistically significant degree, often at least 10%, 25%, 50%, 75%, 90% or greater. Competitive inhibition assays are well known in the art. See, for example, Harlow and Lane (1998), Antibodies, A Laboratory Manual, Cold Spring Harbor Publications, New York. As used herein, inhibition of binding encompasses both partial and complete inhibition/blocking. Inhibition and blocking are also intended to include any measurable decrease in the binding affinity of a particular anti-uPA antibody to uPA when in contact with an anti-uPA antibody of the present invention, e.g., the blocking of binding by at least about 10%, 20%, 30%, 40%, 50%, 60%, 70%, 80%, 90%, 99%, or 100%.

The identification of one or more antibodies that competitively inhibits binding of a monoclonal antibody that specifically binds to a human uPA epitope defined by the sequence of SEQ ID NO:2 is a straightforward technical matter given the determination of the above epitopes defined by such amino acids. Upon generation of an antibody that specifically binds to a human uPA epitope defined by the sequence of SEQ ID NO:2, identification of antibodies that competitively inhibit binding of those antibodies to uPA is readily determined simply by comparison to the reference antibody using methods familiar to those in the art.

The identification of cross-reactive antibodies can be readily determined using any one of variety of immunological screening assays in which antibody competition can be assessed. Such assays are routine in the art. U.S. Pat. No. 5,660,827, issued Aug. 26, 1997, is specifically incorporated herein by reference for purposes including even further supplementing the present teaching concerning how to make antibodies that bind to the same or substantially the same epitope as a given antibody.

For example, where the test antibodies to be examined are obtained from different source animals, or are even of a different isotype, a simple competition assay may be employed in which the control and test antibodies are admixed (or pre-adsorbed) and applied to a uPA antigen composition that contains a uPA epitope as described herein. Thus, protocols based upon ELISAs and Western blotting are suitable for use in such simple competition studies.

In certain embodiments, one would or pre-mix the control antibodies with varying amounts of the test antibodies (e.g., 1:10 or 1:100) for a period of time prior to applying to an antigen composition. In other embodiments, the control and varying amounts of test antibodies can simply be admixed during exposure to the antigen composition. In any event, by using species or isotype secondary antibodies one will be able to detect only the bound control antibodies, the binding of which will be reduced by the presence of a test antibody that recognizes substantially the same epitope.

In conducting an antibody competition study between a control antibody and any test antibody (irrespective of species or isotype), one may first label the control with a detectable label, such as, e.g., biotin or an enzymatic (or even radioactive) label to enable subsequent identification. In these cases, one would pre-mix or incubate the labeled control antibodies with the test antibodies to be examined at various ratios (e.g., 1:10 or 1:100) and (optionally after a suitable period of time) then assay the reactivity of the labeled control antibodies and compare this with a control value in which no potentially competing test antibody was included in the incubation.

The assay may again be any one of a range of immunological assays based upon antibody hybridization, and the control antibodies would be detected by means of detecting their label, e.g., using streptavidin in the case of biotinylated antibodies or by using a chromogenic substrate in connection with an enzymatic label (such as 3,3'5,5'-tetramethylbenzidine (TMB) substrate with peroxidase enzyme) or by simply detecting a radioactive label. An antibody that binds to the same epitope as the control antibodies will be able to effectively compete for binding and thus will significantly reduce control antibody binding, as evidenced by a reduction in bound label.

The reactivity of the (labeled) control antibodies in the absence of a completely irrelevant antibody would be the control high value. The control low value would be obtained by incubating the labeled antibodies with unlabelled antibodies of exactly the same type, when competition would occur and reduce binding of the labeled antibodies. In a test assay, a significant reduction in labeled antibody reactivity in the presence of a test antibody is indicative of a test antibody that recognizes the same epitope, i.e., one that "cross-reacts" with the labeled antibody.

The phrase "inhibits inflammation" means a statistically significant reduction in the level of inflammation relative to an untreated control. Exemplary reductions are from at least 5 to 99%, and thus include at least 10%, 20%, 30%, 40%, 50%, 60%, 70%, 80%, or 90% reduction in inflammation relative to a negative control. Widely accepted functional assays of inflammation include assays for the release of cytokines, reactive oxygen and nitrogen intermediates, inflammatory mediators (myeloperoxidase, elastase) and other markers of cellular activation by neutrophils, macrophages, endothelial cells, lymphocytes and other cell populations stimulated with bacterial products (e.g. LPS, peptidoglycan, lipotechoic acid, bacterial DNA, bacterial flagellin), cytokines (e.g. IL-1β, TNF-α), mitogens (e.g. PMA, PHA). Cell migration, assays, including neutrophil, macrophage, and monocyte chemotaxis, are also useful as a measure of inflammation. Inflammation may also be measured by assays that detect cell death, including apoptosis and necrosis. Antibacterial activity, including bacterial phagocytosis and killing, may also be useful determinants of inflammation.

It is understood that the antibodies of the present invention may be modified, such that they are substantially identical to the antibody polypeptide sequences, or fragments thereof, and still bind the uPA epitopes of the present invention. Polypeptide sequences are "substantially identical" when, optimally aligned using such programs as GAP or BESTFIT using default gap weights, they share at least 80 percent sequence identity, at least 90 percent sequence identity, at least 95 percent sequence identity, or at least 99 percent sequence identity. Preferably, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, glutamic-aspartic, and asparagine-glutamine.

As discussed herein, minor variations in the amino acid sequences of antibodies or immunoglobulin molecules are contemplated as being encompassed by the present invention, providing that the variations in the amino acid sequence maintain at least 75%, more preferably at least 80%, 90%, 95%, and most preferably 99%. In particular, conservative amino acid replacements are contemplated. Conservative replacements are those that take place within a family of amino acids that are related in their side chains. Genetically encoded amino acids are generally divided into families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). More preferred families are: serine and threonine are aliphatic-hydroxy family; asparagine and glutamine are an amide-containing family; alanine, valine, leucine and isoleucine are an aliphatic family; and phenylalanine, tryptophan, and tyrosine are an aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the polypeptide derivative. Assays are described in detail herein. Fragments or analogs of antibodies or immunoglobulin molecules can be readily prepared by those of ordinary skill in the art. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Methods to identify protein sequences that fold into a known three-dimensional structure are known. Bowie et al. Science 253:164 (1991). Thus, the foregoing examples demonstrate that those of skill in the art can recognize sequence motifs and structural conformations that may be used to define structural and functional domains in accordance with the invention.

Preferred amino acid substitutions are those which: (1) reduce susceptibility to proteolysis, (2) reduce susceptibility to oxidation, (3) alter binding affinity for forming protein complexes, (4) alter binding affinities, and (4) confer or modify other physicochemical or functional properties of such analogs. Analogs can include various muteins of a sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et al. Nature 354:105 (1991), which are each incorporated herein by reference.

The antibodies of the present invention may also be generated using peptide analogs of the epitopic determinants disclosed herein, which analogs may consist of non-peptide compounds having properties analogous to those of the template peptide. These types of non-peptide compound are termed "peptide mimetics" or "peptidomimetics". Fauchere, J. Adv. Drug Res. 15:29 (1986); Veber and Freidinger TINS p. 392 (1985); and Evans et al. J. Med. Chem. 30:1229 (1987). Such compounds are often developed with the aid of computerized molecular modeling. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a biochemical property or pharmacological activity), such as human antibody, but have one or more peptide linkages optionally replaced by a linkage selected from the group consisting of: —CH₂NH—, —CH₂S—, —CH₂—CH₂—, —CH═CH— (cis and trans), —COCH₂—, —CH(OH)CH₂—, and CH₂SO—, by methods well known in the art. Systematic substitution of one or more amino acids of a consensus sequence with a D-amino acid of the same type (e.g., D-lysine in place of L-lysine) may be used to generate more stable peptides. In addition, constrained peptides comprising a consensus sequence or a substantially identical consensus sequence variation may be generated by methods known in the art (Rizo and Gierasch Ann. Rev. Biochem. 61:387 (1992), incorporated herein by reference); for example, by adding internal cysteine residues capable of forming intramolecular disulfide bridges which cyclize the peptide.

The term "bispecific molecule" is intended to include any agent, e.g., a protein, peptide, or protein or peptide complex, which has at least two different binding specificities. For example, the molecule may bind to, or interact with, (a) a cell surface antigen and (b) an Fc receptor on the surface of an effector cell. The term "multispecific molecule" or "heterospecific molecule" is intended to include any agent, e.g., a protein, peptide, or protein or peptide complex, which has more than two different binding specificities. For example, the molecule may bind to, or interact with, (a) a cell surface antigen, (b) an Fc receptor on the surface of an effector cell, and (c) at least one other component. Accordingly, the invention includes, but is not limited to, bispecific, trispecific, tetraspecific, and other multispecific molecules which are directed to uPA epitopes, and to other targets, such as Fc receptors on effector cells. The term "bispecific antibodies" also includes diabodies. Diabodies are bivalent, bispecific antibodies in which the VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al (1993) Proc. Natl. Acad. Sci. USA 90:6444-6448; Poljak, R. J., et al. (1994) Structure 2:1121-1123). A bispecific antibody includes two or more antibodies, antibody binding fragments (e.g., Fab), derivatives therefrom, or antigen binding regions linked together, at least two of which have different specificities. These different specificities include a binding specificity for an Fc receptor on an effector cell, and a binding specificity for an antigen or epitope on a target cell, e.g., a tumor cell.

The term "human antibody" refers to an antibody in which both the constant regions and the framework consist of fully or substantially human sequences such that the human antibody elicits substantially no immunogenic reaction against itself when administered to a human host and preferably, no detectable immunogenic reaction. It is to be understood that a "human antibody" need not consist entirely of human sequences, but may contain portions of non-human sequences, provided that the antibody does not elicit an immunogenic reaction when administered to the human host. For example, a "human antibody" includes antibodies in which CDR regions of non-human species, such as a mouse, are grafted on a human framework. In certain embodiments, human antibodies are produced in non-human mammals, including, but not limited to, mice, rats, and lagomorphs. In other embodiments, human antibodies are produced in hybridoma cells from transgenic animals having a human immunoglobulin repertoire. In other embodiments, fully human antibodies are produced recombinantly, such as in a transfectoma.

The term "humanized antibody" refers to an antibody in which substantially all of the constant region is derived from a human, while all or part of one or more variable regions is derived from another species, for example a mouse.

The terms "monoclonal antibody" or "monoclonal antibody composition" as used herein refer to a preparation of antibody molecules of single molecular composition. A monoclonal antibody composition displays a single binding specificity and affinity for a particular epitope. Accordingly, the term "human monoclonal antibody" refers to antibodies displaying a single binding specificity which have variable and constant regions derived from human germline immunoglobulin sequences. In one embodiment, the human monoclonal antibodies are produced by a hybridoma which includes a B cell obtained from a transgenic non-human animal, e.g., a transgenic mouse, having a genome comprising a human heavy chain transgene and a light chain transgene fused to an immortalized cell.

The term "recombinant", as used herein in reference to antibodies, is intended to include all human antibodies that are prepared, expressed, created or isolated by recombinant means, such as (a) antibodies isolated from an animal (e.g., a mouse) that is transgenic for human immunoglobulin genes or a hybridoma prepared therefrom (described further in Section I, below), (b) antibodies isolated from a host cell transformed to express the antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable and constant regions derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

As used herein, a "heterologous antibody" is defined in relation to the transgenic non-human organism producing such an antibody. This term refers to an antibody having an amino acid sequence or an encoding nucleic acid sequence corresponding to that found in an organism not consisting of the transgenic non-human animal, and generally from a species other than that of the transgenic non-human animal.

As used herein, a "heterohybrid antibody" refers to an antibody having a light and heavy chains of different organismal origins. For example, an antibody having a human heavy chain associated with a murine light chain is a heterohybrid antibody. Examples of heterohybrid antibodies include chimeric and humanized antibodies, discussed supra.

As used herein, "isotype switching" refers to the phenomenon by which the class, or isotype, of an antibody changes from one Ig class to one of the other Ig classes.

As used herein, "nonswitched isotype" refers to the isotypic class of heavy chain that is produced when no isotype switching has taken place; the CH gene encoding the non-switched isotype is typically the first CH gene immediately downstream from the functionally rearranged VDJ gene. Isotype switching has been classified as classical or non-classical isotype switching. Classical isotype switching occurs by recombination events which involve at least one switch sequence region in the transgene. Non-classical isotype switching may occur by, for example, homologous recombination between human theta-mu and human theta-mu (delta-associated deletion). Alternative non-classical switching mechanisms, such as intertransgene and/or interchromosomal recombination, among others, may occur and effectuate isotype switching.

As used herein, the term "switch sequence" refers to those DNA sequences responsible for switch recombination. A "switch donor" sequence, typically a mu switch region, will be 5' (i.e., upstream) of the construct region to be deleted during the switch recombination. The "switch acceptor" region will be between the construct region to be deleted and the replacement constant region (e.g., gamma, epsilon etc.). As there is no specific site where recombination always occurs, the final gene sequence will typically not be predictable from the construct.

As used herein, "glycosylation pattern" is defined as the pattern of carbohydrate units that are covalently attached to a protein, more specifically to an immunoglobulin protein. A glycosylation pattern of a heterologous antibody can be characterized as being substantially similar to glycosylation patterns which occur naturally on antibodies produced by the species of the nonhuman transgenic animal, when one of ordinary skill in the art would recognize the glycosylation pattern of the heterologous antibody as being more similar to said pattern of glycosylation in the species of the nonhuman transgenic animal than to the species from which the CH genes of the transgene were derived.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

The term "rearranged" as used herein refers to a configuration of a heavy chain or light chain immunoglobulin locus wherein a V segment is positioned immediately adjacent to a D-J or J segment in a conformation encoding essentially a complete VH or VL domain, respectively. A rearranged immunoglobulin gene locus can be identified by comparison to germline DNA; a rearranged locus will have at least one recombined heptamer/nonamer homology element.

The term "unrearranged" or "germline configuration" as used herein in reference to a V segment refers to the configuration wherein the V segment is not recombined so as to be immediately adjacent to a D or J segment.

The term "transfectoma", as used herein, includes recombinant eukaryotic host cell expressing the antibody, such as CHO cells or NS/0 cells.

The terms "transgenic nonhuman animal" refers to a non-human animal having a genome comprising one or more human heavy and/or light chain transgenes or transchromosomes (either integrated or non-integrated into the animal's natural genomic DNA) and which is capable of expressing fully human antibodies. For example, a transgenic mouse can have a human light chain transgene and either a human heavy chain transgene or human heavy chain transchromosome, such that the mouse produces human anti-uPA antibodies when immunized with uPA and/or cells expressing uPA. The human heavy chain transgene can be integrated into the chromosomal DNA of the mouse, as is the case for transgenic, e.g., huMAb mice, or the human heavy chain transgene can be maintained extrachromosomally, as is the case for transchromosomal (e.g., KM) mice as described in WO 02/43478. Such transgenic and transchromosomal mice are capable of producing multiple isotypes of human monoclonal antibodies to uPA (e.g., IgG, IgA and/or IgE) by undergoing V-D-J recombination and isotype switching.

Various aspects of the invention are described in further detail in the following subsections.

Production of Antibodies to uPA

The present invention is exemplified by antibodies or an antigen-binding regions thereof that bind to specified epitopes of uPA that have been determined to play a role in activation of uPA mediated inflammatory activity. Such antibodies or antigen-binding regions thereof include anti-uPA antibodies and antigen-binding regions thereof whose binding to uPA can be competitively inhibited by the antibodies or antigen-binding regions thereof disclosed herein.

The present invention provides anti-uPA antibodies that bind to substantially the same epitope as a human uPA epitope defined by the polypeptide sequences of SEQ ID NO:2. Such antibodies or antigen-binding regions thereof can be prepared by any one of a number of processes disclosed below, for example, by immunizing an animal with at least a first uPA KD antigenic composition and selecting from the immunized animal an antibody that substantially cross-reacts with the monoclonal antibodies of the present invention.

Antibodies with such combinations of properties can be readily identified by one or more or a combination of the receptor competition, ELISA, co-precipitation, and/or functional assays and the crossreactivity assays described herein.

The antibodies encompassed by the present invention include IgG, IgA, IgG1-4, IgE, IgM, and IgD antibodies, e.g., IgG1κ or IgG1λ isotypes, or IgG4κ or IgG4λ isotypes. In a particular embodiment, the antibody of the present invention is a IgG2 isotype. In one embodiment, human antibodies are produced in a non-human transgenic animal, e.g., a transgenic mouse, capable of producing multiple isotypes of human antibodies to uPA (e.g., IgG, IgA and/or IgE) by undergoing V-D-J recombination and isotype switching. Accordingly, aspects of the invention include not only antibodies, antibody fragments, and pharmaceutical compositions thereof, but also non-human transgenic animals, B-cells, host cell transfectomas, and hybridomas which produce monoclonal antibodies. Methods of using the antibodies of the invention to detect a cell expressing uPA or a related, cross-reactive growth factor receptor, or to inhibit growth, differentiation and/or motility of a cell expressing uPA, either in vitro or in vivo, are also encompassed by the invention. The present invention further encompasses pharmaceutical preparations containing the antibodies of the present invention, and methods of treating physiological disorders by administering the antibodies of the present invention.

The antibodies and antigen binding regions of the present invention can be constructed by any number of different methods, including, via immunization of animals (e.g., with an antigen that elicits the production of antibodies that specifically bind to and competitively inhibit the binding of at least one of an antibody of Ab-1 through Ab-8); via hybridomas (e.g., employing B-cells from transgenic or non-transgenic animals); via recombinant methods (e.g., CHO transfectomas; see, Morrison, S. (1985) Science 229:1202)), or, in vitro synthetic means (e.g., solid-phase polypeptide synthesis).

In some embodiments, the antibodies and antigen binding regions are human or humanized. Methods for humanizing non-human antibodies are well known in the art. Humanization can be essentially performed following the method of Winter and co-workers (Jones et al., Nature, 321:522 (1986); Riechmann et al., Nature, 332: 323 (1988); Verhoeyen et al., Science, 239: 1534 (1988)). Briefly, human constant region genes are joined to appropriate human or non-human variable region genes. For example, the amino acid sequences which represent the antigen binding sites (CDRS, or complimentarity determining regions) of a parent murine monoclonal antibody are grafted at the DNA level onto human variable region framework sequences. The sequences of human constant regions genes may be found in Kabat et al. (1991) Sequences of Proteins of Immunological Interest, N.I.H. publication no. 91-3242. Human C region genes are readily available from known clones. The choice of antibody isotype will be guided by the desired effector functions, such as complement fixation, or activity in antibody-dependent cellular cytotoxicity. In certain embodiments, the isotype is $IgG_2$.

Human or humanized antibodies or antigen binding regions can also be generated through display-type technologies, including, without limitation, phage display, retroviral display, ribosomal display, and other techniques, using techniques well known in the art and the resulting molecules can be subjected to additional maturation, such as affinity maturation, as such techniques are well known in the art. Hanes and Plucthau, PNAS USA 94:4937-4942 (1997) (ribosomal display), Parmley and Smith, Gene 73:305-318 (1988) (phage display), Scott, TIBS 17:241-245 (1992), Cwirla et al., PNAS USA 87:6378-6382 (1990), Russel et al., Nucl. Acids Research 21:1081-1085 (1993), Hoganboom et al., Immunol. Reviews 130:43-68 (1992), Chiswell and McCafferty, TIBTECH 10:80-84 (1992), and U.S. Pat. No. 5,733,743.

Identification of suitable human antibody sequences may be facilitated by computer modeling. Modeling is well known in the art, and are used, for example, to avoid unnatural juxtaposition of non-human CDR regions with human variable framework regions, which can result in unnatural conformational restraints and concomitant loss of binding affinity. Computer hardware and software for producing three-dimensional images of immunoglobulin molecules are widely available. In general, molecular models are produced starting from solved structures for immunoglobulin chains or domains thereof. The chains to be modeled are compared for amino acid sequence similarity with chains or domains of solved three dimensional structures, and the chains or domains showing the greatest sequence similarity are selected as starting points for construction of the molecular model. The solved starting structures are modified to allow for differences between the actual amino acids in the immunoglobulin chains or domains being modeled, and those in the starting structure. The modified structures are then assembled into a composite immunoglobulin. Finally, the model is refined by energy minimization and by verifying that all atoms are within appropriate distances from one another and that bond lengths and angles are within chemically acceptable limits.

It is now possible to produce transgenic animals (e.g. mice) that are capable, upon immunization, of producing a full repertoire of human antibodies in the absence of endogenous immunoglobulin production. For example, the homozygous deletion of the antibody heavy-chain joining region (JH) gene in chimeric and germ-line mutant mice results in complete inhibition of endogenous antibody production. Transfer of the human germ-line immunoglobulin gene array in such germline mutant mice will result in the production of human antibodies upon antigen challenge. See, e.g., Jakobovits et al., Proc. Natl. Acad. Sci. USA, 90: 2551 (1993); Jakobovits et al., Nature, 362: 255 (1993); Bruggermann et al., Year in Immunol., 20 7: 33 (1993). Commercially accessible transgenic mice strains such as XenoMouse have been described; see, Green et al. Nature Genetics 7:13-21 (1994).

Recombinant methods for producing antibodies or antigen binding regions of the present invention begin with the isolated nucleic acid of desired regions of the immunoglobulin heavy and light chains. Such regions can include, for example, all or part of the variable region of the heavy and light chains. Such regions can, in particular, include at least one of the CDRs of the heavy and/or light chains, and often, at least one CDR pair. A nucleic acid encoding an antibody or antigen binding region of the invention can be directly synthesized by methods of in vitro oligonucleotide synthesis known in the art. Alternatively, smaller fragments can be synthesized and joined to form a larger fragment using recombinant methods known in the art. Antibody binding regions, such as for Fab or F(ab')$_2$, may be prepared by cleavage of the intact protein, e.g. by protease or chemical cleavage. Alternatively, a truncated gene can be designed.

To express the antibodies or antigen binding regions thereof, DNAs encoding partial or full-length light and heavy chains, can be obtained by standard molecular biology techniques (e.g., PCR amplification, site directed mutagenesis) and can be inserted into expression vectors such that the genes are operatively linked to transcriptional and translational regulatory sequences. Nucleic acids encoding an antibody or antigen binding region of the invention can be cloned into a suitable expression vector and expressed in a suitable host. A suitable vector and host cell system can allow, for example, co-expression and assembly of the variable heavy and variable light chains, or CDR containing polypeptides thereof. Suitable systems for expression can be determined by those skilled in the art.

Nucleic acids comprising polynucleotides of the present invention can be used in transfection of a suitable mammalian or nonmammalian host cells. In some embodiments, for expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the invention in either prokaryotic or eukaryotic host cells, expression of antibodies in eukaryotic cells, and most preferably mammalian host cells, is the most typical because such eukaryotic cells, and in particular mammalian cells, are more likely than prokaryotic cells to assemble and secrete a properly folded and immunologically active antibody or antigen binding region.

Expression vectors include plasmids, retroviruses, cosmids, YACs, EBV derived episomes, and the like. A convenient vector is one that encodes a functionally complete human CH (constant heavy) or CL (constant light) immunoglobulin sequence, with appropriate restriction sites engineered so that any VH or VL sequence can be easily inserted and expressed. In such vectors, splicing usually occurs between the splice donor site in the inserted J region and the splice acceptor site preceding the human C region, and also at the splice regions that occur within the human CH exons. Polyadenylation and transcription termination occur at native chromosomal sites downstream of the coding regions.

The expression vector and expression control sequences are chosen to be compatible with the expression host cell used. The antibody variable heavy chain nucleic acid and the antibody variable light chain nucleic acids of the present invention can be inserted into separate vectors or, frequently, both genes are inserted into the same expression vector. The nucleic acids can be inserted into the expression vector by standard methods (e.g., ligation of complementary restriction sites on the antibody nucleic acid fragment and vector, or blunt end ligation if no restriction sites are present). The heavy and light chain variable regions can be used to create full-length antibody genes of any antibody isotype by inserting them into expression vectors already encoding heavy chain constant and light chain constant regions of the desired isotype (and subclass) such that the VH segment is operatively linked to the CH segment(s) within the vector and the VL segment is operatively linked to the CL segment within the vector. Additionally or alternatively, the expression vector can encode a signal peptide that facilitates secretion of the antibody or antigen binding region chain from a host cell. The antibody or antigen binding region chain gene can be cloned into the vector such that the signal peptide is linked in-frame to the amino terminus of the antibody/antigen binding region chain gene. The signal peptide can be an immunoglobulin signal peptide or a heterologous signal peptide (i.e., a signal peptide from a non-immunoglobulin protein).

In addition to the CDR comprising sequence, the expression vectors of the invention carry regulatory sequences that control the expression of the sequence in a host cell. The term "regulatory sequence" is intended to includes promoters, enhancers and other expression control elements (e.g., polyadenylation signals) that control the transcription or translation of the antibody chain genes. Such regulatory sequences are described, for example, in Goeddel; Gene Expression Technology. Methods in Enzymology 185, Academic Press, San Diego, Calif. (1990). It will be appreciated by those skilled in the art that the design of the expression vector, including the selection of regulatory sequences may depend on such factors as the choice of the host cell to be transformed, the level of expression of protein desired, and the like. Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP)) and polyoma. Alternatively, nonviral regulatory sequences may be used, such as the ubiquitin promoter or beta-globin promoter.

In addition to the antibody or antigen binding region nucleic acids and regulatory sequences, the expression vectors of the invention may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634,665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

Preferred mammalian host cells for expressing the recombinant antibodies or antigen binding regions of the invention include Chinese Hamster Ovary (CHO cells) (including dhfr-CHO cells, described in Urlaub and Chasin, (1980) Proc. Natl. Acad. Sci. USA 77:4216-4220, used with a DHFR selectable marker, e.g., as described in R. J. Kaufman and P. A. Sharp (1982) Mol. Biol. 159:601-621), NS/0 myeloma cells, COS cells and SP2.0 cells. In particular for use with NS/0 myeloma cells, another preferred expression system is the GS gene expression system disclosed in WO 87/04462, WO 89/01036 and EP 338 841. When expression vectors of the invention are introduced into mammalian host cells, the antibodies or antigen binding regions are produced by culturing the host cells for a period of time sufficient to allow for expression of the antibody or antigen binding region in the host cells or, more preferably, secretion of the antibody or antigen binding region into the culture medium in which the host cells are grown.

Once expressed, antibodies and antigen binding regions of the invention can be purified according to standard methods in the art, including HPLC purification, fraction column chromatography, gel electrophoresis and the like (see, e.g., Scopes, Protein Purification, Springer-Verlag, NY, 1982). In certain embodiments, polypeptides are purified using chromatographic and/or electrophoretic techniques. Exemplary purification methods include, but are not limited to, precipitation with ammonium sulphate; precipitation with PEG; immunoprecipitation; heat denaturation followed by centrifugation; chromatography, including, but not limited to, affinity chromatography (e.g., Protein-A-Sepharose), ion exchange chromatography, exclusion chromatography, and reverse phase chromatography; gel filtration; hydroxylapatite chromatography; isoelectric focusing; polyacrylamide gel electrophoresis; and combinations of such and other techniques. In certain embodiments, a polypeptide is purified by fast protein liquid chromatography or by high pressure liquid chromotography (HPLC).

Generation of Hybridomas Producing Human Monoclonal Antibodies to uPA

Another aspect of the present invention includes a hybridoma cell that produces the antibody or antigen-binding region thereof of the present invention. A hybridoma cell may comprise a B cell obtained from a transgenic non-human animal having a genome comprising a human heavy chain transgene and a light chain transgene fused to an immortalized cell, wherein the hybridoma produces a detectable amount of the monoclonal antibody or antigen-binding region thereof of the present invention.

Mouse splenocytes can be isolated and fused with PEG to a mouse myeloma cell line based upon standard protocols. The resulting hybridomas are then screened for the production of antigen-specific antibodies. For example, single cell suspensions of splenic lymphocytes from immunized mice are fused to one-sixth the number of P3X63-Ag8.653 nonsecreting mouse myeloma cells (ATCC, CRL 1580) with 50% PEG. Cells are plated at approximately $2 \times 10^5$ in flat bottom microtiter plate, followed by a two week incubation in selective medium containing 20% fetal Clone Serum, 18% "653" conditioned media, 5% origen (IGEN), 4 mM L-glutamine, 1 mM L-glutamine, 1 mM sodium pyruvate, 5 mM HEPES, 0.055 mM 2-mercaptoethanol, 50 units/ml penicillin, 50 mg/ml streptomycin, 50 mg/ml gentamycin and 1×HAT (Sigma; the HAT is added 24 hours after the fusion). After two weeks, cells are cultured in medium in which the HAT is replaced with HT. Individual wells are then screened by ELISA for human anti-uPA monoclonal IgM and IgG antibodies. Once extensive hybridoma growth occurs, medium is observed usually after 10-14 days. The antibody secreting hybridomas are replated, screened again, and if still positive for human IgG, anti-uPA monoclonal antibodies, can be subcloned at least twice by limiting dilution. The stable subclones are then cultured in vitro to generate small amounts of antibody in tissue culture medium for characterization.

Generation of Transfectomas Producing Human Monoclonal Antibodies to uPA

Human antibodies of the invention can also be produced in a host cell transfectoma using, for example, a combination of recombinant DNA techniques and gene transfection methods as is well known in the art (Morrison, S. (1985) Science 229:1202). A transfectoma cell may comprise nucleic acids encoding a human heavy chain and a human light chain, wherein the transfectoma produces a detectable amount of the monoclonal antibody or antigen-binding region thereof of the present invention.

For example, to express the antibodies, or antibody fragments thereof, DNAs encoding partial or full-length light and heavy chains, can be obtained by standard molecular biology techniques (e.g., PCR amplification, site directed mutagenesis) and can be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the VH segment is operatively linked to the CH segment(s) within the vector and the VL segment is operatively linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the invention carry regulatory sequences that control the expression of the antibody chain genes in a host cell. The term "regulatory sequence" is intended to includes promoters, enhancers and other expression control elements (e.g., polyadenylation signals) that control the transcription or translation of the antibody chain genes. Such regulatory sequences are described, for example, in Goeddel; Gene Expression Technology. Methods in Enzymology 185, Academic Press, San Diego, Calif. (1990). It will be appreciated by those skilled in the art that the design of the expression vector, including the selection of regulatory sequences may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP)) and polyoma. Alternatively, nonviral regulatory sequences may be used, such as the ubiquitin promoter or beta-globin promoter.

In addition to the antibody chain genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399, 216, 4,634,665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection). In a preferred embodiment of the present invention, the antibody chain genes and regulatory sequences are expressed in "split dhfr vectors" PDC323 and PDC324, as disclosed by Bianchi, A. A. and McGrew, J. T. (2003) "High-level expression of full antibodies using trans-complementing expression vectors," Bioengineering and Biotechnology, 84 (4): 439-444; and McGrew, J. T. and Bianchi, A. A. (2002) "Selection of cells expressing heteromeric proteins," U.S. Patent Application No. 20030082735, the contents of which are expressly incorporated herein by reference.

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the invention in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody.

Preferred mammalian host cells for expressing the recombinant antibodies of the invention include Chinese Hamster Ovary (CHO cells) (including dhfr-CHO cells, described in Urlaub and Chasin, (1980) Proc. Natl. Acad. Sci. USA 77:4216-4220, used with a DHFR selectable marker, e.g., as described in R. J. Kaufman and P. A. Sharp (1982) Mol. Biol. 159:601-621), NS/0 myeloma cells, COS cells and SP2.0 cells. In particular for use with NS/0 myeloma cells, another preferred expression system is the GS gene expression system disclosed in WO 87/04462, WO 89/01036 and EP 338 841. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Use of Partial Antibody Sequences to Express Intact Antibodies

Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al., 1998, Nature 332:323-327; Jones, P. et al., 1986, Nature 321:522-525; and Queen, C. et al., 1989, Proc. Natl. Acad. See. U.S.A. 86:10029-10033). Such framework sequences can be obtained from public DNA databases that include germline antibody gene sequences. These germline sequences will differ from mature antibody gene sequences because they will not include completely assembled variable genes, which are formed by V(D)J joining during B cell maturation. Germline gene sequences will also differ from the sequences of a high affinity secondary repertoire antibody at individual evenly across the variable region.

For example, somatic mutations are relatively infrequent in the amino-terminal portion of framework region. For example, somatic mutations are relatively infrequent in the amino terminal portion of framework region 1 and in the carboxy-terminal portion of framework region 4. Furthermore, many somatic mutations do not significantly alter the binding properties of the antibody. For this reason, it is not necessary to obtain the entire DNA sequence of a particular antibody in order to recreate an intact recombinant antibody having binding properties similar to those of the original antibody (see PCT/US99/05535 filed on Mar. 12, 1999, which is herein incorporated by referenced for all purposes). Partial heavy and light chain sequence spanning the CDR regions is typically sufficient for this purpose. The partial sequence is used to determine which germline variable and joining gene segments contributed to the recombined antibody variable genes. The germline sequence is then used to fill in missing portions of the variable regions. Heavy and light chain leader sequences are cleaved during protein maturation and do not contribute to the properties of the final antibody. For this reason, it is necessary to use the corresponding germline leader sequence for expression constructs. To add missing sequences, cloned cDNA sequences cab be combined with synthetic oligonucleotides by ligation or PCR amplification. Alternatively, the entire variable region can be synthesized as a set of short, overlapping, oligonucleotides and combined by PCR amplification to create an entirely synthetic variable region clone. This process has certain advantages such as elimination or inclusion or particular restriction sites, or optimization of particular codons.

The nucleotide sequences of heavy and light chain transcripts from a hybridomas are used to design an overlapping set of synthetic oligonucleotides to create synthetic V sequences with identical amino acid coding capacities as the natural sequences. The synthetic heavy and kappa chain sequences can differ from the natural sequences in three ways: strings of repeated nucleotide bases are interrupted to facilitate oligonucleotide synthesis and PCR amplification; optimal translation initiation sites are incorporated according to Kozak's rules (Kozak, 1991, J. Biol. Chem. 266:19867-19870); and, HindIII sites are engineered upstream of the translation initiation sites.

For both the heavy and light chain variable regions, the optimized coding, and corresponding non-coding, strand sequences are broken down into 30-50 nucleotide approximately the midpoint of the corresponding non-coding oligonucleotide. Thus, for each chain, the oligonucleotides can be assemble into overlapping double stranded sets that span segments of 150-400 nucleotides. The pools are then used as templates to produce PCR amplification products of 150-400 nucleotides. Typically, a single variable region oligonucleotide set will be broken down into two pools which are separately amplified to generate two overlapping PCV products. These overlapping products are then combined by PCT amplification to form the complete variable region. It may also be desirable to include an overlapping fragment of the heavy or light chain constant region (including the BbsI site of the kappa light chain, or the AgeI site if the gamma heavy chain) in the PCR amplification to generate fragments that can easily be cloned into the expression vector constructs.

The reconstructed heavy and light chain variable regions are then combined with cloned promoter, translation initiation, constant region, 3' untranslated, polyadenylation, and transcription termination, sequences to form expression vector constructs. The heavy and light chain expression constructs can be combined into a single vector, co-transfected, serially transfected, or separately transfected into host cells which are then fused to form a host cell expressing both chains.

Plasmids for use in construction of expression vectors for human IgG1κ are described below. The plasmids were constructed so that PCR amplified V heavy and V kappa light chain cDNA sequences could be used to reconstruct complete heavy and light chain minigenes. These plasmids can be used to express completely human, or chimeric IgG1κ or IgG4κ antibodies. Similar plasmids can be constructed for expression of other heavy chain isotypes, or for expression of antibodies comprising lambda light chains.

Thus, in another aspect of the invention, the structural features of an human anti-uPA antibodies of the invention are used to create structurally related human anti-uPA antibodies that retain at least one functional property of the antibodies of the invention, such as binding to uPA. More specifically, one or more CDR regions of anti-uPA antibodies can be combined recombinantly with known human framework regions and CDRs to create additional, recombinantly-engineered, human anti-uPA antibodies of the invention.

Accordingly, anti-uPA antibodies of the present invention can be used to prepare an anti-uPA antibody by preparing an anti-uPA antibody comprising (1) human heavy chain framework regions and human heavy chain CDRs; and (2) human light chain framework regions and human light chain CDRs, wherein the antibody retains the ability to bind to uPA.

The ability of the antibody to bind uPA can be determined using standard binding assays (e.g., an ELISA). Since it is well known in the art that antibody heavy and light chain CDR3 domains play a particularly important role in the binding specificity/affinity of an antibody for an antigen, the recombinant antibodies of the invention prepared as set forth above preferably comprise the heavy and light chain CDR3s of anti-uPA antibodies. The antibodies further can comprise the CDR2s of anti-uPA antibodies. The antibodies further can comprise the CDR1s of anti-uPA antibodies. Accordingly, the invention further provides anti-uPA antibodies comprising: (1) human heavy chain framework regions, a human heavy chain CDR1 region, a human heavy chain CDR2 region, and a human heavy chain CDR3 region, wherein the human heavy chain CDR3 region is the CDR3 of anti-uPA antibodies; and (2) human light chain framework regions, a human light chain CDR1 region, a human light chain CDR2 region, and a human light chain CDR3 region, wherein the human light chain CDR3 region is the CDR3 of anti-uPA antibodies, wherein the antibody binds uPA. The antibody may further comprise the heavy chain CDR2 and/or the light chain CDR2 of anti-uPA antibodies. The antibody may further comprise the heavy chain CDR1 and/or the light chain CDR1 of anti-uPA antibodies.

Preferably, the CDR1, 2, and/or 3 of the engineered antibodies described above comprise the exact amino acid sequence(s) as those of anti-uPA antibodies generated as described herein. However, the ordinarily skilled artisan will appreciate that some deviation from the exact CDR sequences may be possible while still retaining the ability of the antibody to bind uPA effectively (e.g., conservative substitutions). Accordingly, in another embodiment, the engineered antibody may be composed of one or more CDRs that are, for example, 90%, 95%, 98% or 99.5% identical to one or more CDRs of anti-uPA antibodies.

Characterization of Binding of Human Monoclonal Antibodies to uPA

To characterize binding of anti-human uPA human monoclonal antibodies of the invention, sera from immunized mice can be tested, for example, by ELISA. Briefly, microtiter plates are coated with purified uPA at 0.25 µg/ml in PBS, and then blocked with 5% bovine serum albumin in PBS. Dilutions of plasma from uPA-immunized mice are added to each well and incubated for 1-2 hours at 37° C. The plates are washed with PBS/Tween and then incubated with a goat-anti-human IgG Fc-specific polyclonal reagent conjugated to alkaline phosphatase for 1 hour at 37° C. After washing, the plates are developed with pNPP substrate (1 mg/ml), and analyzed at OD of 405-650. Preferably, mice which develop the highest titers will be used for fusions.

An ELISA assay as described above can also be used to screen for hybridomas that show positive reactivity with uPA antigen. Hybridomas that bind with high affinity to uPA will be subcloned and further characterized. One clone from each hybridoma, which retains the reactivity of the parent cells (by ELISA), can be chosen for making a 5-10 vial cell bank stored at −140° C., and for antibody purification.

To purify human anti-uPA antibodies, selected hybridomas can be grown in two-liter spinner-flasks for monoclonal antibody purification. Supernatants can be filtered and concentrated before affinity chromatography with protein A-sepharose (Pharmacia, Piscataway, N.J.). Eluted IgG can be checked by gel electrophoresis and high performance liquid chromatography to ensure purity. The buffer solution can be exchanged into PBS, and the concentration can be determined by $OD_{280}$ using 1.43 extinction coefficient. The monoclonal antibodies can be aliquoted and stored at −80° C.

To determine if the selected human anti-uPA monoclonal antibodies bind to unique epitopes, each antibody can be biotinylated using commercially available reagents (Pierce, Rockford, Ill.). Competition studies using unlabeled monoclonal antibodies and biotinylated monoclonal antibodies can be performed using uPA coated-ELISA plates as described above. Biotinylated MAb binding can be detected with a strep-avidin-alkaline phosphatase probe.

To determine the isotype of purified antibodies, isotype ELISAs can be performed. Wells of microtiter plates can be coated with 10 g/ml of anti-human Ig overnight at 4° C. After blocking with 5% BSA, the plates are reacted with 10 g/ml of monoclonal antibodies or purified isotype controls, at ambient temperature for two hours. The wells can then be reacted with either human IgG1 or human IgM-specific alkaline phosphatase-conjugated probes. Plates are developed and analyzed as described above.

In order to demonstrate binding of monoclonal antibodies to live cells expressing the uPA, flow cytometry can be used. Briefly, cell lines expressing uPA (grown under standard growth conditions) are mixed with various concentrations of monoclonal antibodies in PBS containing 0.1% Tween 80 and 20% mouse serum, and incubated at 37° C. for 1 hour. After washing, the cells are reacted with Fluorescein-labeled anti-human IgG antibody under the same conditions as the primary antibody staining. The samples can be analyzed by FACScan instrument using light and side scatter properties to gate on single cells. An alternative assay using fluorescence microscopy may be used (in addition to or instead of) the flow cytometry assay. Cells can be stained exactly as described above and examined by fluorescence microscopy. This method allows visualization of individual cells, but may have diminished sensitivity depending on the density of the antigen.

Anti-uPA human IgGs can be further tested for reactivity with uPA antigen by Western blotting. Briefly, cell extracts from cells expressing uPA can be prepared and subjected to sodium dodecyl sulfate (SDS) polyacrylamide gel electrophoresis. After electrophoresis, the separated antigens will be transferred to nitrocellulose membranes, blocked with 20% mouse serum, and probed with the monoclonal antibodies to be tested. Human IgG binding can be detected using anti-human IgG alkaline phosphatase and developed with BCIP/NBT substrate tablets (Sigma Chem. Co., St. Louis, Mo.).

Transgenic Nonhuman Animals which Generate Human Monoclonal Anti-uPA Antibodies

Human monoclonal antibodies directed against uPA polypeptides, such as uPA KD, can be generated using transgenic mice carrying parts of the human immune system rather than the mouse system. These transgenic mice, referred to herein as "HuMAb" mice, contain a human immunoglobulin gene miniloci that encodes unrearranged human heavy (μ and γ) and κ light chain immunoglobulin sequences, together with targeted mutations that inactivate the endogenous μ and κ chain loci (Lonberg, et al., *Nature* 368(6474):856-859 (1994)). Accordingly, the mice exhibit reduced expression of mouse IgM or κ, and in response to immunization, the introduced human heavy and light chain transgenes undergo class switching and somatic mutation to generate high affinity human IgGκ monoclonal antibodies (Lonberg, et al., *Nature* 368(6474):856-859 (1994); reviewed in Lonberg, *Handbook of Experimental Pharmacology* 113:49-101 (1994); Lonberg, and Huszar, *Intern. Rev. Immunol.* 13:65-93 (1995), and Harding, and Lonberg, *Ann. N.Y. Acad. Sci.* 764:536-546 (1995)). The preparation of HuMAb mice is described in detail below and in Taylor, et al., *Nucleic Acids Research* 20:6287-6295 (1992); Chen, J. et al., *International Immunology* 5: 647-656 (1993); Tuaillon, et al., *Proc. Natl. Acad. Sci. USA* 90:3720-3724 (1993); Choi, et al., *Nature Genetics* 4:117-123 (1993); Chen, et al. *EMBO J.* 12: 821-830 (1993); Tuaillon, et al., *J. Immunol.* 152:2912-2920 (1994); Lonberg et al., *Nature* 368: 6474 (1994): 856-859; Lonberg, *Handbook of Experimental Pharmacology* 113:49-101 (1994); Taylor, et al., *International Immunology* 6:579-591 (1994); Lonberg and Huszar, *Intern. Rev. Immunol.* 13:65-93 (1995); Harding and Lonberg, *Ann. N.Y. Acad. Sci* 764:536-546 (1995); Fishwild, et al., *Nature Biotechnology* 14:845-851 (1996), the contents of all of which are hereby incorporated by reference in their entirety. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay, and GenPharm International; U.S. Pat. No. 5,545,807 to Surani et al.; International Publication Nos. WO 98/24884, published on Jun. 11, 1998; WO 94/25585, published Nov. 10, 1994; WO 93/1227, published Jun. 24, 1993; WO 92/22645, published Dec. 23, 1992; WO 92/03918, published Mar. 19, 1992, the disclosures of all of which are hereby incorporated by reference in their entity. Alternatively, transgenic mice can be used to generate human anti-uPA antibodies.

To generate fully human monoclonal antibodies to uPA, HuMAb mice can be immunized with a purified or enriched preparation of uPA antigen and/or cells expressing uPA, as described by Lonberg, et al., *Nature* 368(6474):856-859 (1994); Fishwild, et al., *Nature Biotechnology* 14: 845-851 (1996) and WO 98/24884. Preferably, the mice will be 6-16 weeks of age upon the first infusion. For example, a purified or enriched preparation (5-20 μg) of uPA antigen (e.g., purified from uPA-expressing LNCaP cells) can be used to immunize the HuMAb mice intraperitoneally. In the event that immunizations using a purified or enriched preparation of uPA antigen do not result in antibodies, mice can also be immunized with cells expressing uPA, e.g., a tumor cell line, to promote immune responses.

Cumulative experience with various antigens has shown that the HuMAb transgenic mice respond well when initially immunized intraperitoneally (IP) with antigen in complete Freund's adjuvant, followed by every other week i.p. immunizations (up to a total of 6) with antigen in incomplete Freund's adjuvant. The immune response can be monitored over the course of the immunization protocol with plasma samples being obtained by retroorbital bleeds. The plasma can be screened by ELISA (as described below), and mice with sufficient titers of anti-uPA human immunoglobulin can be used for fusions. Mice can be boosted intravenously with antigen 3 days before sacrifice and removal of the spleen. It is expected that 2-3 fusions for each antigen may need to be performed. Several mice will be immunized for each antigen. For example, a total of twelve HuMAb mice of the HC07 and HC012 strains can be immunized.

In yet another aspect, the invention provides transgenic non-human animals, e.g., a transgenic mice, which are capable of expressing human monoclonal antibodies that specifically bind to uPA epitopes of the present invention. In a preferred embodiment, the transgenic non-human animals, e.g., the transgenic mice (HuMAb mice), have a genome comprising a human heavy chain transgene and a light chain transgene. In one embodiment, the transgenic non-human animals, e.g., the transgenic mice, have been immunized with a purified or enriched preparation of uPA antigen and/or cells expressing uPA. Preferably, the transgenic non-human animals, e.g., the transgenic mice, are capable of producing multiple isotypes of human monoclonal antibodies to uPA (e.g., IgG, IgA and/or IgE) by undergoing V-D-J recombination and isotype switching. Isotype switching may occur by, e.g., classical or non-classical isotype switching.

The design of a transgenic non-human animal that responds to foreign antigen stimulation with a heterologous antibody repertoire, requires that the heterologous immunoglobulin transgenes contain within the transgenic animal function correctly throughout the pathway of B-cell development. In a preferred embodiment, correct function of a heterologous heavy chain transgene includes isotype switching. Accordingly, the transgenes of the invention are constructed so as to produce isotype switching and one or more of the following: (1) high level and cell-type specific expression, (2) functional gene rearrangement, (3) activation of and response to allelic exclusion, (4) expression of a sufficient primary repertoire, (5) signal transduction, (6) somatic hypermutation, and (7) domination of the transgene antibody locus during the immune response.

Not all of the foregoing criteria need be met. For example, in those embodiments wherein the endogenous immunoglobulin loci of the transgenic animal are functionally disrupted, the transgene need not activate allelic exclusion. Further, in those embodiments wherein the transgene comprises a functionally rearranged heavy and/or light chain immunoglobulin gene, the second criteria of functional gene rearrangement is unnecessary, at least for that transgene which is already rearranged. For background on molecular immunology, see, *Fundamental Immunology*, 2nd ed. (1989), Paul William E., ed. Raven Press, N.Y., which is incorporated herein by reference.

In certain embodiments, the transgenic non-human animals used to generate the human monoclonal antibodies of the invention contain rearranged, unrearranged or a combination of rearranged and unrearranged heterologous immunoglobulin heavy and light chain transgenes in the germline of the transgenic animal. Each of the heavy chain transgenes comprises at least one $C_H$ gene. In addition, the heavy chain transgene may contain functional isotype switch sequences, which are capable of supporting isotype switching of a heterologous transgene encoding multiple $C_H$ genes in the B-cells of the transgenic animal. Such switch sequences may be those which occur naturally in the germline immunoglobulin locus from the species that serves as the source of the transgene $C_H$ genes, or such switch sequences may be derived from those which occur in the species that is to receive the transgene construct (the transgenic animal). For example, a human transgene construct that is used to produce a transgenic mouse may produce a higher frequency of isotype switching events if it incorporates switch sequences similar to those that occur naturally in the mouse heavy chain locus, as presumably the mouse switch sequences are optimized to function with the mouse switch recombinase enzyme system, whereas the human switch sequences are not. Switch sequences may be isolated and cloned by conventional cloning methods, or may be synthesized de novo from overlapping synthetic oligonucleotides designed on the basis of published sequence information relating to immunoglobulin switch region sequences (Mills, et al., *Nucl. Acids Res.* 15:7305-7316 (1991); Sideras, et al., *Intl. Immunol.* 1:631-642 (1989), which are incorporated herein by reference). For each of the foregoing transgenic animals, functionally rearranged heterologous heavy and light chain immunoglobulin transgenes are found in a significant fraction of the B-cells of the transgenic animal (at least 10 percent).

The transgenes used to generate the transgenic animals of the invention include a heavy chain transgene comprising DNA encoding at least one variable gene segment, one diversity gene segment, one joining gene segment and at least one constant region gene segment. The immunoglobulin light chain transgene comprises DNA encoding at least one variable gene segment, one joining gene segment and at least one constant region gene segment. The gene segments encoding the light and heavy chain gene segments are heterologous to the transgenic non-human animal in that they are derived from, or correspond to, DNA encoding immunoglobulin heavy and light chain gene segments from a species not consisting of the transgenic non-human animal. The transgene may, for example, be constructed such that the individual gene segments are unrearranged, i.e., not rearranged so as to encode a functional immunoglobulin light or heavy chain. Such unrearranged transgenes support recombination of the V, D, and J gene segments (functional rearrangement) and preferably support incorporation of all or a portion of a D region gene segment in the resultant rearranged immunoglobulin heavy chain within the transgenic non-human animal when exposed to uPA antigen.

Transgenes may also comprise an unrearranged "minilocus." Such transgenes typically comprise a substantial portion of the C, D, and J segments as well as a subset of the V gene segments. In such transgene constructs, the various regulatory sequences, e.g., promoters, enhancers, class switch regions, splice-donor and splice-acceptor sequences for RNA processing, recombination signals and the like, comprise corresponding sequences derived from the heterologous DNA. Such regulatory sequences may be incorporated into the transgene from the same or a related species of the non-human animal used in the invention. For example, human immunoglobulin gene segments may be combined in a transgene with a rodent immunoglobulin enhancer sequence for use in a transgenic mouse. Alternatively, synthetic regulatory sequences may be incorporated into the transgene, wherein such synthetic regulatory sequences are not homologous to a functional DNA sequence that is known to occur naturally in the genomes of mammals. Synthetic regulatory sequences are designed according to consensus rules, such as, for example, those specifying the permissible sequences of a splice-acceptor site or a promoter/enhancer motif. For example, a minilocus comprises a portion of the genomic immunoglobulin locus having at least one internal (i.e., not at a terminus of the portion) deletion of a non-essential DNA portion (e.g., intervening sequence; intron or portion thereof) as compared to the naturally-occurring germline Ig locus.

Transgenic animals may also be used to generate human antibodies to uPA containing at least one, typically 2-10, and sometimes 25-50 or more copies of the transgene described in Example 12 of WO 98/24884 (e.g., pHC1 or pHC2) bred with an animal containing a single copy of a light chain transgene described in Examples 5, 6, 8, or 14 of WO 98/24884, and the offspring bred with the $J_H$ deleted animal described in Example 10 of WO 98/24884, the contents of which are hereby expressly incorporated by reference. Animals are bred to homozygosity for each of these three traits. Such animals have the following genotype: a single copy (per haploid set of chromosomes) of a human heavy chain unrearranged minilocus (described in Example 12 of WO 98/24884), a single copy (per haploid set of chromosomes) of a rearranged human kappa light chain construct (described in Example 14 of WO 98/24884), and a deletion at each endogenous mouse heavy chain locus that removes all of the functional $J_H$ segments (described in Example 10 of WO 98/24884). Such animals are bred with mice that are homozygous for the deletion of the $J_H$ segments (Examples 10 of WO 98/24884) to produce offspring that are homozygous for the $J_H$ deletion and hemizygous for the human heavy and light chain constructs. The resultant animals are injected with antigens and used for production of human monoclonal antibodies against these antigens.

B cells isolated from such an animal are monospecific with regard to the human heavy and light chains because they contain only a single copy of each gene. Furthermore, they will be monospecific with regards to human or mouse heavy chains because both endogenous mouse heavy chain gene copies are nonfunctional by virtue of the deletion spanning the $J_H$ region introduced as described in Example 9 and 12 of WO 98/24884. Furthermore, a substantial fraction of the B cells will be monospecific with regards to the human or mouse light chains because expression of the single copy of the rearranged human kappa light chain gene will allelically and isotypically exclude the rearrangement of the endogenous mouse kappa and lambda chain genes in a significant fraction of B-cells.

The transgenic mouse of the preferred embodiment will exhibit immunoglobulin production with a significant repertoire, ideally substantially similar to that of a native mouse. Thus, for example, in embodiments where the endogenous Ig genes have been inactivated, the total immunoglobulin levels will range from about 0.1 to 10 mg/ml of serum, preferably 0.5 to 5 mg/ml, ideally at least about 1.0 mg/ml. When a transgene capable of effecting a switch to IgG from IgM has been introduced into the transgenic mouse, the adult mouse ratio of serum IgG to IgM is preferably about 10:1. The IgG to IgM ratio will be much lower in the immature mouse. In general, greater than about 10%, preferably 40 to 80% of the spleen and lymph node B cells express exclusively human IgG protein. The repertoire will ideally approximate that shown in a non-transgenic mouse, usually at least about 10% as high, preferably 25 to 50% or more. Generally, at least about a thousand different immunoglobulins (ideally IgG), preferably $10^4$ to $10^6$ or more, will be produced, depending primarily on the number of different V, J and D regions introduced into the mouse genome. These immunoglobulins will typically recognize about one-half or more of highly antigenic proteins, e.g., *staphylococcus* protein A. Typically, the immunoglobulins will exhibit an affinity for preselected antigens of at least about $10^7$ $M^{-1}$, preferably at least about $10^9$ M$^{-1}$, more preferably at least about $10^{10}$ M$^{-1}$, $10^{11}$ M$^{-1}$, $10^{12}$ M$^{-1}$, or greater, e.g., up to $10^{13}$ M$^{-1}$ or greater.

In some embodiments, it may be preferable to generate mice with predetermined repertoires to limit the selection of V genes represented in the antibody response to a predetermined antigen type. A heavy chain transgene having a predetermined repertoire may comprise, for example, human $V_H$ genes which are preferentially used in antibody responses to the predetermined antigen type in humans. Alternatively, some $V_H$ genes may be excluded from a defined repertoire for various reasons (e.g., have a low likelihood of encoding high affinity V regions for the predetermined antigen; have a low propensity to undergo somatic mutation and affinity sharpening; or are immunogenic to certain humans). Thus, prior to rearrangement of a transgene containing various heavy or light chain gene segments, such gene segments may be readily identified, e.g., by hybridization or DNA sequencing, as being from a species of organism other than the transgenic animal.

The transgenic mice of the present invention can be immunized with a purified or enriched preparation of uPA antigen and/or cells expressing uPA as described previously. The mice will produce B cells which undergo class-switching via intratransgene switch recombination (cis-switching) and express immunoglobulins reactive with uPA. The immunoglobulins can be human sequence antibodies, wherein the heavy and light chain polypeptides are encoded by human transgene sequences, which may include sequences derived by somatic mutation and V region recombinatorial joints, as well as germline-encoded sequences; these human sequence immunoglobulins can be referred to as being substantially identical to a polypeptide sequence encoded by a human $V_L$ or $V_H$ gene segment and a human $J_L$ or $J_L$ segment, even though other non-germline sequences may be present as a result of somatic mutation and differential V-J and V-D-J recombination joints. With respect to such human sequence antibodies, the variable regions of each chain are typically at least 80 percent encoded by human germline V, J, and, in the case of heavy chains, D, gene segments; frequently at least 85 percent of the variable regions are encoded by human germline sequences present on the transgene; often 90 or 95 percent or more of the variable region sequences are encoded by human germline sequences present on the transgene. However, since non-germline sequences are introduced by somatic mutation and VJ and VDJ joining, the human sequence antibodies will frequently have some variable region sequences (and less frequently constant region sequences) which are not encoded by human V, D, or J gene segments as found in the human transgene(s) in the germline of the mice. Typically, such non-germline sequences (or individual nucleotide positions) will cluster in or near CDRs, or in regions where somatic mutations are known to cluster.

The human sequence antibodies which bind to the predetermined antigen can result from isotype switching, such that human antibodies comprising a human sequence γ chain (such as γ1, γ2a, γ2B, or γ3) and a human sequence light chain (such as the kappa light chain) are produced. Such isotype-switched human sequence antibodies often contain one or more somatic mutation(s), typically in the variable region and often in or within about 10 residues of a CDR) as a result of affinity maturation and selection of B cells by antigen, particularly subsequent to secondary (or subsequent) antigen challenge.

Once the mouse germline has been engineered to contain a functional YAC having an expanded V segment repertoire, substantially not present in the human Ig transgene containing the J and C gene segments, the trait can be propagated and bred into other genetic backgrounds, including backgrounds where the functional YAC having an expanded V segment repertoire is bred into a mouse germline having a different human Ig transgene. Multiple functional YACs having an expanded V segment repertoire may be bred into a germline to work with a human Ig transgene (or multiple human Ig transgenes). Although referred to herein as YAC transgenes, such transgenes when integrated into the genome may substantially lack yeast sequences, such as sequences required for autonomous replication in yeast; such sequences may optionally be removed by genetic engineering (e.g., restriction digestion and pulsed-field gel electrophoresis or other suitable method) after replication in yeast in no longer necessary (i.e., prior to introduction into a mouse ES cell or mouse prozygote). Methods of propagating the trait of human sequence immunoglobulin expression, include breeding a transgenic mouse having the human Ig transgene(s), and optionally also having a functional YAC having an expanded V segment repertoire. Both $V_H$ and $V_L$ gene segments may be present on the YAC. The transgenic mouse may be bred into any background desired by the practitioner, including backgrounds harboring other human transgenes, including human Ig transgenes and/or transgenes encoding other human lymphocyte proteins. The invention also provides a high affinity human sequence immunoglobulin produced by a transgenic mouse having an expanded V region repertoire YAC transgene. Although the foregoing describes a preferred embodiment of the transgenic animal of the invention, other embodiments are contemplated which include (1) transgenic animals containing an unrearranged heavy and rearranged light immunoglobulin transgene; (2) transgenic animals containing an unrearranged heavy and unrearranged light immunoglobulin transgene; (3) transgenic animals containing rearranged heavy and an unrearranged light immunoglobulin transgene; and (4) transgenic animals containing rearranged heavy and rearranged light immunoglobulin transgenes.

Bispecific Multispecific Molecules which Bind to uPA

In yet another embodiment of the invention, human monoclonal antibodies to uPA, or antigen-binding regions thereof, can be derivatized or linked to another functional molecule, e.g., another peptide or protein (e.g., an Fab' fragment) to generate a bispecific or multispecific molecule which binds to multiple binding sites or target epitopes. For example, an antibody or antigen-binding region of the invention can be functionally linked (e.g., by chemical coupling, genetic fusion, noncovalent association or otherwise) to one or more other binding molecules, such as another antibody, antibody fragment, peptide or binding mimetic.

Accordingly, the present invention includes bispecific and multispecific molecules comprising at least one first binding specificity for uPA and a second binding specificity for a second target epitope. In a particular embodiment of the invention, the second target epitope is an Fc receptor, e.g., human FcγRI (CD64) or a human Fcα receptor (CD89). Therefore, the invention includes bispecific and multispecific molecules capable of binding both to FcγR, FcαR or FcεCR expressing effector cells (e.g., monocytes, macrophages or polymorphonuclear cells (PMNs)), and to target cells expressing uPA. These bispecific and multispecific molecules target uPA expressing cells to effector cell and, like the human monoclonal antibodies of the invention, trigger Fc receptor-mediated effector cell activities, such as phagocytosis of a uPA expressing cells, antibody dependent cell-mediated cytotoxicity (ADCC), cytokine release, or generation of superoxide anion.

Bispecific and multispecific molecules of the invention can further include a third binding specificity, in addition to an anti-Fc binding specificity and an anti-uPA binding specificity. In one embodiment, the third binding specificity is an anti-enhancement factor (EF) portion, e.g., a molecule which binds to a surface protein involved in cytotoxic activity and thereby increases the immune response against the target cell. The "anti-enhancement factor portion" can be an antibody, functional antibody fragment or a ligand that binds to a given molecule, e.g., an antigen or a receptor, and thereby results in an enhancement of the effect of the binding determinants for the Fc receptor or target cell antigen. The "anti-enhancement factor portion" can bind an Fc receptor or a target cell antigen. Alternatively, the anti-enhancement factor portion can bind to an entity that is different from the entity to which the first and second binding specificities bind. For example, the anti-enhancement factor portion can bind a cytotoxic T-cell (e.g., via CD2, CD3, CD8, CD28, CD4, CD40, ICAM-1 or other immune cell that results in an increased immune response against the target cell).

In one embodiment, the bispecific and multispecific molecules of the invention comprise as a binding specificity at least one antibody, or an antibody fragment thereof, including, e.g., an Fab, Fab', F(ab')$_2$, Fv, or a single chain Fv. The antibody may also be a light chain or heavy chain dimer, or any minimal fragment thereof such as a Fv or a single chain construct as described in Ladner et al. U.S. Pat. No. 4,946,778, the contents of which is expressly incorporated by reference.

In another embodiment, bispecific and multispecific molecules of the invention comprise a binding specificity for an FcαR or an FcγR present on the surface of an effector cell, and a second binding specificity for a target cell antigen, e.g., uPA.

In another embodiment, the binding specificity for an Fc receptor is provided by a human monoclonal antibody, the binding of which is not blocked by human immunoglobulin G (IgG). As used herein, the term "IgG receptor" refers to any of the eight γ-chain genes located on chromosome 1. These genes encode a total of twelve transmembrane or soluble receptor isoforms which are grouped into three Fcγ receptor classes: FcγRI (CD64), FcγRII(CD32), and FcγRIII (CD16). In one preferred embodiment, the Fcγ receptor a human high affinity FcγRI. The human FcγRI is a 72 kDa molecule, which shows high affinity for monomeric IgG ($10^8$-$10^9$ M$^{-1}$).

The production and characterization of these preferred monoclonal antibodies are described by Fanger et al. in PCT application WO 88/00052 and in U.S. Pat. No. 4,954,617, the teachings of which are fully incorporated by reference herein. These antibodies bind to an epitope of FcγRI, FcγRII or FcγRIII at a site which is distinct from the Fcγ binding site of the receptor and, thus, their binding is not blocked substantially by physiological levels of IgG. Specific anti-FcγRI antibodies useful in this invention are MAb 22, MAb 32, MAb 44, MAb 62 and MAb 197. The hybridoma producing MAb 32 is available from the American Type Culture Collection, ATCC Accession No. HB9469. Anti-FcγRI MAb 22, F(ab')$_2$ fragments of MAb 22, and can be obtained from Medarex, Inc. (Annandale, N.J.). In other embodiments, the anti-Fcγ receptor antibody is a humanized form of monoclonal antibody 22 (H22). The production and characterization of the H22 antibody is described in Graziano, et al., *J. Immunol.* 155(10): 4996-5002 (1995) and PCT/US93/10384. The H22 antibody producing cell line was deposited at the American Type Culture Collection on Nov. 4, 1992 under the designation HA022CL1 and has the accession no. CRL 11177.

In still other preferred embodiments, the binding specificity for an Fc receptor is provided by an antibody that binds to a human IgA receptor, e.g., an Fc-alpha receptor (FcαRI (CD89)), the binding of which is preferably not blocked by human immunoglobulin A (IgA). The term "IgA receptor" is intended to include the gene product of one α-gene (FcαRI) located on chromosome 19. This gene is known to encode several alternatively spliced transmembrane isoforms of 55 to 110 kDa. FcαRI (CD89) is constitutively expressed on monocytes/macrophages, eosinophilic and neutrophilic granulocytes, but not on non-effector cell populations. FcαRI has medium affinity (approximately equal to $5 \times 10^7$ M$^{-1}$) for both IgA1 and IgA2, which is increased upon exposure to cytokines such as G-CSF or GM-CSF (Morton et al., *Critical Reviews in Immunology* 16:423-440 (1996)). Four FcαRI-specific monoclonal antibodies, identified as A3, A59, A62 and A77, which bind FcαRI outside the IgA ligand binding domain, have been described, for example, by Monteiro, et al., *J. Immunol.* 148:1764 (1992).

In another embodiment, the antibodies of the present invention may take the form of a scFv fragment fused directly to the Fc portion (CH2 & CH3) of the human IgG1 isotype (referred to herein as a scFv-Fc construct). Construction of scFv-Fc fusions are disclosed, for example, by Fredericks, et al., *Protein Engineering Design and Selection* 17:95-106 (2003), Powers, et al., *J. Immunological Methods* 251:123-135 (2001), Shu, et al., *PNAS* 90:7995-7999 (1993), and Hayden, et al., *Therapeutic Immunology* 1:3-15 (1994).

FcαRI and FcγRI are preferred trigger receptors for use in the invention because they are (1) expressed primarily on immune effector cells, e.g., monocytes, PMNs, macrophages and dendritic cells; (2) expressed at high levels (e.g., 5,000-100,000 per cell); (3) mediators of cytotoxic activities (e.g., ADCC, phagocytosis); (4) mediate enhanced antigen presentation of antigens, including self-antigens, targeted to them.

In other embodiments, bispecific and multispecific molecules of the invention further comprise a binding specificity which recognizes, e.g., binds to, a target cell antigen, e.g., uPA. In one particular embodiment, the binding specificity is provided by a human monoclonal antibody of the present invention.

While human monoclonal antibodies are preferred, other antibodies which can be employed in the bispecific or multispecific molecules of the invention are murine, chimeric and humanized monoclonal antibodies.

Chimeric mouse-human monoclonal antibodies (i.e., chimeric antibodies) can be produced by recombinant DNA techniques known in the art. For example, a gene encoding the Fc constant region of a murine (or other species) monoclonal antibody molecule is digested with restriction enzymes to remove the region encoding the murine Fc, and the equivalent portion of a gene encoding a human Fc constant region is substituted. (see Robinson et al., International Patent Publication PCT/US86/02269; Akira, et al., European Patent Application 184,187; Taniguchi, M., European Patent Application 171,496; Morrison et al., European Patent Application 173,494; Neuberger et al., International Application WO 86/01533; Cabilly et al. U.S. Pat. No. 4,816,567; Cabilly et al., European Patent Application 125,023; Better et al., *Science* 240:1041-1043 (1988); Liu et al., *PNAS* 84:3439-3443 (1987); Liu et al., *J. Immunol.* 139:3521-3526 (1987); Sun et al., *PNAS* 84:214-218 (1987); Nishimura et al., *Canc. Res.* 47:999-1005 (1987); Wood et al., *Nature* 314:446-449 (1985); and Shaw et al., *J Natl Cancer Inst.* 80:1553-1559 (1988).

The chimeric antibody can be further humanized by replacing sequences of the Fv variable region which are not directly involved in antigen binding with equivalent sequences from human Fv variable regions. General reviews of humanized chimeric antibodies are provided by Morrison, *Science* 229:

1202-1207 (1985) and by Oi et al., *BioTechniques* 4:214 (1986). Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, may be obtained from 7E3, an anti-GPII$_b$III$_a$ antibody producing hybridoma. The recombinant DNA encoding the chimeric antibody, or fragment thereof, can then be cloned into an appropriate expression vector. Suitable humanized antibodies can alternatively be produced by CDR substitution U.S. Pat. No. 5,225,539; Jones et al., *Nature* 321:552-525 (1986); Verhoeyan et al., *Science* 239:1534 (1988); and Beidler et al., *J. Immunol.* 141:4053-4060 (1988).

The CDRs of a particular human antibody may be replaced with at least a portion of a non-human CDR or only some of the CDRs may be replaced with non-human CDRs. It is only necessary to replace the number of CDRs required for binding of the humanized antibody to the Fc receptor.

An antibody can be humanized by any method, which is capable of replacing at least a portion of a CDR of a human antibody with a CDR derived from a non-human antibody. Winter describes a method which may be used to prepare the humanized antibodies of the present invention (UK Patent Application GB 2188638A, filed on Mar. 26, 1987), the contents of which is expressly incorporated by reference. The human CDRs may be replaced with non-human CDRs using oligonucleotide site-directed mutagenesis as described in International Application WO 94/10332 entitled, Humanized Antibodies to Fc Receptors for Immunoglobulin G on Human Mononuclear Phagocytes.

Also within the scope of the invention are chimeric and humanized antibodies in which specific amino acids have been substituted, deleted or added. In particular, preferred humanized antibodies have amino acid substitutions in the framework region, such as to improve binding to the antigen. For example, in a humanized antibody having mouse CDRs, amino acids located in the human framework region can be replaced with the amino acids located at the corresponding positions in the mouse antibody. Such substitutions are known to improve binding of humanized antibodies to the antigen in some instances. Antibodies in which amino acids have been added, deleted, or substituted are referred to herein as modified antibodies or altered antibodies.

The term modified antibody is also intended to include antibodies, such as monoclonal antibodies, chimeric antibodies, and humanized antibodies which have been modified by, e.g., deleting, adding, or substituting portions of the antibody. For example, an antibody can be modified by deleting the constant region and replacing it with a constant region meant to increase half-life, e.g., serum half-life, stability or affinity of the antibody. Any modification is within the scope of the invention so long as the bispecific and multispecific molecule has at least one antigen binding region specific for an FcγR and triggers at least one effector function.

Bispecific and multispecific molecules of the present invention can be made using chemical techniques (see e.g., Kranz et al., *Proc. Natl. Acad. Sci. USA* 78:5807 (1981), "polydoma" techniques (See U.S. Pat. No. 4,474,893, to Reading), or recombinant DNA techniques.

In particular, bispecific and multispecific molecules of the present invention can be prepared by conjugating the constituent binding specificities, e.g., the anti-FcR and anti-uPA binding specificities, using methods known in the art and described in the examples provided herein. For example, each binding specificity of the bispecific and multispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-5-acetyl-thioacetate (SATA), 5,5'-dithiobis(2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl)cyclohaxane-1-carboxylate (sulfo-SMCC) (see e.g., Karpovsky et al. *J. Exp. Med.* 160: 1686 (1984); Liu, et al., *Proc. Natl. Acad. Sci. USA* 82:8648 (1985)). Other methods include those described by Paulus (*Behring Ins. Mitt.* No. 78, 118-132 (1985)); Brennan et al., *Science* 229:81-83 (1985), and Glennie et al., *J. Immunol.* 139: 2367-2375 (1987). Preferred conjugating agents are SATA and sulfo-SMCC, both available from Pierce Chemical Co. (Rockford, Ill.).

Any "linker" group is optional. When present, its chemical structure is not critical, since it serves primarily as a spacer. The linker is preferably made up of amino acids linked together by peptide bonds. Thus, in preferred embodiments, the linker is made up of from 1 to 20 amino acids linked by peptide bonds, wherein the amino acids are selected from the 20 naturally occurring amino acids. One or more of these amino acids may be glycosylated, as is well understood by those in the art. In a more preferred embodiment, the 1 to 20 amino acids are selected from glycine, alanine, proline, asparagine, glutamine, and lysine. Even more preferably, a linker is made up of a majority of amino acids that are sterically unhindered, such as glycine and alanine. Thus, preferred linkers are polyglycines (particularly (Gly)$_5$, (Gly)$_8$), poly(Gly-Ala), and polyalanines. Combinations of Gly and Ala are also preferred.

Non-peptide linkers are also possible. For example, alkyl linkers such as —NH—(CH$_2$)s-C(O)—, wherein s=2-20 can be used. These alkyl linkers may further be substituted by any non-sterically hindering group such as lower alkyl (e.g., C1-C6) lower acyl, halogen (e.g., Cl, Br), CN, NH$_2$, phenyl, etc. An exemplary non-peptide linker is a PEG linker, and has a molecular weight of 100 to 5000 kDa, preferably 100 to 500 kDa. The peptide linkers may be altered to form derivatives in the same manner as described above.

When the binding specificities are antibodies (e.g., two humanized antibodies), they can be conjugated via sulfhydryl bonding of the C-terminus hinge regions of the two heavy chains. In a particularly preferred embodiment, the hinge region is modified to contain an odd number of sulfhydryl residues, preferably one, prior to conjugation.

Alternatively, both binding specificities can be encoded in the same vector and expressed and assembled in the same host cell. This method is particularly useful where the bispecific and multispecific molecule is a MAb×MAb, Mab×Fab, Fab×F(ab')$_2$ or ligand×Fab fusion protein. A bispecific and multispecific molecule of the invention, e.g., a bispecific molecule can be a single chain molecule, such as a single chain bispecific antibody, a single chain bispecific molecule comprising one single chain antibody and a binding determinant, or a single chain bispecific molecule comprising two binding determinants. Bispecific and multispecific molecules can also be single chain molecules or may comprise at least two single chain molecules. Methods for preparing bi- and multispecific molecules are described for example in U.S. Pat. Nos. 5,260,203; 5,455,030; 4,881,175; 5,132,405; 5,091,513; 5,476,786; 5,013,653; 5,258,498; and 5,482,858.

Binding of the bispecific and multispecific molecules to their specific targets can be confirmed by enzyme-linked immunosorbent assay (ELISA), a radioimmunoassay (RIA), FACS analysis, a bioassay (e.g., growth inhibition), or a Western Blot Assay. Each of these assays generally detects the presence of protein-antibody complexes of particular interest by employing a labeled reagent (e.g., an antibody) specific for the complex of interest. For example, the FcR-antibody complexes can be detected using e.g., an enzyme-linked antibody or antibody fragment which recognizes and specifically binds to the antibody-FcR complexes. Alternatively, the complexes can be detected using any of a variety of other immunoassays. For example, the antibody can be radioactively labeled and used in a radioimmunoassay (RIA) (see, for example, Weintraub, B., *Principles of Radioimmunoassays*, Seventh Training Course on Radioligand Assay Techniques, The Endocrine Society, March, 1986, which is incorporated by reference herein). The radioactive isotope can be detected by such means as the use of a γ counter or a scintillation counter or by autoradiography.

In the antibodies and antigen-binding regions thereof may also be combined with a vehicle for targeted delivery to a specified location.

In one embodiment, this invention provides antibodies, or antigen-binding regions thereof, that are attached to at least one vehicle (F1, F2) through the N-terminus, C-terminus or a side chain of one of the amino acid residues of the peptide(s). Multiple vehicles may also be used; e.g., Fc's at each terminus or an Fc at a terminus and a PEG group at the other terminus or a side chain.

An Fc domain is one preferred vehicle. The Fc domain may be fused to the N or C termini of the peptides or at both the N and C termini.

As noted above, Fc variants are suitable vehicles within the scope of this invention. A native Fc may be extensively modified to form an Fc variant in accordance with this invention, provided binding to the salvage receptor is maintained. See, for example WO 97/34631 and WO 96/32478. In such Fc variants, one may remove one or more sites of a native Fc that provide structural features or functional activity not required by the fusion molecules of this invention. One may remove these sites by, for example, substituting or deleting residues, inserting residues into the site, or truncating portions containing the site. The inserted or substituted residues may also be altered amino acids, such as peptidomimetics or D-amino acids. Fc variants may be desirable for a number of reasons, several of which are described below. Exemplary Fc variants include molecules and sequences in which:

1. Sites involved in disulfide bond formation are removed. Such removal may avoid reaction with other cysteine-containing proteins present in the host cell used to produce the molecules of the invention. For this purpose, the cysteine-containing segment at the N-terminus may be truncated or cysteine residues may be deleted or substituted with other amino acids (e.g., alanyl, seryl). Even when cysteine residues are removed, the single chain Fc domains can still form a dimeric Fc domain that is held together non-covalently.
2. A native Fc is modified to make it more compatible with a selected host cell. For example, one may remove the PA sequence near the N-terminus of a typical native Fc, which may be recognized by a digestive enzyme in *E. coli* such as proline iminopeptidase. One may also add an N-terminal methionyl residue, especially when the molecule is expressed recombinantly in a bacterial cell such as *E. coli*.
3. A portion of the N-terminus of a native Fc is removed to prevent N-terminal heterogeneity when expressed in a selected host cell. For this purpose, one may delete any of the first 20 amino acid residues at the N-terminus, particularly those at positions 1, 2, 3, 4 and 5.
4. One or more glycosylation sites are removed. Residues that are typically glycosylated (e.g., asparagine) may confer cytolytic response. Such residues may be deleted or substituted with unglycosylated residues (e.g., alanine).
5. Sites involved in interaction with complement, such as the C1q binding site, are removed. For example, one may delete or substitute the EKK sequence of human IgG1. Complement recruitment may not be advantageous for the molecules of this invention and so may be avoided with such an Fc variant.
6. Sites are removed that affect binding to Fc receptors other than a salvage receptor. A native Fc may have sites for interaction with certain white blood cells that are not required for the fusion molecules of the present invention and so may be removed.
7. The ADCC site is removed. ADCC sites are known in the art. See, for example, *Molec. Immunol.* 29(5):633-9 (1992) with regard to ADCC sites in IgG1. These sites, as well, are not required for the fusion molecules of the present invention and so may be removed.
8. When the native Fc is derived from a non-human antibody, the native Fc may be humanized. Typically, to humanize a native Fc, one will substitute selected residues in the non-human native Fc with residues that are normally found in human native Fc. Techniques for antibody humanization are well known in the art.

An alternative vehicle would be a protein, polypeptide, peptide, antibody, antibody fragment, or small molecule (e.g., a peptidomimetic compound) capable of binding to a salvage receptor. For example, one could use as a vehicle a polypeptide as described in U.S. Pat. No. 5,739,277, issued Apr. 14, 1998 to Presta et al. Peptides could also be selected by phage display for binding to the FcRn salvage receptor. Such salvage receptor-binding compounds are also included within the meaning of "vehicle" and are within the scope of this invention. Such vehicles should be selected for increased half-life (e.g., by avoiding sequences recognized by proteases) and decreased immunogenicity (e.g., by favoring non-immunogenic sequences, as discovered in antibody humanization).

As noted above, polymer vehicles may also be used for F1 and F2. Various means for attaching chemical moieties useful as vehicles are currently available, see, e.g., Patent Cooperation Treaty ("PCT") International Publication No. WO 96/11953, entitled "N-Terminally Chemically Modified Protein Compositions and Methods," herein incorporated by reference in its entirety. This PCT publication discloses, among other things, the selective attachment of water soluble polymers to the N-terminus of proteins.

A preferred polymer vehicle is polyethylene glycol (PEG). The PEG group may be of any convenient molecular weight and may be linear or branched. The average molecular weight of the PEG will preferably range from about 2 kiloDalton ("kDa") to about 100 kDa, more preferably from about 5 kDa to about 50 kDa, most preferably from about 5 kDa to about 10 kDa. The PEG groups will generally be attached to the compounds of the invention via acylation or reductive alkylation through a reactive group on the PEG moiety (e.g., an aldehyde, amino, thiol, or ester group) to a reactive group on the inventive compound (e.g., an aldehyde, amino, or ester group).

A useful strategy for the PEGylation of synthetic peptides consists of combining, through forming a conjugate linkage in solution, a peptide and a PEG moiety, each bearing a special functionality that is mutually reactive toward the other. The peptides can be easily prepared with conventional solid phase synthesis as known in the art. The peptides are "preactivated" with an appropriate functional group at a specific site. The precursors are purified and fully characterized prior to reacting with the PEG moiety. Ligation of the peptide with PEG usually takes place in aqueous phase and can be easily monitored by reverse phase analytical HPLC. The PEGylated peptides can be easily purified by preparative HPLC and characterized by analytical HPLC, amino acid analysis and laser desorption mass spectrometry.

Polysaccharide polymers are another type of water soluble polymer which may be used for protein modification. Dextrans are polysaccharide polymers comprised of individual subunits of glucose predominantly linked by al-6 linkages. The dextran itself is available in many molecular weight ranges, and is readily available in molecular weights from about 1 kDa to about 70 kDa. Dextran is a suitable water-soluble polymer for use in the present invention as a vehicle by itself or in combination with another vehicle (e.g., Fc). See, for example, WO 96/11953 and WO 96/05309. The use of dextran conjugated to therapeutic or diagnostic immunoglobulins has been reported; see, for example, European Patent Publication No. 0 315 456, which is hereby incorporated by reference. Dextran of about 1 kDa to about 20 kDa is preferred when dextran is used as a vehicle in accordance with the present invention.

Antibody Conjugates/Immunotoxins

In another aspect, the present invention features a human anti-uPA monoclonal antibody, or a fragment thereof, conjugated to a therapeutic moiety, such as a cytotoxin, a drug or a radioisotope. When conjugated to a cytotoxin, these antibody conjugates are referred to as "immunotoxins." A cytotoxin or cytotoxic agent includes any agent that is detrimental to (e.g., kills) cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). Other examples of therapeutic cytotoxins that can be conjugated to an antibody of the invention include calicheamicin and duocarmycin. An antibody of the present invention can be conjugated to a radioisotope, e.g., radioactive iodine, to generate cytotoxic radiopharmaceuticals for treating a uPA-related disorder, such as a cancer.

The antibody conjugates of the invention can be used to modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, pseudomonas exotoxin, or diphtheria toxin; a protein such as tumor necrosis factor or interferon-gamma.; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", *Immunol. Rev.* 62:119-58 (1982).

Pharmaceutical Compositions

Pharmaceutical compositions of anti-uPA antibodies are within the scope of the present invention. Pharmaceutical compositions comprising antibodies are described in detail in, for example, U.S. Pat. No. 6,171,586, to Lam et al., issued Jan. 9, 2001. Such compositions comprise a therapeutically or prophylactically effective amount of an antibody, or a fragment, variant, derivative or fusion thereof as described herein, in admixture with a pharmaceutically acceptable carrier and/or a pharmaceutically acceptable salt. In a preferred embodiment, pharmaceutical compositions comprise antibodies that bind uPA epitopes that activate uPA activity in admixture with a pharmaceutically acceptable carrier and/or a pharmaceutically acceptable salt. Typically, the specific binding agents will be sufficiently purified for administration to an animal.

Pharmaceutically Acceptable Carriers

As used herein, "pharmaceutically acceptable carrier" includes any and all solvents, dispersion media, coatings, antibacterial and antifungal agents, isotonic and absorption delaying agents, and the like that are physiologically compatible. In particular embodiments, the carrier is suitable for intravenous, intramuscular, subcutaneous, parenteral, spinal or epidermal administration (e.g., by injection or infusion). Depending on the route of administration, the active compound, i.e., antibody, bispecific and multispecific molecule, may be coated in a material to protect the compound from the action of acids and other natural conditions that may inactivate the compound. In another particular embodiment, the pharmaceutical compositions are formulated with a carrier that is pharmaceutically acceptable in humans.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

A "pharmaceutically acceptable salt" refers to a salt that retains the desired biological activity of the parent compound and does not impart any undesired toxicological effects (see e.g., Berge, et al., *J. Pharm. Sci.* 66:1-19 (1977)). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

The pharmaceutical compositions of the present invention may contain formulation materials for modifying, maintaining or preserving, for example, the pH, osmolarity, viscosity, clarity, color, isotonicity, odor, sterility, stability, rate of dissolution or release, adsorption or penetration of the composition. Suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates, other organic acids); bulking agents (such as mannitol or glycine), chelating agents [such as ethylenediamine tetraacetic acid (EDTA)]; complexing agents (such as caffeine, polyvinylpyrrolidone, beta-cyclodextrin or hydroxypropyl-beta-cyclodextrin); fillers; monosaccharides; disaccharides and other carbohydrates (such as glucose, mannose, or dextrins); proteins (such as serum albumin, gelatin or immunoglobulins); coloring; flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (sucrose or sorbitol); tonicity enhancing agents (such as alkali metal halides (preferably sodium or potassium chloride, mannitol sorbitol); delivery vehicles; diluents; excipients and/or pharmaceutical adjuvants. (Remington's Pharmaceutical Sciences, 18th Edition, A. R. Gennaro, ed., Mack Publishing Company, 1990).

The optimal pharmaceutical composition will be determined by one skilled in the art depending upon, for example, the intended route of administration, delivery format, and desired dosage. See for example, Remington's Pharmaceutical Sciences, supra. Such compositions may influence the physical state, stability, rate of in vivo release, and rate of in vivo clearance of the specific antibody.

The primary vehicle or carrier in a pharmaceutical composition may be either aqueous or non-aqueous in nature. For example, a suitable vehicle or carrier may be water for injection, physiological saline solution or artificial cerebrospinal fluid, possibly supplemented with other materials common in compositions for parenteral administration. Neutral buffered saline or saline mixed with serum albumin are further exemplary vehicles. Other exemplary pharmaceutical compositions comprise Tris buffer of about pH 7.0-8.5, or acetate buffer of about pH 4.0-5.5, which may further include sorbitol or a suitable substitute therefore. In one embodiment of the present invention, binding agent compositions may be prepared for storage by mixing the selected composition having the desired degree of purity with optional formulation agents (Remington's Pharmaceutical Sciences, supra) in the form of a lyophilized cake or an aqueous solution. Further, the binding agent product may be formulated as a lyophilizate using appropriate excipients such as sucrose.

The pharmaceutical compositions can be selected for parenteral delivery. Alternatively, the compositions may be selected for inhalation or for enteral delivery such as orally, aurally, opthalmically, rectally, or vaginally. The preparation of such pharmaceutically acceptable compositions is within the skill of the art.

The formulation components are present in concentrations that are acceptable to the site of administration. For example, buffers are used to maintain the composition at physiological pH or at slightly lower pH, typically within a pH range of from about 5 to about 8.

When the compounds of the present invention are administered as pharmaceuticals, to humans and animals, they can be given alone or as a pharmaceutical composition containing, for example, 0.01 to 99.5% (more preferably, 0.1 to 90%) of active ingredient in combination with a pharmaceutically acceptable carrier. By way of example, the pharmaceutical compositions of the present invention may contain an anti-uPA antibody or antigen-binding region thereof in a concentration of from about 1 mg/ml to about 30 mg/ml, or alternatively from about 5 mg/ml to about 30 mg/ml.

In certain embodiments, the human monoclonal antibodies of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., Ranade, *J. Clin. Pharmacol.* 29:685 (1989)). Exemplary targeting moieties include folate or biotin (see, e.g., U.S. Pat. No. 5,416,016 to Low et al.); mannosides (Umezawa et al., *Biochem. Biophys. Res. Commun.* 153:1038 (1988); antibodies (P. G. Bloeman et al., *FEBS Lett.* 357:140 (1995); M. Owais et al., *Antimicrob. Agents Chemother.* 39:180 (1995); surfactant protein A receptor (Briscoe et al., *Am. J. Physiol.* 1233:134 (1995), different species of which may comprise the formulations of the inventions, as well as components of the invented molecules; p120 (Schreier et al., *J. Biol. Chem.* 269:9090 (1994); see also, Keinanen and Laukkanen, *FEBS Lett.* 346:123 (1994); Killion and Fidler, *Immunomethods* 4:273 (1994). In one embodiment of the invention, the therapeutic compounds of the invention are formulated in liposomes; in a more preferred embodiment, the liposomes include a targeting moiety. In a most preferred embodiment, the therapeutic compounds in the liposomes are delivered by bolus injection to a site proximal to the tumor or infection. The composition must be fluid to the extent that easy syringability exists. It must be stable under the conditions of manufacture and storage and must be preserved against the contaminating action of microorganisms such as bacteria and fungi.

Therapeutically Effective Dosages

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art. A "therapeutically effective dosage" preferably inhibits tumor growth by at least about 20%, more preferably by at least about 40%, even more preferably by at least about 60%, and still more preferably by at least about 80% relative to untreated subjects. The ability of a compound to inhibit cancer can be evaluated in an animal model system predictive of efficacy in human tumors. Alternatively, this property of a composition can be evaluated by examining the ability of the compound to inhibit, such inhibition in vitro by assays known to the skilled practitioner. A therapeutically effective amount of a therapeutic compound can decrease tumor size, or otherwise ameliorate symptoms in a subject. One of ordinary skill in the art would be able to determine such amounts based on such factors as the subject's size, the severity of the subject's symptoms, and the particular composition or route of administration selected.

An effective amount of a pharmaceutical composition to be employed therapeutically will depend, for example, upon the therapeutic context and objectives. One skilled in the art will appreciate that the appropriate dosage levels for treatment will thus vary depending, in part, upon the molecule delivered, the indication for which the antibody or antigen-binding region is being used, the route of administration, and the size (body weight, body surface or organ size) and condition (the age and general health) of the patient. Accordingly, the clinician may titer the dosage and modify the route of administration to obtain the optimal therapeutic effect.

A preferred anti-uPA antibody or antigen-binding region thereof has the ability to substantially bind to uPA in solution at concentrations of less than 1 uM, preferably less than 0.1 uM, and more preferably less than 0.01 uM. By "substantially" is meant that at least a 50 percent reduction in endothelial cell proliferation and migration is observed by modulation in the presence of the an anti-uPA antibody or antigen-binding region thereof, and at 50% reduction is referred to herein as an IC50 value.

A therapeutically effective amount of an anti-uPA antibody or antigen-binding region thereof of this invention is typically an amount such that when administered in a physiologically tolerable composition is sufficient to achieve a plasma concentration (based on cmax data after a single dose of antibody) of, for example, from about 0.01 ug/ml to about 300 ug/ml. In another embodiment, the concentration may be from about 1 ug/ml to about 300 ug/ml. In yet another embodiment, the concentration may be from about 1 ug/ml to about 75 ug/ml. In yet another embodiment, the concentration may be from about 15 ug/ml to about 50 ug/ml. Dosages may, of course, vary according to frequency and duration of administration.

A therapeutically effective amount of an anti-uPA antibody or antigen-binding region thereof of this invention in the form of a polypeptide is typically an amount of polypeptide such that when administered in a physiologically tolerable composition is sufficient to achieve a plasma concentration of from about 0.001 ug/ml to about 10 ug/ml, or from about 0.05 ug/ml to about 1.0 ug/ml. Based on a polypeptide having a mass of about 15,000 grams per mole (i.e. 15,000 Da), the plasma concentration in molarity may be, for example, from about 0.0001 uM to about 1 mM. Stated differently, the dosage per body weight can vary from about 0.01 mg/kg to about 30 mg/kg, or from about 0.05 mg/kg to about 20 mg/kg, in one or more dose administrations daily, for one or several days. A typical dosage may range from about 0.1 mg/kg to up to about 100 mg/kg or more, depending on the factors mentioned above. In other embodiments, the dosage may range from 1 mg/kg up to about 100 mg/kg; or 5 mg/kg up to about 100 mg/kg.

For any compound, the therapeutically effective dose can be estimated initially either in cell culture assays or in animal models such as mice, rats, rabbits, dogs, pigs, or monkeys. An animal model may also be used to determine the appropriate concentration range and route of administration. Such information can then be used to determine useful doses and routes for administration in humans.

The exact dosage will be determined in light of factors related to the subject requiring treatment. Dosage and administration are adjusted to provide sufficient levels of the active compound or to maintain the desired effect. Factors that may be taken into account include the severity of the disease state, the general health of the subject, the age, weight, and gender of the subject, time and frequency of administration, drug combination(s), reaction sensitivities, and response to therapy. Long-acting pharmaceutical compositions may be administered every 3 to 4 days, every week, or biweekly depending on the half-life and clearance rate of the particular formulation.

The frequency of dosing will depend upon the pharmacokinetic parameters of the binding agent molecule in the formulation used. Typically, a composition is administered until a dosage is reached that achieves the desired effect. The composition may therefore be administered as a single dose, or as multiple doses (at the same or different concentrations/dosages) over time, or as a continuous infusion. Further refinement of the appropriate dosage is routinely made. Appropriate dosages may be ascertained through use of appropriate dose-response data.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved. In general, a suitable daily dose of a compositions of the invention will be that amount of the compound which is the lowest dose effective to produce a therapeutic effect. Such an effective dose will generally depend upon the factors described above. It is preferred that administration be intravenous, intramuscular, intraperitoneal, or subcutaneous, preferably administered proximal to the site of the target. If desired, the effective daily dose of a therapeutic compositions may be administered as two, three, four, five, six or more sub-doses administered separately at appropriate intervals throughout the day, optionally, in unit dosage forms. While it is possible for a compound of the present invention to be administered alone, it is preferable to administer the compound as a pharmaceutical formulation (composition).

The composition must be sterile and fluid to the extent that the composition is deliverable by syringe. In addition to water, the carrier can be an isotonic buffered saline solution, ethanol, polyol (for example, glycerol, propylene glycol, and liquid polyetheylene glycol, and the like), and suitable mixtures thereof. Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition. Long-term absorption of the injectable compositions can be brought about by including in the composition an agent which delays absorption, for example, aluminum monostearate or gelatin.

When the active compound is suitably protected, as described above, the compound may be orally administered, for example, with an inert diluent or an assimilable edible carrier.

Methods of administering the compositions (e.g., human antibodies, multispecific and bispecific molecules) of the invention are known in the art. Suitable dosages of the molecules used will depend on the age and weight of the subject and the particular drug used. The molecules can be coupled to radionuclides, such as 131I, 90Y, 105Rh, indium-111, etc., as described in Goldenberg, et al., *Cancer Res.* 41: 4354-4360 (1981), and in EP 0365 997. In another aspect the invention relates to an immunoconjugate comprising an antibody according to the invention linked to a radioisotope, cytotoxic agent (e.g., calicheamicin and duocarmycin), a cytostatic agent, or a chemotherapeutic drug. The compositions (e.g., human antibodies, multispecific and bispecific molecules) of the invention can also be coupled to anti-infectious agents.

Routes of Administration

The route of administration of the pharmaceutical composition is in accord with known methods, e.g. orally, through injection by intravenous, intraperitoneal, intracerebral (intraparenchymal), intracerebroventricular, intramuscular, intraocular, intraarterial, intraportal, intralesional routes, intramedullary, intrathecal, intraventricular, transdermal, subcutaneous, intraperitoneal, intranasal, enteral, topical, sublingual, urethral, vaginal, or rectal means, by sustained release systems or by implantation devices. Where desired, the compositions may be administered by bolus injection or continuously by infusion, or by implantation device.

Alternatively or additionally, the composition may be administered locally via implantation of a membrane, sponge, or another appropriate material on to which the desired molecule has been absorbed or encapsulated. Where an implantation device is used, the device may be implanted into any suitable tissue or organ, and delivery of the desired molecule may be via diffusion, timed-release bolus, or continuous administration.

In some cases, it may be desirable to use pharmaceutical compositions in an ex vivo manner. In such instances, cells, tissues, or organs that have been removed from the patient are exposed to the pharmaceutical compositions after which the cells, tissues and/or organs are subsequently implanted back into the patient.

In other cases, a binding agent of the present invention such as an antibody or antigen-binding region thereof can be delivered by implanting certain cells that have been genetically engineered, using methods such as those described herein, to express and secrete the polypeptide. Such cells may be animal or human cells, and may be autologous, heterologous, or xenogeneic. Optionally, the cells may be immortalized. In order to decrease the chance of an immunological response, the cells may be encapsulated to avoid infiltration of surrounding tissues. The encapsulation materials are typically biocompatible, semi-permeable polymeric enclosures or membranes that allow the release of the protein product(s) but prevent the destruction of the cells by the patient's immune system or by other detrimental factors from the surrounding tissues.

Therapeutic compositions can be administered with medical devices known in the art. For example, in a preferred embodiment, a therapeutic composition of the invention can be administered with a needleless hypodermic injection device, such as the devices disclosed in U.S. Pat. Nos. 5,399, 163; 5,383,851; 5,312,335; 5,064,413; 4,941,880; 4,790,824; or 4,596,556. Examples of well-known implants and modules useful in the present invention include: U.S. Pat. No. 4,487, 603, which discloses an implantable micro-infusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

When parenteral administration is contemplated, the therapeutic compositions for use in this invention may be in the form of a pyrogen-free, parenterally acceptable aqueous solution comprising the desired specific binding agent in a pharmaceutically acceptable vehicle. A particularly suitable vehicle for parenteral injection is sterile distilled water in which a binding agent is formulated as a sterile, isotonic solution, properly preserved. Yet another preparation can involve the formulation of the desired molecule with an agent, such as injectable microspheres, bio-erodible particles, polymeric compounds (polylactic acid, polyglycolic acid), beads, or liposomes, that provides for the controlled or sustained release of the product which may then be delivered via a depot injection. Hyaluronic acid may also be used, and this may have the effect of promoting sustained duration in the circulation. Other suitable means for the introduction of the desired molecule include implantable drug delivery devices.

In another aspect, pharmaceutical formulations suitable for parenteral administration may be formulated in aqueous solutions, preferably in physiologically compatible buffers such as Hanks' solution, ringer's solution, or physiologically buffered saline. Aqueous injection suspensions may contain substances that increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also contain suitable stabilizers or agents to increase the solubility of the compounds and allow for the preparation of highly concentrated solutions.

In another embodiment, a pharmaceutical composition may be formulated for inhalation. For example, a binding agent may be formulated as a dry powder for inhalation. Polypeptide or nucleic acid molecule inhalation solutions may also be formulated with a propellant for aerosol delivery. In yet another embodiment, solutions may be nebulized. Pulmonary administration is further described in PCT Application No. PCT/US94/001875, which describes pulmonary delivery of chemically modified proteins.

Pharmaceutical compositions for oral administration can also be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient. In one embodiment of the present invention, binding agent molecules that are administered in this fashion can be formulated with or without those carriers customarily used in the compounding of solid dosage forms such as tablets and capsules. For example, a capsule may be designed to release the active portion of the formulation at the point in the gastrointestinal tract when bioavailability is maximized and pre-systemic degradation is minimized. Additional agents can be included to facilitate absorption of the binding agent molecule. Diluents, flavorings, low melting point waxes, vegetable oils, lubricants, suspending agents, tablet disintegrating agents, and binders may also be employed.

Pharmaceutical preparations for oral use can be obtained through combining active compounds with solid excipient and processing the resultant mixture of granules (optionally, after grinding) to obtain tablets or dragee cores. Suitable auxiliaries can be added, if desired. Suitable excipients include carbohydrate or protein fillers, such as sugars, including lactose, sucrose, mannitol, and sorbitol; starch from corn, wheat, rice, potato, or other plants; cellulose, such as methyl cellulose, hydroxypropylmethyl-cellulose, or sodium carboxymethylcellulose; gums, including arabic and tragacanth; and proteins, such as gelatin and collagen. If desired, disintegrating or solubilizing agents may be added, such as the cross-linked polyvinyl pyrrolidone, agar, and alginic acid or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations that can be used orally also include push-fit capsules made of gelatin, as well as soft, sealed capsules made of gelatin and a coating, such as glycerol or sorbitol. Push-fit capsules can contain active ingredients mixed with fillers or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Another pharmaceutical composition may involve an effective quantity of binding agent in a mixture with non-toxic excipients that are suitable for the manufacture of tablets. By dissolving the tablets in sterile water, or other appropriate vehicle, solutions can be prepared in unit dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions will be evident to those skilled in the art, including formulations involving binding agent molecules in sustained- or controlled-delivery formulations. Techniques for formulating a variety of other sustained- or controlled-delivery means, such as liposome carriers, bio-erodible microparticles or porous beads and depot injections, are also known to those skilled in the art. See for example, PCT/US93/00829 that describes controlled release of porous polymeric microparticles for the delivery of pharmaceutical compositions. Additional examples of sustained-release preparations include semipermeable polymer matrices in the form of shaped articles, e.g. films, or microcapsules. Sustained release matrices may include polyesters, hydrogels, polylactides (U.S. Pat. No. 3,773,919, EP 58,481), copolymers of L-glutamic acid and gamma ethyl-L-glutamate [Sidman et al., *Biopolymers* 22:547-556 (1983)], poly(2-hydroxyethyl-methacrylate) [Langer et al., *J. Biomed. Mater. Res.* 15:167-277, (1981)] and [Langer et al., *Chem. Tech.* 12:98-105 (1982)], ethylene vinyl acetate (Langer et al., supra) or poly-D(−)-3-hydroxybutyric acid (EP 133,988). Sustained-release compositions also include liposomes, which can be prepared by any of several methods known in the art. See e.g., Eppstein et al., *Proc. Natl. Acad. Sci. (USA)* 82:3688-3692 (1985); EP 36,676; EP 88,046; EP 143,949.

The pharmaceutical composition to be used for in vivo administration typically must be sterile. This may be accomplished by filtration through sterile filtration membranes. Where the composition is lyophilized, sterilization using this method may be conducted either prior to or following lyophilization and reconstitution. The composition for parenteral administration may be stored in lyophilized form or in solution. In addition, parenteral compositions generally are placed into a container having a sterile access port, for example, an intravenous solution bag or vial having a stopper pierceable by a hypodermic injection needle.

Once the pharmaceutical composition has been formulated, it may be stored in sterile vials as a solution, suspension, gel, emulsion, solid, or a dehydrated or lyophilized powder. Such formulations may be stored either in a ready-to-use form or in a form (e.g., lyophilized) requiring reconstitution prior to administration.

In a specific embodiment, the present invention is directed to kits for producing a single-dose administration unit. The kits may each contain both a first container having a dried protein and a second container having an aqueous formulation. Also included within the scope of this invention are kits containing single and multi-chambered pre-filled syringes (e.g., liquid syringes and lyosyringes).

Combination Therapies

In another aspect, the present invention provides a composition, e.g., a pharmaceutical composition, containing one or a combination of human antibodies, or antigen-binding region(s) thereof, of the present invention, formulated together with a pharmaceutically acceptable carrier. In another embodiment, the compositions include a combination of multiple (e.g., two or more) isolated human antibodies or antigen-binding regions thereof of the invention. In a more particular embodiment, each of the antibodies or antigen-binding regions thereof of the composition binds to a distinct, pre-selected epitope of uPA.

In one embodiment, human anti-uPA monoclonal antibodies having complementary activities are used in combination, e.g., as a pharmaceutical composition, comprising two or more human anti-uPA monoclonal antibodies. For example, a human monoclonal antibody that inhibits inflammation or the growth of cells expressing uPA, may also be combined with another human antibody that mediates highly effective killing of target cells in the presence of effector cells.

In another embodiment, the composition comprises one or a combination of bispecific or multispecific molecules of the invention (e.g., which contains at least one binding specificity for an Fc receptor and at least one binding specificity for uPA).

The invention thus includes administration of the antibodies or antigen-binding regions thereof of the present invention administered to the same patient in combination with one or more additionally suitable agent(s), each being administered according to a regimen suitable for that medicament. This includes concurrent administration of a specific binding agent of the invention and one or more suitable agents. As used herein, the terms "concurrently administered" and "concurrent administration" encompass substantially simultaneous administration of one or more antibody according to the invention and one or more additionally suitable agents(s).

As used herein, the term, "non-concurrent" administration encompasses administering one or more antibodies or antigen-binding regions thereof according to the invention and one or more additionally suitable agent(s), at different times, in any order, whether overlapping or not. This includes, but is not limited to, sequential treatment (such as pretreatment, post-treatment, or overlapping treatment) with the components of the combination, as well as regimens in which the drugs are alternated, or wherein one component is administered long-term and the other(s) are administered intermittently. Components may be administered in the same or in separate compositions, and by the same or different routes of administration.

Chemotherapy treatment can employ anti-neoplastic agents including, for example, alkylating agents including: nitrogen mustards, such as mechlorethamine, cyclophosphamide, ifosfamide, melphalan and chlorambucil; nitrosoureas, such as carmustine (BCNU), lomustine (CCNU), and semustine (methyl-CCNU); ethylenimines/methylmelamine such as thriethylenemelamine (TEM), triethylene, thiophosphoramide (thiotepa), hexamethylmelamine (HMM, altretamine); alkyl sulfonates such as busulfan; triazines such as dacarbazine (DTIC); antimetabolites including folic acid analogs such as methotrexate and trimetrexate, pyrimidine analogs such as 5-fluorouracil, fluorodeoxyuridine, gemcitabine, cytosine arabinoside (AraC, cytarabine), 5-azacytidine, 2,2'-difluorodeoxycytidine-, purine analogs such as 6-mercaptopurine, 6-thioguanine, azathioprine, 2'-deoxycoformycin (pentostatin), erythrohydroxynonyladenine (EHNA), fludarabine phosphate, and 2-chlorodeoxyadenosine (cladribine, 2-CdA); natural products including antimitotic drugs such as paclitaxel, vinca alkaloids including vinblastine (VLB), vincristine, and vinorelbine, taxotere, estramustine, and estramustine phosphate; ppipodophylotoxins such as etoposide and teniposide; antibiotics such as actimomycin D, daunomycin (rubidomycin), doxorubicin, mitoxantrone, idarubicin, bleomycins, plicamycin (mithramycin), mitomycinC, and actinomycin; enzymes such as L-asparaginase; biological response modifiers such as interferon-alpha, IL-2, G-CSF and GM-CSF; miscellaneous agents including platinium coordination complexes such as cisplatin and carboplatin, anthracenediones such as mitoxantrone, substituted urea such as hydroxyurea, methylhydrazine derivatives including N-methylhydrazine (M1H) and procarbazine, adrenocortical suppressants such as mitotane (o,p'-DDD) and aminoglutethimide; hormones and antagonists including adrenocorticosteroid antagonists such as prednisone and equivalents, dexamethasone and aminoglutethimide; progestin such as hydroxyprogesterone caproate, medroxyprogesterone acetate and megestrol acetate; estrogen such as diethylstilbestrol and ethinyl estradiol equivalents; antiestrogen such as tamoxifen; androgens including testosterone propionate and fluoxymesterone/equivalents; antiandrogens such as flutamide, gonadotropin-releasing hormone analogs and leuprolide; and non-steroidal antiandrogens such as flutamide.

Combination therapy with growth factors can include cytokines, lymphokines, growth factors, or other hematopoietic factors such as M-CSF, GM-CSF, TNF, IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IFN, TNF0, TNF1, TNF2, G-CSF, Meg-CSF, GM-CSF, thrombopoietin, stem cell factor, and erythropoietin. Other are compositions can include known angiopoietins, for example Ang-1, -2, -4, -Y, and/or the human Ang-like polypeptide, and/or vascular endothelial growth factor (VEGF). Growth factors include angiogenin, bone morphogenic protein-1, bone morphogenic protein-2, bone morphogenic protein-3, bone morphogenic protein-4, bone morphogenic protein-5, bone morphogenic protein-6, bone morphogenic protein-7, bone morphogenic protein-8, bone morphogenic protein-9, bone morphogenic protein-10, bone morphogenic protein-11, bone morphogenic protein-12, bone morphogenic protein-13, bone morphogenic protein-14, bone morphogenic protein-15, bone morphogenic protein receptor IA, bone morphogenic protein receptor IB, brain derived neurotrophic factor, ciliary neutrophic factor, ciliary neutrophic factor receptor, cytokine-induced neutrophil chemotactic factor 1, cytokine-induced neutrophil, chemotactic factor 2, cytokine-induced neutrophil chemotactic factor 2, endothelial cell growth factor, endothelin 1, epidermal growth factor, epithelial-derived neutrophil attractant, fibroblast growth factor 4, fibroblast growth factor 5, fibroblast growth factor 6, fibroblast growth factor 7, fibroblast growth factor 8, fibroblast growth factor 8b, fibroblast growth factor 8c, fibroblast growth factor 9, fibroblast growth factor 10, fibroblast growth factor acidic, fibroblast growth factor basic, glial cell line-derived neutrophic factor receptor-1, glial cell line-derived neutrophic factor receptor-2, growth related protein, growth related protein-1, growth related protein-2, growth related protein-3, heparin binding epidermal growth factor, hepatocyte growth factor, hepatocyte growth factor receptor, insulin-like growth factor I, insulin-like growth factor receptor, insulin-like growth factor II, insulin-like growth factor binding protein, keratinocyte growth factor, leukemia inhibitory factor, leukemia inhibitory factor receptor-1, nerve growth factor nerve growth factor receptor, neurotrophin-3, neurotrophin-4, placenta growth factor, placenta growth factor 2, platelet-derived endothelial cell growth factor, platelet derived growth factor, platelet derived growth factor A chain, platelet derived growth factor AA, platelet derived growth factor AB, platelet derived growth factor B chain, platelet derived growth factor BB, platelet derived growth factor receptor-1, platelet derived growth factor receptor-2, pre-B cell growth stimulating factor, stem cell factor, stem cell factor receptor, transforming growth factor-1, transforming growth factor-2, transforming growth factor-1, transforming growth factor-1.2, transforming growth factor-2, transforming growth factor-3, transforming growth factor-5, latent transforming growth factor-1, transforming growth factor-1 binding protein I, transforming growth factor-I binding protein II, transforming growth factor-I binding protein III, tumor necrosis factor receptor type I (TNF-R1), tumor necrosis factor receptor type II (TNF-R2), urokinase-type plasminogen activator receptor, vascular endothelial growth factor, and chimeric proteins and biologically or immunologically active fragments thereof.

It will be appreciated that the antibodies or antigen-binding regions thereof of the invention may be administered with one or more anti-inflammatory agents. As used herein, the term "anti-inflammatory agent" refers generally to any agent that reduces inflammation or swelling in a patient. A number of exemplary anti-inflammatory agents are recited herein, but it will be appreciated that there may be additional suitable anti-inflammatory agents not specifically recited herein, but which are encompassed by the present invention.

The anti-inflammatory agent can be, for example, a compound that inhibits the interaction of inflammatory cytokines with their receptors. Examples of cytokine inhibitors useful in combination with the specific binding agents of the invention include, for example, antagonists (such as antibodies) of TGF-beta, as well as antagonists (such as antibodies) directed against interleukins involved in inflammation. Such interleukins are described herein and preferably include, but are not limited to, IL-1, IL-2, IL-3, IL-4, IL-5, IL-6, IL-8, IL-9, IL-11, IL-12, IL-13, IL-17, and IL-18. See Feghali, et al., Frontiers in Biosci., 2:12-26 (1997). Exemplary antibody antagonists also include antibodies directed against the 21-28 kD cell surface glycoprotein CD52 (such as CamPath®, Berlex Laboratories), IL-8 (and anti-IL8-RB antibodies), B-FGF (and anti-B-FGF receptor antibodies), anti-TWEAK antibodies (and anti-TWEAK receptor (i.e., TWEAKR) antibodies), anti-Adam/Disintegrin antibodies, anti-eph receptor, anti-ephrin antibodies, and anti-PDGF-BB antibodies.

Specific antibodies or antigen-binding regions thereof of the invention also may be administered in combination with inhibitors of Protein Kinase A Type 1 to enhance T cell proliferation in HIV-infected patients who are receiving anti-retroviral therapy.

Nerve growth factors (NGFs) also can be combined with the antibodies or antigen-binding regions thereof of the invention to treat certain conditions. Such conditions include neurodegenerative diseases, spinal cord injury and multiple sclerosis. Other conditions treatable with this combination are glaucoma and diabetes.

A preferred combination therapy relates to antibodies or antigen-binding regions thereof of the invention administered to a patient in combination with one or more suitable 1L-1 inhibitor. Inhibitors of IL-1 include, but are not limited to, receptor-binding peptide fragments of IL-1, antibodies directed against IL-1 or IL-1 beta or IL-1 receptor type I, and recombinant proteins comprising all or portions of receptors for IL-1 or modified variants thereof, including genetically-modified muteins, multimeric forms and sustained-release formulations. Specific antagonists include IL-Ira polypeptides, IL-1 beta converting enzyme (ICE) inhibitors, antagonistic type I IL-1 receptor antibodies, IL-1 binding forms of type I IL-1 receptor and type II IL-1 receptor, antibodies to IL-1, including IL-1 alpha and IL-1 beta and other IL-1 family members, and a therapeutic known as IL-1 Trap (Regeneron). IL-Ira polypeptides include the forms of IL-Ira described in U.S. Pat. No. 5,075,222 and modified forms and variants including those described in U.S. Pat. No. 5,922,573, WO 91/17184, WO 92 16221, and WO 96 09323. IL-1 beta converting enzyme (ICE) inhibitors include peptidyl and small molecule ICE inhibitors including those described in PCT patent applications WO 91/15577; WO 93/05071; WO 93/09135; WO 93/14777 and WO 93/16710; and European patent application 0 547 699. Non-peptidyl compounds include those described in PCT patent application WO 95/26958, U.S. Pat. Nos. 5,552,400, 6,121,266, and Dolle et al., J. Med. Chem., 39, pp. 2438-2440 (1996). Additional ICE inhibitors are described in U.S. Pat. Nos. 6,162,790, 6,204,261, 6,136,787, 6,103,711, 6,025,147, 6,008,217, 5,973,111, 5,874,424, 5,847,135, 5,843,904, 5,756,466, 5,656,627, 5,716,929. IL-1 binding forms of Type I IL-1 receptor and type II IL-1 receptor are described in U.S. Pat. Nos. 4,968,607, 4,968,607, 5,081,228, Re Pat. No. 35,450, U.S. Pat. Nos. 5,319,071, and 5,350,683. Other suitable IL-1 antagonists include, but are not limited to, peptides derived from IL-1 that are capable of binding competitively to the IL-1 signaling receptor, IL-1 R type I. Additional guidance regarding certain IL-1 (and other cytokine) antagonists can be found in U.S. Pat. No. 6,472,179.

Additionally, TNF inhibitors are suitable, and include, but are not limited to, receptor-binding peptide fragments of TNF-alpha, antisense oligonucleotides or ribozymes that inhibit TNF.alpha. production, antibodies directed against TNF-alpha, and recombinant proteins comprising all or portions of receptors for TNF-alpha or modified variants thereof, including genetically-modified muteins, multimeric forms and sustained-release formulations. Also suitable are TACE (Tumor Necrosis Factor-alpha Converting Enzyme) inhibitors, such as TAPI (Immunex Corp.) and GW-3333X (Glaxo Wellcome Inc.). Also suitable are molecules that inhibit the formation of the IgA-alpha-1AT complex, such as the peptides disclosed in EP 0 614 464 B, or antibodies against this complex. Additionally suitable molecules include, but are not limited to, TNF-alpha-inhibiting disaccharides, sulfated derivatives of glucosamine, or other similar carbohydrates described in U.S. Pat. No. 6,020,323. Further suitable molecules include peptide TNF-alpha inhibitors disclosed in U.S. Pat. Nos. 5,641,751 and 5,519,000, and the D-amino acid-containing peptides described in U.S. Pat. No. 5,753,628. In addition, inhibitors of TNF-alpha converting enzyme are also suitable. WO 01/03719 describes further additional agents which can be used in combination in accordance with the invention.

Still Further suitable compounds include, but are not limited to, small molecules such as thalidomide or thalidomide analogs, pentoxifylline, or matrix metalloproteinase (MMP) inhibitors or other small molecules. Suitable MMP inhibitors for this purpose include, for example, those described in U.S. Pat. Nos. 5,883,131, 5,863,949 and 5,861,510 as well as mercapto alkyl peptidyl compounds as described in U.S. Pat. No. 5,872,146. Other small molecules capable of reducing TNF-alpha production, include, for example, the molecules described in U.S. Pat. Nos. 5,508,300, 5,596,013, and 5,563,143. Additional suitable small molecules include, but are not limited to, MMP inhibitors as described in U.S. Pat. Nos. 5,747,514, and 5,691,382, as well as hydroxamic acid derivatives such as those described in U.S. Pat. No. 5,821,262. Further suitable molecules include, for example, small molecules that inhibit phosphodiesterase IV and TNF-alpha production, such as substituted oxime derivatives (WO 96/00215), quinoline sulfonamides (U.S. Pat. No. 5,834,485), aryl furan derivatives (WO 99/18095) and heterobicyclic derivatives (WO 96/01825; GB 2 291 422 A). Also useful are thiazole derivatives that suppress TNF-alpha and IFN-gamma (WO 99/15524), as well as xanthine derivatives that suppress TNF-alpha and other proinflammatory cytokines (see, for example, U.S. Pat. Nos. 5,118,500, 5,096,906 and 5,196,430). Additional small molecules useful for treating the hereindescribed conditions include those disclosed in U.S. Pat. No. 5,547,979.

Further examples of drugs and drug types which can be administered by combination therapy include, but are not limited to, antivirals, antibiotics, analgesics (e.g., acetaminophen, codeine, propoxyphene napsylate, oxycodone hydrochloride, hydrocodone bitartrate, tramadol), corticosteroids, antagonists of inflammatory cytokines, Disease-Modifying Anti-Rheumatic Drugs (DMARDs), Non-Steroidal Anti-Inflammatory drugs (NSAIDs), and Slow-Acting Anti-Rheumatic Drugs (SAARDs).

Exemplary Disease-Modifying Anti-Rheumatic Drugs (DMARDs) include, but are not limited to: Rheumatrex™ (methotrexate); Enbrel® (etanercept); Remicade® (infliximab); Humira™ (adalimumab); Segard® (afelimomab); Arava™ (leflunomide); Kineret™ (anakinra); Arava™ (leflunomide); D-penicillamine; Myochrysine; Plaquenil; Ridaura™ (auranofin); Solganal; lenercept (Hoffman-La Roche); CDP870 (Celltech); CDP571 (Celltech), as well as the antibodies described in EP 0 516 785 B1, U.S. Pat. No. 5,656,272, EP 0 492 448 A1; onercept (Serono; CAS reg. no. 199685-57-9); MRA (Chugai); Imuran™ (azathioprine); NFKB inhibitors; Cytoxan™ (cyclophosphamide); cyclosporine; hydroxychloroquine sulfate; minocycline; sulfasalazine; and gold compounds such as oral gold, gold sodium thiomalate and aurothioglucose.

Further suitable molecules include, for example, soluble TNFRs derived from the extracellular regions of TNF-alpha receptor molecules other than the p55 and p75 TNFRs, such as for example the TNFR described in WO 99/04001, including TNFR-Ig's derived from this TNFR. Additional suitable TNF-alpha inhibitors are suitable for use as described herein. These include the use not only of an antibody against TNF-alpha or TNFR as described herein, but also a TNF-alpha derived peptide that can act as a competitive inhibitor of TNF-alpha (such as those described in U.S. Pat. No. 5,795, 859 or 6,107,273), TNFR-IgG fusion proteins, such as one containing the extracellular portion of the p55 TNF-alpha receptor, a soluble TNFR other than an IgG fusion protein, or other molecules that reduce endogenous TNF-alpha levels, such as inhibitors of the TNF-alpha converting enzyme (see e.g., U.S. Pat. No. 5,594,106), or small molecules or TNF-alpha inhibitors, a number of which are described herein.

With respect to antibodies to TNF, although dose will optimally be determined by an experienced healthcare provider in accordance with the specific needs of the patient in mind, one exemplary preferred dose range for an antibody against TNF-alpha is 0.1 to 20 mg/kg, and more preferably is 1-10 mg/kg. Another preferred dose range for anti-TNF-alpha antibody is 0.75 to 7.5 mg/kg of body weight.

The present invention can also utilize a specific binding agent and any of one or more Non-Steroidal Anti-Inflammatory Drugs (NSAIDs). NSAIDs owe their anti-inflammatory action, at least in part, to the inhibition of prostaglandin synthesis. Goodman and Gilman, The Pharmacological Basis of Therapeutics, MacMillan 7th Edition (1985). NSAIDs can be characterized into nine groups: (1) salicylic acid derivatives; (2) propionic acid derivatives; (3) acetic acid derivatives; (4) fenamic acid derivatives; (5) carboxylic acid derivatives; (6) butyric acid derivatives; (7) oxicams; (8) pyrazoles and (9) pyrazolones. Examples of NSAIDs include, but are not limited to: Anaprox™, Anaprox DS™ (naproxen sodium); Ansaid™ (flurbiprofen); Arthrotec™ (diclofenac sodium+misoprostil); Cataflam™/Voltaren™ (diclofenac potassium); Clinoril™ (sulindac); Daypro™ (oxaprozin); Disalcid™ (salsalate); Dolobid™ (diflunisal); EC Naprosyn™ (naproxen sodium); Feldene™ (piroxicam); Indocin™, Indocin SR™ (indomethacin); Lodine™, Lodine XL™ (etodolac); Motrin™ (ibuprofen); Naprelan™ (naproxen); Naprosyn™ (naproxen); Orudis™, (ketoprofen); Oruvail™ (ketoprofen); Relafen™ (nabumetone); Tolectin™, (tolmetin sodium); Trilisate™ (choline magnesium trisalicylate); Cox-1 inhibitors; Cox-2 Inhibitors such as Vioxx™ (rofecoxib); Arcoxia™ (etoricoxib), Celebrex™ (celecoxib); Mobic™ (meloxicam); Bextra™ (valdecoxib), Dynastat™ paracoxib sodium; Prexige™ (lumiracoxib), and nambumetone. Additional suitable NSAIDs, include, but are not limited to, the following: .epsilon.-acetamidocaproic acid, S-adenosylmethionine, 3-amino-4-hydroxybutyric acid, amixetrine, anitrazafen, antrafenine, bendazac, bendazac lysinate, benzydamine, beprozin, broperamole, bucolome, bufezolac, ciproquazone, cloximate, dazidamine, deboxamet, detomidine, difenpiramide, difenpyramide, difisalamine, ditazol, emorfazone, fanetizole mesylate, fenflumizole, floctafenine, flumizole, flunixin, fluproquazone, fopirtoline, fosfosal, guaimesal, guaiazolene, isonixirn, lefetamine HCl, leflunomide, lofemizole, lotifazole, lysin clonixinate, meseclazone, nabumetone, nictindole, nimesulide, orgotein, orpanoxin, oxaceprolm, oxapadol, paranyline, perisoxal, perisoxal citrate, pifoxime, piproxen, pirazolac, pirfenidone, proquazone, proxazole, thielavin B, tiflamizole, timegadine, tolectin, tolpadol, tryptamid and those designated by company code number such as 480156S, AA861, AD1590, AFP802, AFP860, A177B, AP504, AU8001, BPPC, BW540C, CHINOIN 127, CN100, EB382, EL508, F1044, FK-506, GV3658, ITF182, KCNTEI6090, KME4, LA2851, MR714, MR897, MY309, ONO.sub.3144, PR823, PV102, PV108, R830, RS2131, SCR152, SH440, SIR133, SPAS510, SQ27239, ST281, SY6001, TA60, TAI-901 (4-benzoyl-1-indancarboxylic acid), TVX2706, U60257, UR2301 and WY41770. Structurally related NSAIDs having similar analgesic and anti-inflammatory properties to the NSAIDs are also encompassed by this group.

Suitable SAARDs or DMARDS include, but are not limited to: allocupreide sodium, auranofin, aurothioglucose, aurothioglycamide, azathioprine, brequinar sodium, bucillamine, calcium 3-aurothio-2-propanol-1-sulfonate, chlorambucil, chloroquine, clobuzarit, cuproxoline, cyclophosphamide, cyclosporin, dapsone, 15-deoxyspergualin, diacerein, glucosamine, gold salts (e.g., cycloquine gold salt, gold sodium thiomalate, gold sodium thiosulfate), hydroxychloroquine, hydroxyurea, kebuzone, levamisole, lobenzarit, melittin, 6-mercaptopurine, methotrexate, mizoribine, mycophenolate mofetil, myoral, nitrogen mustard, D-penicillamine, pyridinol imidazoles such as SKNF86002 and SB203580, rapamycin, thiols, thymopoietin and vincristine. Structurally related SAARDs or DMARDs having similar analgesic and anti-inflammatory properties are also intended to be encompassed by this group.

Inhibitors of kinases in signaling cascades are also suitable agents for combination with the specific binding agents of the invention. These include, but are not limited to, agents which are capable of inhibiting P-38 (a.k.a., "RK" or "SAPK-2", Lee et al., Nature, 372:739 (1994). P-38 is described as a serine/threonine kinase (see Han et al., Biochimica Biophysica Acta, 1265:224-227 (1995). Inhibitors of P-38 have been shown to intervene between the extracellular stimulus and the secretion of IL-1 and TNF-alpha from the cell involves blocking signal transduction through inhibition of a kinase which lies on the signal pathway.

Additionally suitable are MK2 inhibitors, and tpl-2 inhibitors. Additionally, T-cell inhibitors are also suitable, including, for example, ctla-4, CsA, Fk-506, OX40, OX40R-Fc, OX40 antibody, OX40 ligand, OX40 ligand antibody, lck, and ZAP70. Also suitable are retinoids, including oral retinoids, as well as antagonists of TGF-beta.

Further suitable agents for combination with the specific binding agents of the invention include, for example, any of one or more salicylic acid derivatives, prodrug esters or pharmaceutically acceptable salts thereof. Such salicylic acid derivatives, prodrug esters and pharmaceutically acceptable salts thereof comprise: acetaminosalol, aloxiprin, aspirin, benorylate, bromosaligenin, calcium acetylsalicylate, choline magnesium trisalicylate diflusinal, etersalate, fendosal, gentisic acid, glycol salicylate, imidazole salicylate, lysine acetylsalicylate, mesalamine, morpholine salicylate, 1-naphthyl salicylate, olsalazine, parsalmide, phenyl acetylsalicylate, phenyl salicylate, salacetamide, salicylamide O-acetic acid, salsalate and sulfasalazine. Structurally related salicylic acid derivatives having similar analgesic and anti-inflammatory properties are also intended to be encompassed by this group. Additionally suitable agents include, for example propionic acid derivatives, prodrug esters or pharmaceutically acceptable salts thereof. The propionic acid derivatives, prodrug esters and pharmaceutically acceptable salts thereof comprise: alminoprofen, benoxaprofen, bucloxic acid, carprofen, dexindoprofen, fenoprofen, flunoxaprofen, fluprofen, flurbiprofen, furcloprofen, ibuprofen, ibuprofen aluminum, ibuproxam, indoprofen, isoprofen, ketoprofen, loxoprofen, miroprofen, naproxen, oxaprozin, piketoprofen, pimeprofen, pirprofen, pranoprofen, protizinic acid, pyridoxiprofen, suprofen, tiaprofenic acid and tioxaprofen. Structurally related propionic acid derivatives having similar analgesic and anti-inflammatory properties are also intended to be encompassed by this group. Also suitable for use are acetic acid derivatives, prodrug esters or pharmaceutically acceptable salts thereof. The acetic acid derivatives, prodrug esters and pharmaceutically acceptable salts thereof comprise: acemetacin, alclofenac, amfenac, bufexamac, cinmetacin, clopirac, delmetacin, diclofenac sodium, etodolac, felbinac, fenclofenac, fenclorac, fenclozic acid, fentiazac, furofenac, glucametacin, ibufenac, indomethacin, isofezolac, isoxepac, lonazolac, metiazinic acid, oxametacin, oxpinac, pimetacin, proglumetacin, sulindac, talmetacin, tiaramide, tiopinac, tolmetin, zidometacin and zomepirac. Structurally related acetic acid derivatives having similar analgesic and anti-inflammatory properties are also intended to be encompassed by this group. Further suitable for use as described herein are fenamic acid derivatives, prodrug esters or pharmaceutically acceptable salts thereof. The fenamic acid derivatives, prodrug esters and pharmaceutically acceptable salts thereof comprise: enfenamic acid, etofenamate, flufenamic acid, isonixin, meclofenamic acid, meclofenarnate sodium, medofenamic acid, mefanamic acid, niflumic acid, talniflumate, terofenamate, tolfenamic acid and ufenamate. Structurally related fenamic acid derivatives having similar analgesic and anti-inflammatory properties are also intended to be encompassed by this group.

Also suitable are carboxylic acid derivatives, prodrug esters and pharmaceutically acceptable salts thereof which can be used comprise: clidanac, diflunisal, flufenisal, inoridine, ketorolac and tinoridine. Structurally related carboxylic acid derivatives having similar analgesic and anti-inflammatory properties are also intended to be encompassed by this group. Additionally suitable are butyric acid derivatives, prodrug esters or pharmaceutically acceptable salts thereof. The butyric acid derivatives, prodrug esters and pharmaceutically acceptable salts thereof comprise: bumadizon, butibufen, fenbufen and xenbucin. Structurally related butyric acid derivatives having similar analgesic and anti-inflammatory properties are also intended to be encompassed by this group. Oxicams, prodrug esters or pharmaceutically acceptable salts thereof are also suitable. Oxicams, prodrug esters and pharmaceutically acceptable salts thereof comprise: droxicam, enolicam, isoxicam, piroxicam, sudoxicam, tenoxicam and 4-hydroxyl-1,2-benzothiazine 1,1-dioxide 4-(N-phenyl)-carboxamide. Structurally related oxicams having similar analgesic and anti-inflammatory properties are also intended to be encompassed by this group. Pyrazoles, prodrug esters or pharmaceutically acceptable salts thereof are also suitable. The pyrazoles, prodrug esters and pharmaceutically acceptable salts thereof which may be used comprise: difenamizole and epirizole. Structurally related pyrazoles having similar analgesic and anti-inflammatory properties are also intended to be encompassed by this group. Furthermore, pyrazolones, prodrug esters or pharmaceutically acceptable salts thereof are suitable. The pyrazolones, prodrug esters and pharmaceutically acceptable salts thereof which may be used comprise: apazone, azapropazone, benzpiperylon, feprazone, mofebutazone, morazone, oxyphenbutazone, phenylbutazone, pipebuzone, propylphenazone, ramifenazone, suxibuzone and thiazolinobutazone. Structurally related pyrazalones having similar analgesic and anti-inflammatory properties are also intended to be encompassed by this group.

Also suitable are prodrug esters or pharmaceutically acceptable salts thereof for the treatment of TNF-mediated diseases. Corticosteroids, prodrug esters and pharmaceutically acceptable salts thereof include hydrocortisone and compounds which are derived from hydrocortisone, such as 21-acetoxy-pregnenolone, alclomerasone, algestone, amcinonide, beclomethasone, beta-methasone, betamethasone valerate, budesonide, chloroprednisone, clobetasol, clobetasol propionate, clobetasone, clobetasone butyrate, clocortolone, cloprednol, corticosterone, cortisone, cortivazol, deflazacon, desonide, desoximerasone, dexamethasone, diflorasone, diflucortolone, difluprednate, enoxolone, fluazacort, flucloronide, flumethasone, flumethasone pivalate, flunisolide, flucinolone acetonide, fluocinonide, fluorocinolone acetonide, fluocortin butyl, fluocortolone, fluorocortolone hexanoate, diflucortolone valerate, fluorometholone, fluperolone acetate, fluprednidene acetate, fluprednisolone, flurandenolide, formocortal, halcinonide, halometasone, halopredone acetate, hydrocortamate, hydrocortisone, hydrocortisone acetate, hydro-cortisone butyrate, hydrocortisone phosphate, hydrocortisone 21-sodium succinate, hydrocortisone tebutate, mazipredone, medrysone, meprednisone, methylprednicolone, mometasone furoate, paramethasone, prednicarbate, prednisolone, prednisolone 21-diedryaminoacetate, prednisolone sodium phosphate, prednisolone sodium succinate, prednisolone sodium 21-m-sulfobenzoate, prednisolone sodium 21-stearoglycolate, prednisolone tebutate, prednisolone 21-trimethylacetate, prednisone, prednival, prednylidene, prednylidene 21-diethylaminoacetate, tixocortol, triamcinolone, triamcinolone acetonide, triamcinolone benetonide and triamcinolone hexacetonide. Structurally related corticosteroids having similar analgesic and anti-inflammatory properties are also intended to be encompassed by this group.

Antimicrobials (and prodrug esters or pharmaceutically acceptable salts thereof) are also suitable for combination use as described herein. Suitable antimicrobials include, for example, ampicillin, amoxycillin, aureomicin, bacitracin, ceftazidime, ceftriaxone, cefotaxime, cephachlor, cephalexin, cephradine, ciprofloxacin, clavulanic acid, cloxacillin, dicloxacillan, erythromycin, flucloxacillan, gentamicin, gramicidin, methicillin, neomycin, oxacillan, penicillin and vancomycin. Structurally related antimicrobials having similar analgesic and anti-inflammatory properties are also intended to be encompassed by this group.

Additional suitable compounds include, but are not limited to: BN 50730; tenidap; E 5531; tiapafant PCA 4248; nimesulide; panavir; rolipram; RP 73401; peptide T; MDL 201,449A; (1R,3S)-Cis-1-[9-(2,6-diamin-opurinyl)]-3-hydroxy-4-cyclopentene hydrochloride; (1R,3R)-trans-1-[9-(2,6-diamino)purine]-3-acetoxycyclopentane; (1R,3R)-trans-1-[9-adenyl)-3-azido-cyclopentane hydrochloride and (1R,3R)-trans-1-[6-hydroxy-purin-9-yl)-3-az-idocyclopentane.

It has been found that IL-4 can induce an inflammatory effect in some instances, such as in asthma, in which overexpression of IL-4 in the lungs causes epithelial cell hypertrophy and an accumulation of lymphocytes, eosinophils, and neutrophils. This response is representative of the main features of the proinflammatory response induced by other Th2 cytokines. As noted above, therefore, inhibitors of IL-4 are also useful in accordance with the invention. Additionally, it will be appreciated that certain immunosuppressant drugs can also be used in the treatment of arthritis, including, but not limited to, iNOS inhibitors, and 5-lipoxygenase inhibitors.

Ginger has been shown to have certain anti-inflammatory properties, and is therefore suitable for use as an anti-inflammatory agent in accordance with the invention, as is chondroitin.

Pharmaceutical compositions of the invention also can be administered in combination therapy, i.e., combined with other agents. For example, the combination therapy can include a composition of the present invention with at least one anti-tumor agent or other conventional therapy. The antibodies and antigen-binding regions thereof can be utilized in combination with other therapeutics in the treatment of diseases associated with uPA activation. These other therapeutics include, for example radiation treatment, chemotherapy, and targeted therapies such as Herceptin™, Rituxan™, Gleevec™, and the like. Additional combination therapies not specifically listed herein are also within the scope of the present invention.

In another embodiment, the human anti-uPA antibodies, or antigen binding fragments thereof, can be co-administered with a therapeutic agent, e.g., an anti-angiogenic agent, a chemotherapeutic agent, an immunosuppressive agent, an ant-inflammatory agent, or an anti-psoriasis agent, or can be co-administered with other known therapies, such as physical therapies, e.g., radiation therapy, hyperthermia, transplantation (e.g., bone marrow transplantation), surgery, sunlight, or phototherapy. Such therapeutic agents include, among others, anti-neoplastic agents such as doxorubicin (adriamycin), cis-platin bleomycin sulfate, carmustine, chlorambucil, and cyclophosphamide hydroxyurea which, by themselves, are only effective at levels which are toxic or subtoxic to a patient. Cisplatin is intravenously administered as a 100 mg/m$^2$ dose once every four weeks and adriamycin is intravenously administered as a 60-75 mg/m$^2$ dose once every 21 days.

Pharmaceutical compositions of the present invention can include one or more further anti-angiogenic agents selected from the group consisting of antagonists of Ang-1 and uPA (and their receptors), VEGF (Avastin, VEGF-TRAP, etc.), VEGF receptors, and IL-8, B-FGF, and small molecule inhibitors of KDR and other mediators of inflammation. Inhibitors of inflammation include such compounds as: SD-7784 (Pfizer, USA); cilengitide (Merck KGaA, Germany, EPO 770622); pegaptanib octasodium, (Gilead Sciences, USA); Alphastatin, (BioActa, UK); M-PGA, (Celgene, USA, U.S. Pat. No. 5,712,291); ilomastat, (Arriva, USA, U.S. Pat. No. 5,892,112); emaxanib, (Pfizer, USA, U.S. Pat. No. 5,792,783); vatalanib, (Novartis, Switzerland); 2-methoxyestradiol, (EntreMed, USA); TLC ELL-12, (Elan, Ireland); anecortave acetate, (Alcon, USA); alpha-D148 Mab, (Amgen, USA); CEP-7055, (Cephalon, USA); anti-Vn Mab, (Crucell, Netherlands) DAC:antiangiogenic, (ConjuChem, Canada); Angiocidin, (InKine Pharmaceutical, USA); KM-2550, (Kyowa Hakko, Japan); SU-0879, (Pfizer, USA); CGP-79787, (Novartis, Switzerland, EP 970070); ARGENT technology, (Ariad, USA); YIGSR-Stealth, (Johnson & Johnson, USA); fibrinogen-E fragment, (BioActa, UK); inflammation inhibitor, (Trigen, UK); TBC-1635, (Encysive Pharmaceuticals, USA); SC-236, (Pfizer, USA); ABT-567, (Abbott, USA); Metastatin, (EntreMed, USA); inflammation inhibitor, (Tripep, Sweden); maspin, (Sosei, Japan); 2-methoxyestradiol, (Oncology Sciences Corporation, USA); ER-68203-00, (IVAX, USA); Benefin, (Lane Labs, USA); Tz-93, (Tsumura, Japan); TAN-1120, (Takeda, Japan); FR-111142, (Fujisawa, Japan, JP 02233610); platelet factor 4, (RepliGen, USA, EP 407122); vascular endothelial growth factor antagonist, (Borean, Denmark); cancer therapy, (University of South Carolina, USA); bevacizumab (pINN), (Genentech, USA); inflammation inhibitors, (SUGEN, USA); XL 784, (Exelixis, USA); XL 647, (Exelixis, USA); MAb, alpha5beta3 integrin, second generation, (Applied Molecular Evolution, USA and MedImmune, USA); gene therapy, retinopathy, (Oxford BioMedica, UK); enzastaurin hydrochloride (USAN), (Lilly, USA); CEP 7055, (Cephalon, USA and Sanofi-Synthelabo, France); BC 1, (Genoa Institute of Cancer Research, Italy); inflammation inhibitor, (Alchemia, Australia); VEGF antagonist, (Regeneron, USA); rBPI 21 and BPI-derived antiangiogenic, (XOMA, USA); PI 88, (Progen, Australia); cilengitide (pNN), (Merck KGaA, German; Munich Technical University, Germany, Scripps Clinic and Research Foundation, USA); cetuximab (INN), (Aventis, France); AVE 8062, (Ajinomoto, Japan); AS 1404, (Cancer Research Laboratory, New Zealand); SG 292, (Telios, USA); Endostatin, (Boston Childrens Hospital, USA); ATN 161, (Attenuon, USA); ANGIOSTATIN, (Boston Childrens Hospital, USA); 2-methoxyestradiol, (Boston Childrens Hospital, USA); ZD 6474, (AstraZeneca, UK); ZD 6126, (Angiogene Pharmaceuticals, UK); PPI 2458, (Praecis, USA); AZD 9935, (AstraZeneca, UK); AZD 2171, (AstraZeneca, UK); vatalanib (pINN), (Novartis, Switzerland and Schering AG, Germany); tissue factor pathway inhibitors, (EntreMed, USA); pegaptanib (Pinn), (Gilead Sciences, USA); xanthorrhizol, (Yonsei University, South Korea); vaccine, gene-based, VEGF-2, (Scripps Clinic and Research Foundation, USA); SPV5.2, (Supratek, Canada); SDX 103, (University of California at San Diego, USA); PX 478, (ProIX, USA); METASTATIN, (EntreMed, USA); troponin I, (Harvard University, USA); SU 6668, (SUGEN, USA); OXI 4503, (OXIGENE, USA); o-guanidines, (Dimensional Pharmaceuticals, USA); motuporamine C, (British Columbia University, Canada); CDP 791, (Celltech Group, UK); atiprimod (pINN), (GlaxoSmithKline, UK); E 7820, (Eisai, Japan); CYC 381, (Harvard University, USA); AE 941, (Aeterna, Canada); vaccine, inflammation, (EntreMed, USA); urokinase plasminogen activator inhibitor, (Dendreon, USA); oglufanide (pINN), (Melmotte, USA); HIF-1alfa inhibitors, (Xenova, UK); CEP 5214, (Cephalon, USA); BAY RES 2622, (Bayer, Germany); Angiocidin, (InKine, USA); A6, (Angstrom, USA); KR 31372, (Korea Research Institute of Chemical Technology, South Korea); GW 2286, (GlaxoSmithKline, UK); EHT 0101, (ExonHit, France); CP 868596, (Pfizer, USA); CP 564959, (OSI, USA); CP 547632, (Pfizer, USA); 786034, (GlaxoSmithKline, UK); KRN 633, (Kirin Brewery, Japan); drug delivery system, intraocular, 2-methoxyestradiol, (EntreMed, USA); anginex, (Maastricht University, Netherlands, and Minnesota University, USA); ABT 510, (Abbott, USA); AAL 993, (Novartis, Switzerland); VEGI, (ProteomTech, USA); tumor necrosis factor-alpha inhibitors, (National Institute on Aging, USA); SU 11248, (Pfizer, USA and SUGEN USA); ABT 518, (Abbott, USA); YH16, (Yantai Rongchang, China); S-3APG, (Boston Childrens Hospital, USA and EntreMed, USA); MAb, KDR, (ImClone Systems, USA); MAb, alpha5 beta1, (Protein. Design, USA); KDR kinase inhibitor, (Celltech Group, UK, and Johnson & Johnson, USA); GFB 116, (South Florida University, USA and Yale University, USA); CS 706, (Sankyo, Japan); combretastatin A4 prodrug, (Arizona State University, USA); chondroitinase AC, (IBEX, Canada); BAY RES 2690, (Bayer, Germany); AGM 1470, (Harvard University, USA, Takeda, Japan, and TAP, USA); AG 13925, (Agouron, USA); Tetrathiomolybdate, (University of Michigan, USA); GCS 100, (Wayne State University, USA) CV 247, (Ivy Medical, UK); CKD 732, (Chong Kun Dang, South Korea); MAb, vascular endothelium growth factor, (Xenova, UK); irsogladine (INN), (Nippon Shinyaku, Japan); RG 13577, (Aventis, France); WX 360, (Wilex, Germany); squalamine (pINN), (Genaera, USA); RPI 4610, (Sirna, USA); cancer therapy, (Marinova, Australia); heparanase inhibitors, (InSight, Israel); KL 3106, (Kolon, South Korea); Honokiol, (Emory University, USA); ZK CDK, (Schering AG, Germany); ZK Angio, (Schering AG, Germany); ZK 229561, (Novartis, Switzerland, and Schering AG, Germany); XMP 300, (XOMA, USA); VGA 1102, (Taisho, Japan); VEGF receptor modulators, (Pharmacopeia, USA); VE-cadherin-2 antagonists (ImClone Systems, USA); Vasostatin, (National Institutes of Health, USA); vaccine, Flk-1, (ImClone Systems, USA); TZ 93, (Tsumura, Japan); TumStatin, (Beth Israel Hospital, USA); truncated soluble FLT 1 (vascular endothelial growth factor receptor 1), (Merck & Co, USA); Tie-2 ligands, (Regeneron, USA); thrombospondin 1 inhibitor, (Allegheny Health, Education and Research Foundation, USA).

The pharmaceutical compositions of the present invention can also include one or more inhibitors of growth factor agents, such as antagonists of hepatocyte growth factor (HGF, also known as Scatter Factor, and its receptor "c-met").

Target-specific effector cells, e.g., effector cells linked to compositions (e.g., human antibodies, multispecific and bispecific molecules) of the invention can also be used as therapeutic agents. Effector cells for targeting can be human leukocytes such as macrophages, neutrophils or monocytes. Other cells include eosinophils, natural killer cells and other IgG- or IgA-receptor bearing cells. If desired, effector cells can be obtained from the subject to be treated. The target-specific effector cells, can be administered as a suspension of cells in a physiologically acceptable solution. The number of cells administered can be in the order of $10^8$-$10^9$ but will vary depending on the therapeutic purpose. In general, the amount will be sufficient to obtain localization at the target cell, e.g., a tumor cell expressing uPA, and to effect cell killing by, e.g., phagocytosis. Routes of administration can also vary.

Therapy with target-specific effector cells can be performed in conjunction with other techniques for removal of targeted cells. For example, anti-tumor therapy using the compositions (e.g., human antibodies, multispecific and bispecific molecules) of the invention and/or effector cells armed with these compositions can be used in conjunction with chemotherapy. Additionally, combination immunotherapy may be used to direct two distinct cytotoxic effector populations toward tumor cell rejection. For example, anti-uPA antibodies linked to anti-FcγRi or anti-CD3 may be used in conjunction with IgG- or IgA-receptor specific binding agents.

Bispecific and multispecific molecules of the invention can also be used to modulate FcαR or FcγR levels on effector cells, such as by capping and elimination of receptors on the cell surface. Mixtures of anti-Fc receptors can also be used for this purpose.

The compositions (e.g., human antibodies, multispecific and bispecific molecules) of the invention which have complement binding sites, such as portions from IgG1, IgG2, IgG3 or IgM which bind complement, can also be used in the presence of complement. In one embodiment, ex vivo treatment of a population of cells comprising target cells with a binding agent of the invention and appropriate effector cells can be supplemented by the addition of complement or serum containing complement. Phagocytosis of target cells coated with a binding agent of the invention can be improved by binding of complement proteins. In another embodiment target cells coated with the compositions (e.g., human antibodies, multispecific and bispecific molecules) of the invention can also be lysed by complement. In yet another embodiment, the compositions of the invention do not activate complement.

The compositions (e.g., human antibodies, multispecific and bispecific molecules) of the invention can also be administered together with complement. Accordingly, within the scope of the invention are compositions comprising human antibodies, multispecific or bispecific molecules and serum or complement. These compositions are advantageous in that the complement is located in close proximity to the human antibodies, multispecific or bispecific molecules. Alternatively, the human antibodies, multispecific or bispecific molecules of the invention and the complement or serum can be administered separately.

Also within the scope of the invention are kits comprising the compositions (e.g., human antibodies, multispecific and bispecific molecules) of the invention and instructions for use. The kit can further contain a least one additional reagent, such as complement, or one or more additional human antibodies of the invention (e.g., a human antibody having a complementary activity which binds to an epitope in uPA antigen distinct from the first human antibody).

In other embodiments, the subject can be additionally treated with an agent that modulates, e.g., enhances or inhibits, the expression or activity of Fcα or Fcγ receptors by, for example, treating the subject with a cytokine. Preferred cytokines for administration during treatment with the multispecific molecule include of granulocyte colony-stimulating factor (G-CSF), granulocyte-macrophage colony-stimulating factor (GM-CSF), interferon-γ (IFN-γ), and tumor necrosis factor (TNF).

In another embodiment, the subject can be additionally treated with a lymphokine preparation. Cancer cells which do not highly express uPA can be induced to do so using lymphokine preparations. Lymphokine preparations can cause a more homogeneous expression of uPAs among cells of a tumor which can lead to a more effective therapy. Lymphokine preparations suitable for administration include interferon-gamma, tumor necrosis factor, and combinations thereof. These can be administered intravenously. Suitable dosages of lymphokine are 10,000 to 1,000,000 units/patient.

The compositions (e.g., human antibodies, multispecific and bispecific molecules) of the invention can also be used to target cells expressing FcγR or uPA, for example for labeling such cells. For such use, the binding agent can be linked to a molecule that can be detected. Thus, the invention provides methods for localizing ex vivo or in vitro cells expressing Fc receptors, such as FcγR, or uPA. The detectable label can be, e.g., a radioisotope, a fluorescent compound, an enzyme, or an enzyme co-factor.

In one embodiment, the invention provides methods for detecting the presence of uPA antigen in a sample, or measuring the amount of uPA antigen, comprising contacting the sample, and a control sample, with a human monoclonal antibody, or an antigen-binding region thereof, which specifically binds to uPA, under conditions that allow for formation of a complex between the antibody or portion thereof and uPA. The formation of a complex is then detected, wherein a difference complex formation between the sample compared to the control sample is indicative the presence of uPA antigen in the sample.

In still another embodiment, the invention provides a method for detecting the presence or quantifying the amount of Fc-expressing cells in vivo or in vitro. The method comprises (i) administering to a subject a composition (e.g., a multi- or bispecific molecule) of the invention or a fragment thereof, conjugated to a detectable marker; (ii) exposing the subject to a means for detecting said detectable marker to identify areas containing Fc-expressing cells.

Uses and Methods of the Invention

The present invention provides antibodies or antigen-binding regions thereof that bind to uPA epitopes that are useful for the treatment of human diseases and pathological conditions. Agents that activate uPA activity, or other cellular activity, may be used in combination with other therapeutic agents to enhance their therapeutic effects or decrease potential side effects.

In one aspect, the present invention provides reagents and methods useful for treating diseases and conditions characterized by undesirable or aberrant levels of uPA activity in a cell. These diseases include inflammation, including such inflammatory conditions as acute lung inflammation, and sepsis.

The compositions (e.g., human antibodies, multispecific and bispecific molecules) of the invention can be initially tested for binding activity associated with therapeutic or diagnostic use in vitro. For example, compositions of the invention can be tested using the ELISA and flow cytometric assays described herein. Moreover, the activity of these molecules in triggering at least one effector-mediated effector cell activity, including cytolysis of cells expressing uPA can be assayed. Protocols for assaying for effector cell-mediated phagocytosis are described herein.

The compositions (e.g., human antibodies, multispecific and bispecific molecules) of the invention have additional utility in therapy and diagnosis of uPA-related diseases. For example, the human monoclonal antibodies, the multispecific or bispecific molecules can be used to inhibit inflammation caused by a cell expressing uPA. The anti-uPA antibodies of the present invention may be useful in treating any inflammation-dependant disease, including, but not limited to, ocular neovascularisation, such as retinopathies (including diabetic retinopathy), age-related macular degeneration, psoriasis, hemangioblastoma, hemangioma, arteriosclerosis, inflammatory disease, such as a rheumatoid or rheumatic inflammatory disease, especially arthritis (including rheumatoid arthritis), or other chronic inflammatory disorders, such as chronic asthma, arterial or post-transplantational atherosclerosis, endometriosis, and neoplastic diseases, for example, so-called solid tumors and liquid (or hematopoietic) tumors (such as leukemias and lymphomas). Other diseases associated with undesired inflammation will be apparent to those skilled in the art.

Other aspects of the present invention include treating various retinopathies (including diabetic retinopathy and age-related macular degeneration) in which inflammation is involved, as well as disorders/diseases of the female reproductive tract such as endometriosis, uterine fibroids, and other such conditions associated with dysfunctional vascular proliferation (including endometrial microvascular growth) during the female reproductive cycle.

Identification of uPA Epitope Binding Molecules

The uPA epitopes and antibodies of the present invention may be used to identify agents that activate uPA activity, which may be useful in treating certain physiological disorders, including, but not-limited to inhibiting inflammation. In one aspect of the present invention there is provided a method for identifying a compound that specifically binds to a human uPA epitope defined by the polypeptide sequence of SEQ ID NO:2, comprising: contacting a test compound with the human uPA epitope for a time sufficient to form a complex and detecting for the formation of a complex by detecting the uPA epitope or the compound in the complex, so that if a complex is detected, a compound that binds to the uPA epitope is identified. For example, cells transfected with DNAs coding for proteins of interest can be treated with various drugs, and co-immunoprecipitations can be performed. Because uPA is involved in transducing physiological signals associated with activation of such physiological disorders as inflammation, the identification of agents which are capable of inhibiting uPA activity will provide agents which can be used to treat physiological disorder or to use lead compounds for development of therapeutic agents. An agent may inhibit uPA by binding to the uPA epitopes defined herein in such a manner that the agent inhibits binding of uPA to its receptors. Agents which may be used to inhibit uPA include peptides, antibodies, nucleic acids, antisense compounds or ribozymes. The nucleic acid may encode the antibody or the antisense compound. The peptide may be at least 4 amino acids of the sequence of the binding protein. Alternatively, the peptide may be from 4 to 30 amino acids (or from 8 to 20 amino acids) that is at least 75% identical to a contiguous span of amino acids of the binding protein. Agents can be tested using transfected host cells, cell lines, cell models or animals, such as described herein, by techniques well known to those of ordinary skill in the art, such as disclosed in U.S. Pat. Nos. 5,622,852 and 5,773,218, and PCT published application Nos. WO 97/27296 and WO 99/65939, each of which are incorporated herein by reference. The modulating effect of the agent can be tested in vivo or in vitro. Agents can be provided for testing in a phage display library or a combinatorial library. Exemplary of a method to screen agents is to measure the effect that the agent has on the formation of the protein complex.

The uPA epitopes of the present invention may also be used to produce structural analogs of biologically active polypeptides of interest or of small molecules with which they interact (e.g., agonists, antagonists, inhibitors) in order to fashion drugs which are, for example, more active or stable forms of the polypeptide, or which, e.g., enhance or interfere with the function of a polypeptide in vivo. One aspect of the present invention provides a method for identifying a compound that specifically binds to a human uPA epitope defined by the polypeptide sequence of SEQ ID NO:2 comprising: providing atomic coordinates defining a three-dimensional structure of a uPA epitope defined by the polypeptide sequence of SEQ ID NO:2, and designing or selecting compounds capable of binding the uPA epitope based on said atomic coordinates. Several approaches for use in rational drug design include analysis of three-dimensional structure, alanine scans, molecular modeling and use of anti-id antibodies. These techniques are well known to those skilled in the art. Such techniques may include providing atomic coordinates defining a three-dimensional structure of a protein complex formed by said first polypeptide and said second polypeptide, and designing or selecting compounds capable of interfering with the interaction between a first polypeptide and a second polypeptide based on said atomic coordinates.

Following identification of a substance which modulates or affects polypeptide activity, the substance may be further investigated. Furthermore, it may be manufactured and/or used in preparation, i.e., manufacture or formulation, or a composition such as a medicament, pharmaceutical composition or drug. These may be administered to individuals.

A substance identified as a modulator of polypeptide function may be peptide or non-peptide in nature. Non-peptide "small molecules" are often preferred for many in vivo pharmaceutical uses. Accordingly, a mimetic or mimic of the substance (particularly if a peptide) may be designed for pharmaceutical use.

The designing of mimetic to a known pharmaceutically active compound is a known approach to the development of pharmaceuticals based on a "lead" compound. This approach might be desirable where the active compound is difficult or expensive to synthesize or where it is unsuitable for a particular method of administration, e.g., pure peptides are unsuitable active agents for oral compositions as they tend to be quickly degraded by proteases in the alimentary canal. Mimetic design, synthesis and testing is generally used to avoid randomly screening large numbers of molecules for a target property.

Once the pharmacophore has been found, its structure is modeled according to its physical properties, e.g., stereochemistry, bonding, size and/or charge, using data from a range of sources, e.g., spectroscopic techniques, x-ray diffraction data and NMR. Computational analysis, similarity mapping (which models the charge and/or volume of a pharmacophore, rather than the bonding between atoms) and other techniques can be used in this modeling process.

A template molecule is then selected, onto which chemical groups that mimic the pharmacophore can be grafted. The template molecule and the chemical groups grafted thereon can be conveniently selected so that the mimetic is easy to synthesize, is likely to be pharmacologically acceptable, and does not degrade in vivo, while retaining the biological activity of the lead compound. Alternatively, where the mimetic is peptide-based, further stability can be achieved by cyclizing the peptide, increasing its rigidity. The mimetic or mimetics found by this approach can then be screened to see whether they have the target property, or to what extent it is exhibited. Further optimization or modification can then be carried out to arrive at one or more final mimetics for in vivo or clinical testing.

Assays to Screen for Inhibitors or Activators of uPA

In some situations, it may be desirable to inhibit or significantly decrease the level of uPA activity. For instance, inhibiting or reducing the level of uPA activity may be useful in reducing inflammation. Compounds that inhibit uPA activity could be administered either in an ex vivo manner, or in an in vivo manner by subcutaneous or intravenous (i.v.) injection, or by oral delivery, implantation device, or the like. The assays described below exemplify methods useful for identifying compounds that inhibit uPA activity.

For ease of reading, the term "test molecule(s)" is used to refer to the molecule(s) that is under evaluation as an inhibitor of uPA KD, typically by virtue of its potential ability to block the interaction of uPA KD with its receptor proteins. The term "receptor" means molecules to which uPD KD bind, including antibodies, as disclosed herein.

Several types of in vitro assays using purified uPA protein or polypeptide may be conducted to identify those compounds that perturb uPA activity. Such a perturbation may be accomplished by compounds that for example inhibit the interaction of uPA with its receptor proteins.

In one such assay, purified uPA KD protein or a fragment thereof (prepared for example using methods described above), can be immobilized by attachment to the bottom of the wells of a microtiter plate. Radiolabeled receptor protein, as well as the test molecule(s) can then be added either one at a time or simultaneously to the wells. After incubation, the wells can be washed and counted using a scintillation counter for radioactivity to determine the degree of uPA KD/receptor protein binding in the presence of the test molecule. Typically, the molecule will be tested over a range of concentrations, and a series of control "wells" lacking one or more elements of the test assays are used for accuracy in evaluating the results. A variation of this assay involves attaching the receptor protein to the wells, and adding radiolabeled uPA along with the test molecule to the wells. After incubation and washing, the wells can be counted for radioactivity. Test compounds to decrease the binding of receptor protein to uPA represent one class of inhibitors of uPA activity.

Several means are available to "detectably label" uPA. For example, uPA protein can be radiolabeled using sup.125I. Alternatively, a fusion protein of uPA may be used wherein the DNA encoding uPA is fused to the coding sequence of a peptide such as the c-myc epitope. uPA-myc fusion protein can readily be detected with commercially available antibodies directed against myc. The uPA protein may also be modified by fusion with an immunoglobulin or fragment thereof (e.g. Fc fragment), which may be detected for example by well known methods. Other markers or labels include chromogenic or fluorogenic markers.

An alternative to microtiter plate type of binding assays comprises immobilizing either uPA or receptor protein on agarose beads, acrylic beads or other types of such inert substrates. The inert substrate to which the uPA or receptor protein is attached placed in a solution containing the test molecule along with the complementary component (either receptor protein or uPA protein), which has been radiolabeled or fluorescently labeled; after incubation, the inert substrate can be collected by centrifugation, and the amount of binding between uPA and receptor protein can be readily assessed using the methods described above. Alternatively, the inert substrate complex can be immobilized in a column and the test molecule and complementary component passed over the column. Formation of the uPA/receptor protein complex can then be assessed using any of the techniques set forth above, i.e., radiolabeling, antibody binding, or the like.

Another type of in vitro assay that is useful for identifying a molecule to inhibit uPA activity is the Biacore Assay System (Pharmacia, Piscataway, N.J.), using a surface plasmon resonance detector system and following the manufacturer's protocol. This assay essentially involves covalent binding of either uPA or receptor protein to a dextran-coated sensor chip which is located in a detector. The test molecule and the complementary component can then be injected into the chamber containing the sensor chip either simultaneously or sequentially, and the amount of binding of uPA/receptor protein can be assessed based on the change in molecular mass which is physically associated with the dextran-coated side of the of the sensor chip; the change in molecular mass can be measured by the detector system.

In some cases, it may be desirable to evaluate two or more test molecules together for use in decreasing or inhibiting uPA activity. In these cases, the assays set forth above can be readily modified by adding such additional test molecule(s)

either simultaneously with, or subsequently to, the first test molecule. The remainder of steps in the assay can be as set forth above.

Additional assays may be used to determine whether test molecules can disrupt uPA/receptor protein interaction in cell lines. For example, as noted above, uPA is more highly expressed in tumor cell lines than in normally proliferating cell lines. According to certain embodiments, one may expose a cell line that highly expresses uPA and expresses receptor protein to test molecules to determine whether uPA/receptor protein binding is reduced, whether the production of uPA in the cell line is reduced, and/or proliferation of the cell line is reduced. One can compare the effects of the test molecule by comparing these factors (effect on uPA/receptor protein binding, production of uPA, and/or proliferation of the cell line), in the test cell line (i.e. the one exposed to the test molecule), to a control cell line that is not exposed to the test molecule.

For determining the effect on uPA/receptor protein binding or uPA production, one can remove proteins from the cell or sample and use methods similar to those above that tag or isolate uPA/receptor protein complexes or uPA. For example, one could use immunoaffinity purification technique, which may or may not include the use of fusion constructs for the uPA and receptor.

Similarly, one can use a transgenic animal that over expresses uPA and expresses receptor protein to determine whether test molecules reduce uPA/receptor protein binding, reduce production of uPA in the transgenic animal, and/or reduce inflammation in the transgenic animal. Conversely, assays may also be used to screen for activators of uPA activity. Such compounds may be useful in inhibiting uPA mediated inflammation in vitro and in vivo. A person of ordinary skill in the art would readily recognize that several of the foregoing assays which measure the inhibition of uPA may be readily adapted to measure increases in uPA activity. Activators of uPA gene transcription may readily determined using techniques such as reverse transcriptase-polymerase chain reaction techniques, RNAse protection assays and the like. Increased levels of uPA protein are also readily determined by well known techniques such as immuno-affinity techniques.

Binding Assays

Immunological binding assays typically utilize a capture agent to bind specifically to and often immobilize the analyte target antigen. The capture agent is a moiety that specifically binds to the analyte. In one embodiment of the present invention, the capture agent is an antibody or antigen-binding region thereof that specifically binds the uPA epitopes of the invention. These immunological binding assays are well known in the art [Asai, ed., Methods in Cell Biology, Vol. 37, Antibodies in Cell Biology, Academic Press, Inc., New York (1993)].

Immunological binding assays frequently utilize a labeling agent that will signal the existence of the bound complex formed by the capture agent and antigen. The labeling agent can be one of the molecules comprising the bound complex; i.e. it can be a labeled specific binding agent or a labeled anti-specific binding agent antibody. Alternatively, the labeling agent can be a third molecule, commonly another antibody, which binds to the bound complex. The labeling agent can be, for example, an anti-specific binding agent antibody bearing a label. The second antibody, specific for the bound complex, may lack a label, but can be bound by a fourth molecule specific to the species of antibodies which the second antibody is a member of. For example, the second antibody can be modified with a detectable moiety, such as biotin, which can then be bound by a fourth molecule, such as enzyme-labeled streptavidin. Other proteins capable of specifically binding immunoglobulin constant regions, such as protein A or protein G may also be used as the labeling agent. These binding proteins are normal constituents of the cell walls of streptococcal bacteria and exhibit a strong non-immunogenic reactivity with immunoglobulin constant regions from a variety of species. Akerstrom, *J. Immunol.* 135:2589-2542 (1985); Chaubert, *Mod Pathol.* 10:585-591 (1997).

Throughout the assays, incubation and/or washing steps may be required after each combination of reagents. Incubation steps can vary from about 5 seconds to several hours, preferably from about 5 minutes to about 24 hours. However, the incubation time will depend upon the assay format, analyte, volume of solution, concentrations, and the like. Usually, the assays will be carried out at ambient temperature, although they can be conducted over a range of temperatures.

A. Non-Competitive Binding Assays:

Immunological binding assays can be of the non-competitive type. These assays have an amount of captured analyte that is directly measured. For example, in one preferred "sandwich" assay, the capture agent (antibody) can be bound directly to a solid substrate where it is immobilized. These immobilized capture agents then capture (bind to) antigen present in the test sample. The protein thus immobilized is then bound to a labeling agent, such as a second antibody having a label. In another preferred "sandwich" assay, the second antibody lacks a label, but can be bound by a labeled antibody specific for antibodies of the species from which the second antibody is derived. The second antibody also can be modified with a detectable moiety, such as biotin, to which a third labeled molecule can specifically bind, such as streptavidin. See Harlow and Lane, Antibodies, A Laboratory Manual, Ch 14, Cold Spring Harbor Laboratory, N.Y. (1988), incorporated herein by reference.

B. Competitive Binding Assays:

Immunological binding assays can be of the competitive type. The amount of analyte present in the sample is measure indirectly by measuring the amount of an added analyte displaced, or competed away, from a capture agent (antibody) by the analyte present in the sample. In one preferred competitive binding assay, a known amount of analyte, usually labeled, is added to the sample and the sample is then contacted with the capture agent. The amount of labeled analyze bound to the antibody is inversely proportional to the concentration of analyte present in the sample (See, Harlow and Lane, Antibodies, A Laboratory Manual, Ch 14, pp. 579-583, supra).

In another preferred competitive binding assay, the capture agent is immobilized on a solid substrate. The amount of protein bound to the capture agent may be determined either by measuring the amount of protein present in a protein/antibody complex, or alternatively by measuring the amount of remaining uncomplexed protein. The amount of protein may be detected by providing a labeled protein. Harlow and Lane (supra).

Yet another preferred competitive binding assay, hapten inhibition is utilized. Here, a known analyte is immobilized on a solid substrate. A known amount of antibody is added to the sample, and the sample is contacted with the immobilized analyte. The amount of antibody bound to the immobilized analyte is inversely proportional to the amount of analyte present in the sample. The amount of immobilized antibody may be detected by detecting either the immobilized fraction of antibody or the fraction that remains in solution. Detection may be direct where the antibody is labeled or indirect by the subsequent addition of a labeled moiety that specifically binds to the antibody as described above.

C. Utilization of Competitive Binding Assays:

The competitive binding assays can be used for cross-reactivity determinations to permit a skilled artisan to determine if a protein or enzyme complex which is recognized by a peptibody of the invention is the desired protein and not a cross-reacting molecule or to determine whether the peptibody is specific for the antigen and does not bind unrelated antigens. In assays of this type, antigen can be immobilized to a solid support and an unknown protein mixture is added to the assay, which will compete with the binding of the peptibodies to the immobilized protein. The competing molecule also binds one or more antigens unrelated to the antigen. The ability of the proteins to compete with the binding of the peptibodies to the immobilized antigen is compared to the binding by the same protein that was immobilized to the solid support to determine the cross-reactivity of the protein mix.

D. Other Binding Assays

The present invention also provides Western blot methods to detect or quantify the presence of a uPA epitope or fragment thereof in a sample. The technique generally comprises separating sample proteins by gel electrophoresis on the basis of molecular weight and transferring the proteins to a suitable solid support, such as nitrocellulose filter, a nylon filter, or derivatized nylon filter. The sample is incubated with antibodies or antigen-binding regions thereof that specifically bind a uPA epitope and the resulting complex is detected. These peptibodies may be directly labeled or alternatively may be subsequently detected using labeled antibodies that specifically bind to the peptibody.

E. Diagnostic Assays

The derivative binding agents, such as peptides and peptibodies or fragments thereof, of the present invention are useful for the diagnosis of conditions or diseases characterized by expression of uPA or subunits, or in assays to monitor patients being treated with activators of uPA, its fragments, agonists or inhibitors of uPA activity. Diagnostic assays for uPA include methods utilizing an antibody and a label to detect uPA in human body fluids or extracts of cells or tissues. The antibodies of the present invention can be used with or without modification. In a preferred diagnostic assay, the antibodies will be labeled by attaching, e.g., a label or a reporter molecule. A wide variety of labels and reporter molecules are known, some of which have been already described herein. In particular, the present invention is useful for diagnosis of human disease.

A variety of protocols for measuring uPA proteins using antibodies specific for the respective protein are known in the art. Examples include enzyme-linked immunosorbent assay (ELISA), radioimmunoassay (RIA) and fluorescence activated cell sorting (FACS). A two-site, monoclonal-based immunoassay utilizing monoclonal antibodies reactive to two non-interfering epitopes on uPA is preferred, but a competitive binding assay can be employed. These assays are described, for example, in Maddox et al., *J. Exp. Med.* 158: 1211 (1983).

In order to provide a basis for diagnosis, normal or standard values for human uPA expression are usually established. This determination can be accomplished by combining body fluids or cell extracts from normal subjects, preferably human, with an antibody to uPA, under conditions suitable for complex formation that are well known in the art. The amount of standard complex formation can be quantified by comparing the binding of the antibodies to known quantities of uPA protein, with both control and disease samples. Then, standard values obtained from normal samples can be compared with values obtained from samples from subjects potentially affected by disease. Deviation between standard and subject values suggests a role for uPA in the disease state.

For diagnostic applications, in certain embodiments antibodies, or antigen-binding regions thereof, of the present invention typically will be labeled with a detectable moiety. The detectable moiety can be any one that is capable of producing, either directly or indirectly, a detectable signal. For example, the detectable moiety may be a radioisotope, such as $^{3}H$, $^{4}C$, $^{32}P$, $^{35}S$, or $^{125}I$, a fluorescent or chemiluminescent compound, such as fluorescein isothiocyanate, rhodamine, or luciferin; or an enzyme, such as alkaline phosphatase, beta-galactosidase, or horseradish peroxidase. Bayer et al., *Meth. Enz.* 184: 138-163 (1990).

The present invention is further illustrated by the following examples which should not be construed as further limiting. The contents of all figures and all references, patents and published patent applications cited throughout this application are expressly incorporated herein by reference.

EXAMPLES

Example 1

Determination of uPA Epitope Responsible for Activation of LPS Induced Neutrophil Activation In this study, neutrophils that do not express uPAR were used, as well as isolated uPA domains and uPA mutants lacking specific domains, in order to delineate how proinflammatory interactions between uPA and neutrophils are mediated. These experiments showed that the uPA KD, through a uPAR independent mechanism that appears to involve integrins, is able to enhance LPS induced neutrophil activation and cytokine expression.

Mice. Male BALB/c mice, 8 to 12 wk of age, were purchased from Harlan

Sprague-Dawley (Indianapolis, 1N). Transgenic mice with a targeted deletion of uPAR (uPAR −/−) as well as control mice on the same C57B6/129 background were prepared, as described by Abraham, et al., *J. Immunol.* 170:5644 (2003), and Gyetko, et al., *J. Clin Invest* 97:1818 (1996). The genotypes of the uPAR −/− and uPAR +/+ control mice were confirmed by PCR analysis. Mice of this background (C57B6/129) are immunocompetent and have previously been demonstrated to have preservation of complement-dependent acute lung injury. The mice were kept on a 12-h light/dark cycle with free access to food and water. All experiments were conducted in accordance with institutional review board-approved protocols.

Materials. Isoflurane was obtained from Abbott Laboratories (Chicago, Ill.). *E. coli* 0111:B4 endotoxin was purchased from Sigma Chemical Co. (St. Louis, Mo.). RPMI 1640/25 mM HEPES/L-glutamine was obtained from Mediatech, Inc. (Herndon, Va.), while fetal bovine serum (FBS) and penicillin/streptomycin were purchased from Mediatech, Inc. (Herndon, Va.). Custom Cocktail antibodies and columns for neutrophil isolation were purchased from Stem Cell Technologies (Vancouver, BC). Recombinant single chain uPA (scuPA) and the isolated uPA domains and uPA mutants lacking specific domains were prepared as previously described by Nassar, et al., *J Biol Chem* 277:40499 (2002), Bdeir, et al., *Blood* 102:3600 (2003), and Haj-Yehia, et al., *Faseb J* 14:1411 (2000). The LPS concentration of the stock scuPA measured by enzyme linked immunosorbent assay (BioWittaker, Rockland, Me.) was <1 pg/ml.

Isolation of neutrophils. Neutrophils were purified from bone marrow cell suspensions as previously described by Abraham, et al., *J Immunol* 170:5644 (2003), Asehnoune, et al., *J Immunol* 172:2522 (2004), and Strassheim, et al., *Am J Physiol Cell Physiol* 286:C683 (2004). Briefly summarized, to obtain the bone marrow cell suspension, the femur and tibia of a mouse were flushed with 5 ml RPMI 1640/penicillin/ streptomycin and the cells passed through a glass wool column, and pelleted by centrifugation at 1000 rpm for 10 minutes. The cell pellets were resuspended in 0.3% FCS/PBS and then incubated with 20 µl of primary antibodies specific for cell surface markers F4/80, CD4, CD45R, CD5, and TER19 for 15 minutes, rotating at 4° C. This custom cocktail (Stem Cell Technologies, Vancouver, British Columbia) is specific for T and B cells, RBC, monocytes and macrophages. Anti-biotin tetrameric antibody complexes (100 µl) were then added, and the cells incubated for 15 minutes, rotating at 4° C. Following this, 60 µl of colloidal magnetic dextran iron particles was added to the suspension and incubated for 15 minutes, rotating at 4° C. The entire cell suspension was then placed into a column, surrounded by a magnet. The T cells, B cells, RBC, monocytes and macrophages were captured in the column, allowing the neutrophils to pass through by negative selection methods. Neutrophil purity, as determined by Wright's stained cytospin preparations, was greater than 97%. Cell viability, as determined by trypan blue exclusion, was consistently greater than 98%.

Real time quantitative RT-PCR. Quantitative RT-PCR to measure neutrophil cytokine expression was performed as previously described by Abraham, et al., *J Immunol* 170:5644 (2003), and Park, et al., *Am J Physiol Cell Physiol* 284:C870 (2003). In brief, total cellular RNA was isolated from neutrophils using the Bio-Rad Aqua Pure RNA Isolation Kit (Bio-Rad, Hercules, Calif.), as recommended by manufacturer. Real time RT-PCR was performed with specific primers and probes corresponding to the proinflammatory cytokine genes IL-1β, MIP-2, and TNF-α. For each mRNA detected, a fluorogenic probe and two primers (forward and reverse) for PCR were synthesized (Applied Biosystems, Foster City, Calif.). The internal oligonucleotide probe was labeled with the fluorescent dyes carboxyfluorescein (FAM) at the 5' end and N,N,N',N'-tetramethyl-6-carboxyrhodamine (TAMRA) at the 3' end.

For detection of murine IL-1β mRNA, the forward and reverse primers used were, respectively:

```
5'-GCTGAAAGCTCTCCACCTCAA-3',
and

5'-TCGTTGCTTGGTTCTCCTTGTA-3'.
```

The internal probe was:

```
5'-(FAM)-CAGAATATCAACCAAGTGATATTCTCCATGAGC-
(TAMRA)-3'.
```

For detection of murine MIP-2, the forward and reverse primers used were, respectively:

```
5'-TGTGACGCCCCCAGGA-3',
and

5'-AACTTTTTGACCGCCCTTGAG-3'.
```

The internal probe was:

```
5'-(FAM)-TGCGCCCAGACAGAAGTCATAGCCA-(TAMRA)-3'.
```

For detection of murine TNF-α mRNA, the forward and reverse primers used were, respectively:

```
5'-CTGTAGCCCACGTCGTAGTCAA-3',
and

5'-CTCCTGGTATGAGATAGCAAATCG-3'.
```

The internal probe was:

```
5'-(FAM)-TGCCCCGACTACGTGCTCCTCAC-(TAMRA)-3'.
```

In order to optimize the primer sets, a primer optimization experiment was performed as described in the manufacturer's protocol. Based on primer optimization, the primer and probe concentrations for IL-1β, MIP-2, and TNF-α were 200 nM for both the primers and the probe, used in each reaction with 100 ng of total cellular RNA. In each experiment, ribosomal RNA control probe, forward primer, and reverse primer (Applied Biosystems) at concentrations of 50 nM were used to normalize for the amount of RNA in each sample.

All reagents used in the one step RT-PCR reactions were purchased from Applied Biosystems. Each one step RT-PCR reaction contained a total volume of 50 µl. The RT reaction was performed for 30 min at 48° C. using MultiScribe Reverse Transcriptase (Applied Biosystems) at a final concentration of 0.25 U/µl. After the RT step, AmpliTaq Gold polymerase, (Applied Biosystems) with a final concentration of 0.025 U/µl, was activated by an increase in temperature to 95° C. for 10 min followed by 40 cycles of amplification (95° C. for 15 sec and 60° C. for 1 min) with a Gene Amp 5700 Sequence Detection System (ABI Prism, Foster City, Calif.). The amount of cytokine mRNA was determined from a standard curve with 10 fold dilutions of known amounts of target RNA for each primer and probe set. RNA amounts were determined using software provided with the Gene Amp 5700 Sequence Detection System. Quantification was determined by dividing the target amount of each cytokine sample by the amount of 18s ribosomal RNA.

Cytokine ELISA. Immunoreactive TNF-α, IL-1β, and MIP-2 were quantified using commercially available ELISA kits (R&D Systems, Minneapolis, Minn.), according to manufacturer's instructions and as described previously by Yum, et al., *J Immunol* 167:6601 (2001).

Statistical analysis. For each experimental condition, the entire group of animals was prepared and studied at the same time. Data are presented as mean±SEM for each experimental group. One way analysis of variance, the Tukey-Kramer Multiple Comparisons test (for multiple groups) or Student's t test (for comparisons between two groups) were used. P<0.05 was considered significant.

Identification of the uPA kringle domain (KD) as mediator of uPA induced neutrophil activation. In order to delineate the domain of uPA responsible for its potentiating effects on LPS-induced neutrophil activation, neutrophils were cultured with LPS and either scuPA or deletion mutants of uPA lacking the GFD or KD. As shown in FIG. 1, scuPA significantly increased expression of IL-1β mRNA in neutrophils cultured with submaximal concentrations of LPS. Similar effects of scuPA were found in potentiating the expression of TNF-α and MIP-2 mRNA in LPS stimulated neutrophils.

Figure 2:
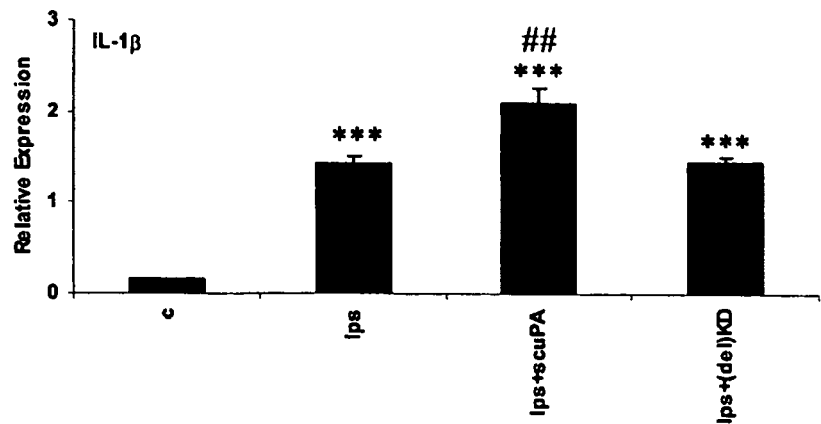
FIG. 2 indicates that the KD of uPA is required for enhancement of LPS-induced cytokine expression in neutrophils. Neutrophils were incubated without (Control) or with LPS 10 ng/ml (LPS) and scuPA or a deletion mutant of scuPA lacking the KD [(del)KD] (10 nM) for 4 hours. Cytokine mRNA levels were determined by quantitative RT-PCR normalized to GAPDH. ***$p<0.001$ versus Control. ##$p<0.01$ and ###$p<0.001$ versus LPS alone.
Figure 2:
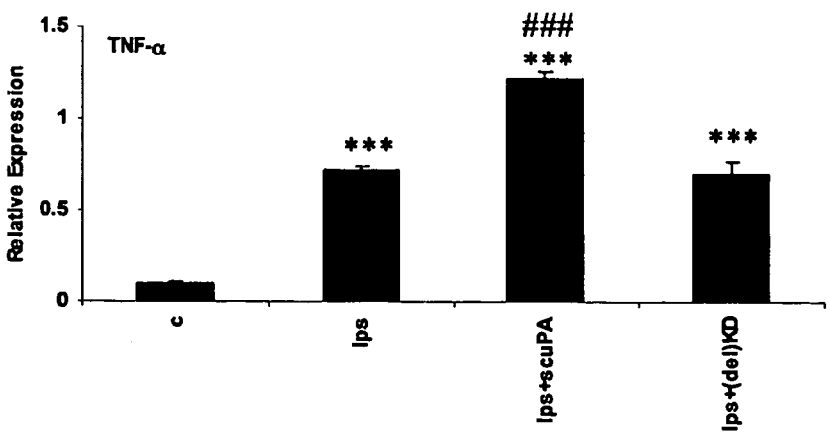
Figure 2:
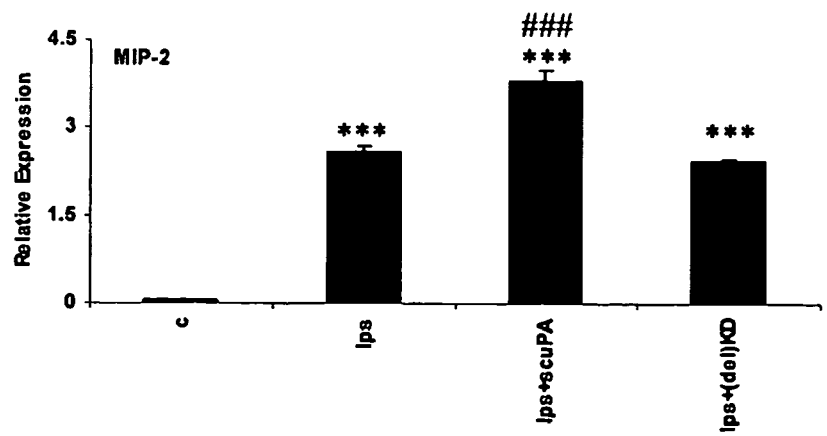

The growth factor domain (GFD) of uPA did not appear to be responsible for the proinflammatory effects of uPA since a deletion mutant lacking the uPA GFD enhanced LPS-induced cytokine mRNA expression to the same extent as did intact scuPA (FIG. 1). By contrast, deletion of the kringle domain (KD) removed the potentiating effects of uPA on these neutrophil responses (FIG. 2). These results as consistent with the KD being responsible for enhancing effects of uPA on neutrophil activation.

Figure 3:
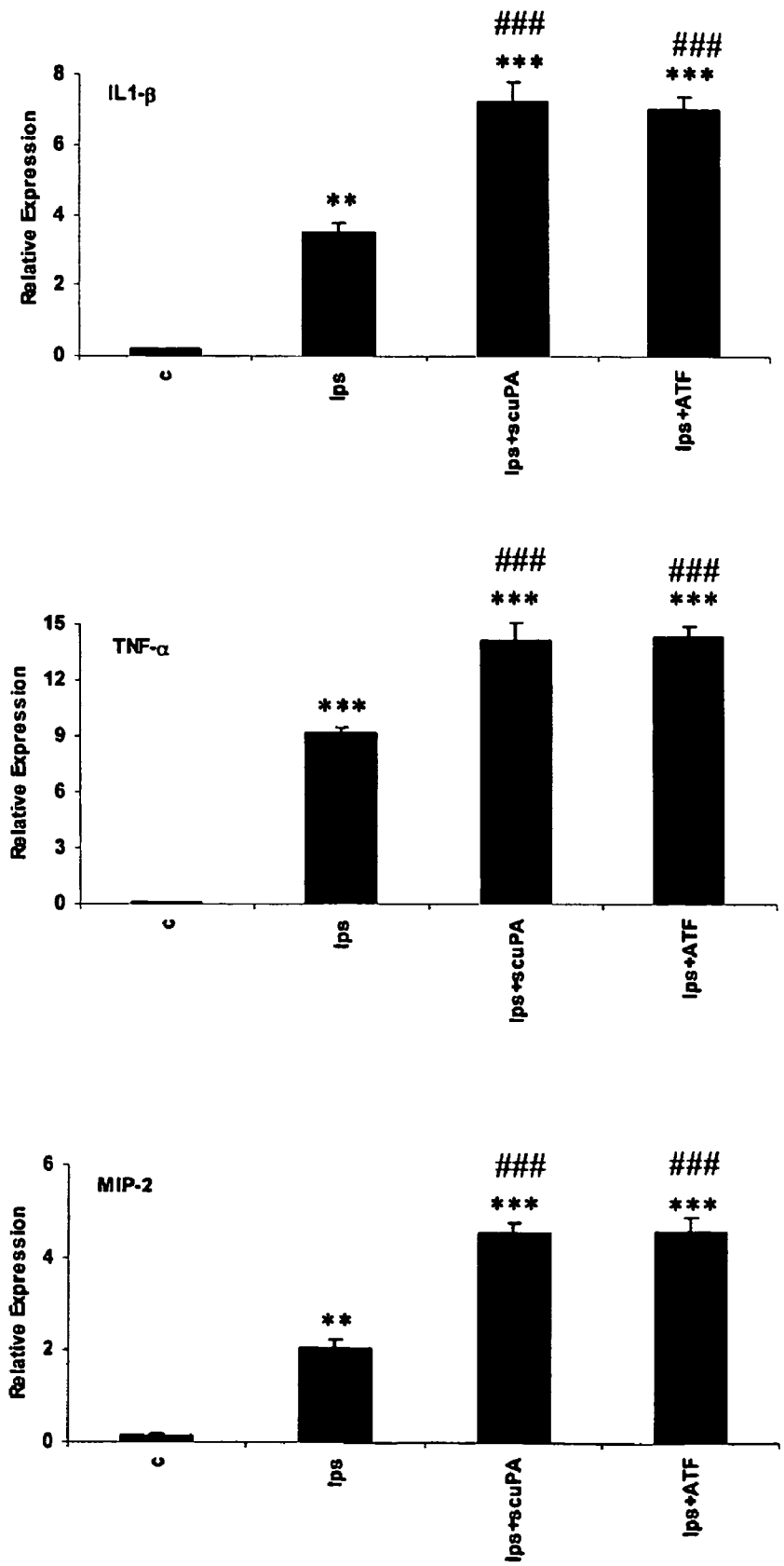
FIG. 3 indicates that purified ATS potentiates LPS-induced neutrophil activation to the same extent as does scuPA. Neutrophils were incubated without (Control) or with LPS 10 ng/ml (LPS) and scuPA or purified ATF (10 nM) for 4 hours. Cytokine mRNA levels were determined by quantitative RT-PCR normalized to GAPDH. $p<0.01$ and *$p<0.001$ versus Control. ###$p<0.001$ versus LPS alone.
Figure 4:
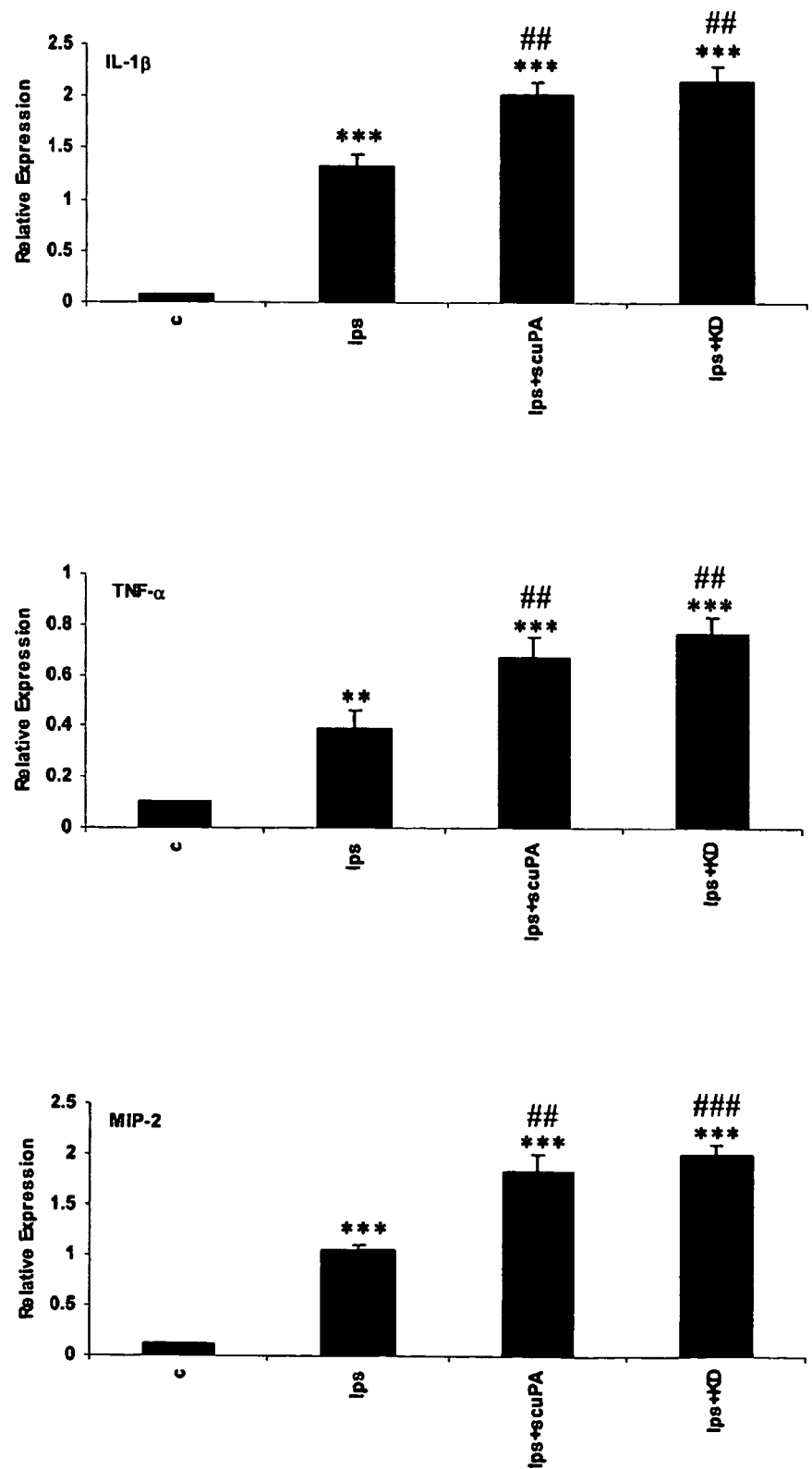
FIG. 4 indicates that purified KD of uPA produces the same degree of enhancement of LPS induced neutrophil activation as does full length uPA. Neutrophils were incubated without (Control) or with LPS 10 ng/ml (LPS) and scuPA or purified KD (10 nM) for 4 hours. Cytokine mRNA levels were determined by quantitative RT-PCR normalized to GAPDH. $p<0.01$ and *$p<0.001$ versus Control. ##$p<0.01$ and ###$p<0.001$ versus LPS alone.

The role of the KD in potentiating LPS induced neutrophil response was confirmed as follows. Purified kringle or amino terminal fragment (ATF) domains of uPA were added to LPS-stimulated neutrophils at the same concentration (10 nM) as scuPA and their potentiating effects on cytokine expression determined. Addition of the ATF, which contains the uPA GFD and KD, to neutrophils cultured with LPS enhanced IL-1β, TNF-α, and MIP-2 mRNA expression to the same extent as did scuPA (FIG. 3). These results indicate that the effects of uPA on proinflammatory cytokine expression by neutrophils are not only independent of its binding to uPAR, but also of its enzymatic activity. Similarly, exposure of LPS stimulated neutrophils to the purified uPA KD also potentiated the responses to the same extent or even a greater extent than did scuPA (FIG. 4).

Figure 5:
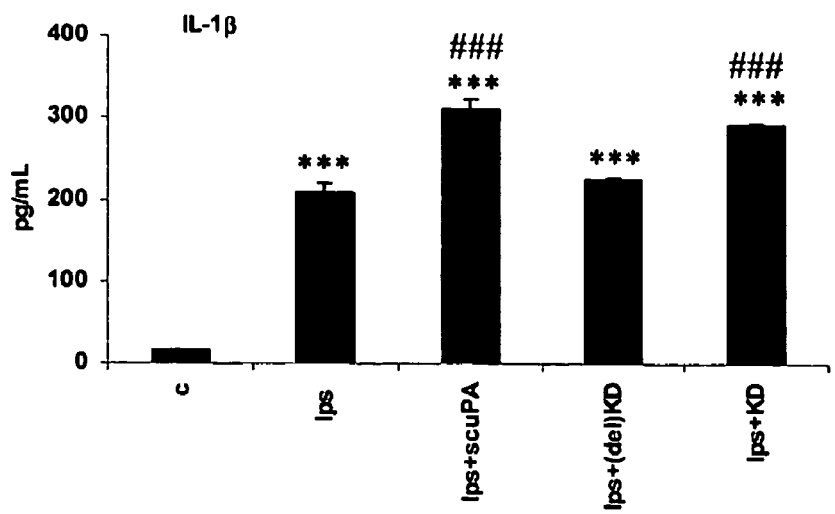
FIG. 5 shows that production of cytokines by LPS stimulated neutrophils is enhanced to the same extent by scuPA and purified uPA KD, but uPA lacking KD has no potentiating effect on LPS induced response. Neutrophils were incubated without (Control) or with LPS 10 ng/ml (LPS) and scuPA, purified KD, or uPA lacking the KD [(del)KD] (10 nM) for 4 hours. Cytokine levels were measured in the culture supernatants by ELISA. ***$p<0.001$ versus Control. ##$p<0.01$ and ###$p<0.001$ versus LPS alone.
Figure 5:
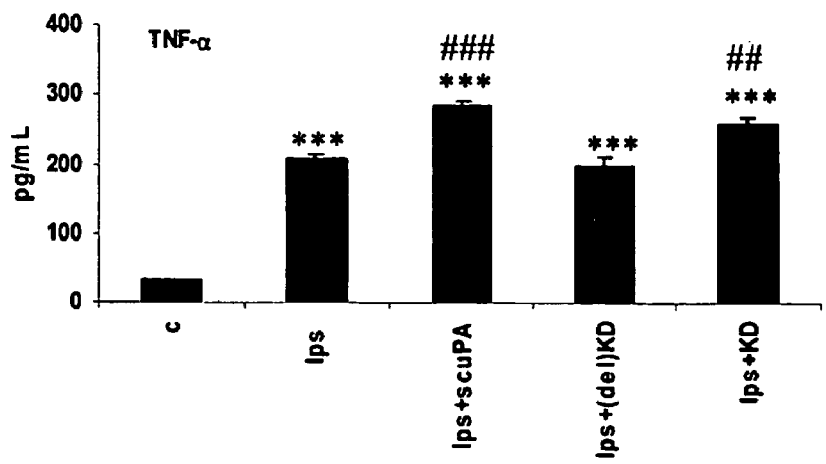
Figure 5:
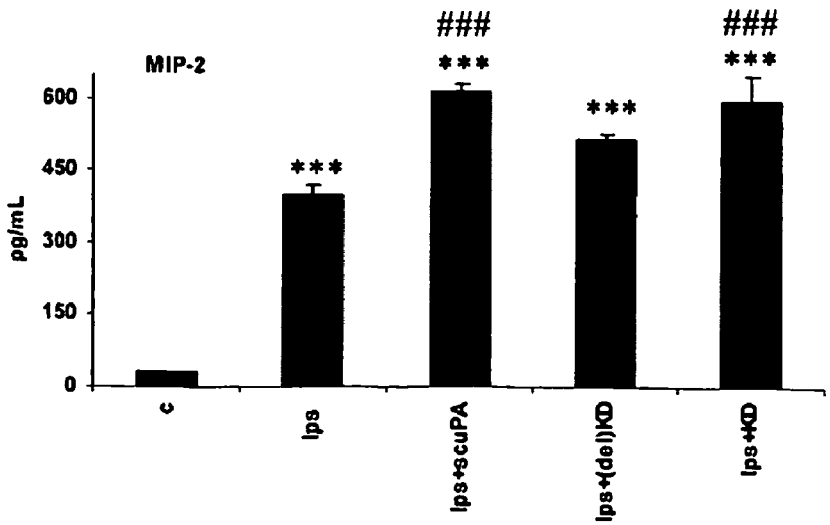

To further confirm that the KD of uPA potentiates LPS induced neutrophil responses, concentrations of proinflammatory cytokines secreted after stimulation of neutrophils with LPS and scuPA, scuPA lacking the KD, or purified KD, were examined. As shown in FIG. 5, the KD alone enhanced neutrophil production of IL-1β, TNF-α, and MIP-2 to the same extent as did intact scuPA. Conversely, secretion of cytokines by neutrophils coincubated with LPS and the uPA KD deletion mutant did not differ from that of neutrophils exposed to LPS alone.

Figure 6:
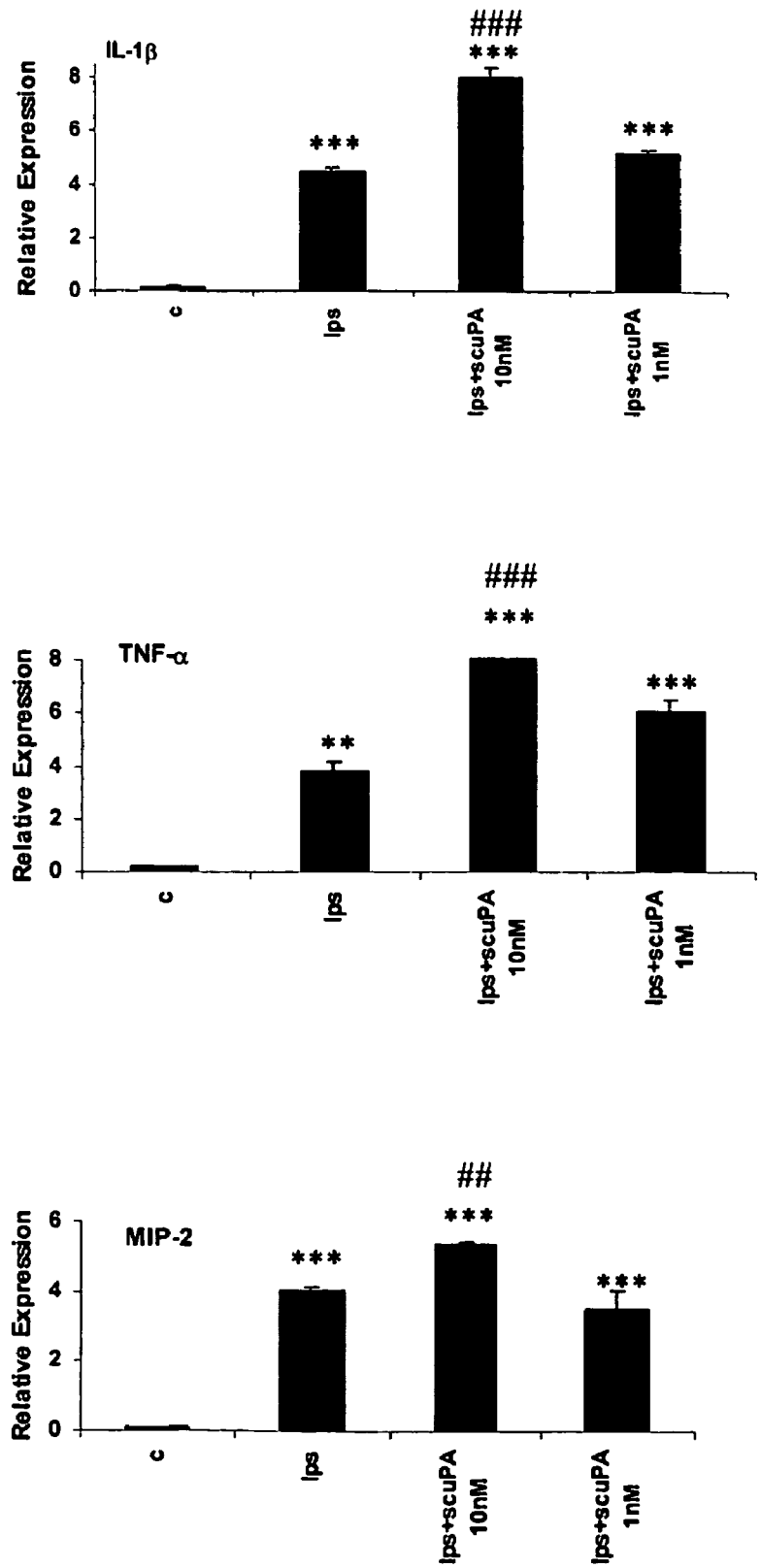
FIG. 6 indicates that uPAR is not required for uPA associated enhancement of LPS-induced cytokine expression in neutrophils. Neutrophils from transgenic mice lacking uPAR (uPAR −/−) were incubated with LPS 10 ng/ml and scuPA 1 nM or 10 nM for 4 hours. uPAR −/− neutrophils not exposed to LPS (Control) or cultured with LPS alone, but no uPA, (LPS) were also included. Cytokine mRNA levels were determined by quantitative RT-PCR normalized to GAPDH. $p<0.01$ and *$p<0.001$ versus Control. ##$p<0.001$ versus LPS alone.

Confirmation that uPA receptor (uPAR) is not required for uPA associated enhancement of neutrophil activation. The experiments shown in FIG. 1 demonstrated that the GFD of uPA was not necessary for potentiation of neutrophil responses. Because binding of uPA to uPAR involves the GFD, and human uPA does not bind to murine uPAR at the doses employed, those experiments suggested that uPAR was not required for the enhancement of neutrophil activation by uPA. To directly examine this question, we compared cytokine expression in neutrophils from transgenic uPAR −/− or control uPAR +/+ mice that were incubated with LPS and scuPA. The combination of scuPA and LPS enhanced expression of proinflammatory cytokines (IL-1β, TNF-α, and MIP-2) in uPAR −/− neutrophils to the same magnitude as that found in uPAR +/+ neutrophils (FIG. 6). Of note, the baseline responses of uPAR −/− and uPAR +/+ neutrophils in terms of cytokine expression to LPS alone were similar. These results confirm that uPAR is not required for these uPA-induced neutrophil responses.

Example 2

Figure 7:
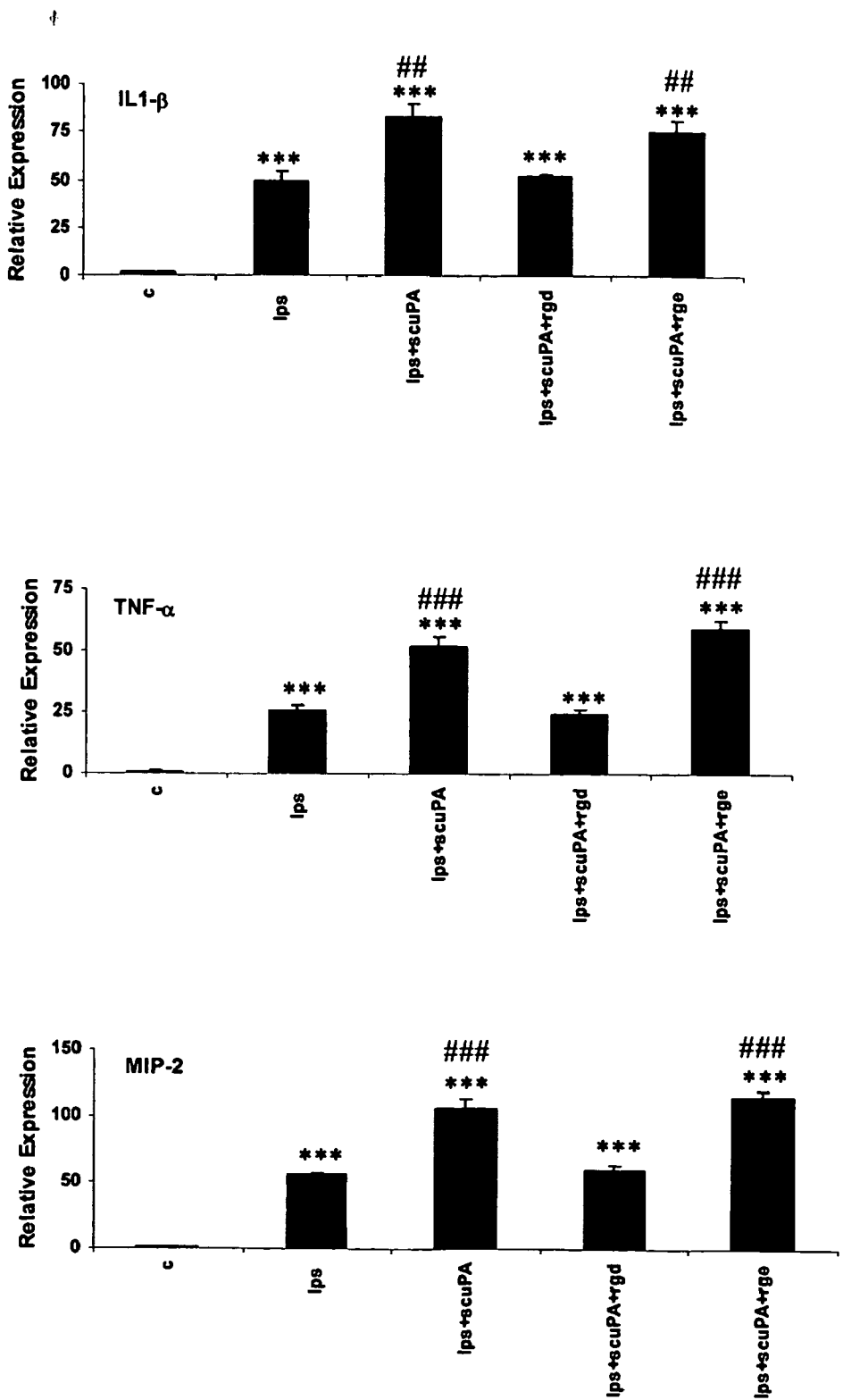
FIG. 7 indicates that integrins are involved in uPA associated enhancement of LPS-induced cytokine expression in neutrophils. Neutrophils were incubated with LPS 10 ng/ml and scuPA 10 nM plus either RGD or RGE peptide (50 µM) for 4 hours. Neutrophils not exposed to LPS (c) or cultured with LPS alone, but no scuPA, (LPS) were also included. Cytokine mRNA levels were determined by quantitative RT-PCR normalized to GAPDH. ***$p<0.001$ versus LPS alone and ###$p<0.001$ versus LPS+scuPA.

Identification of Integrins as Receptor for uPA KD uPA can interact with receptors other than uPAR, including integrins, which are expressed on neutrophils and are involved in neutrophil signaling. To investigate whether integrins participate in the potentiation of LPS induced neutrophil responses by uPA, we added RGD or RGE peptides to neutrophil cultures containing uPA and LPS. The RGD peptide blocks interactions with integrins, while the RGE peptide serves as a control. As shown in FIG. 7, addition of the RGD but not the RGE peptide blocked uPA-induced potentiation of neutrophil responses. The RGD peptide prevented the increased production of IL-1β, TNF-α, and MIP-2 produced by co-culture of LPS stimulated neutrophils with scuPA.

What is claimed is:

1. A method for treating a urokinase-type plasminogen activator (uPA)-mediated lung condition comprising, administering to a subject in need thereof a therapeutically effective amount of an antibody or antigen-binding region capable of binding the amino acid sequence of SEQ ID NO:2 of uPA to treat the lung condition in the subject.

2. The method of claim 1, wherein the uPA-mediated lung condition is selected from the group consisting of a uPA-mediated lung inflammation, uPA-mediated acute lung inflammation, acute lung injury, chronic lung inflammatory disorders, asthma, and chronic asthma.

3. The method of claim 1, wherein the uPA-mediated condition is a uPA-mediated lung inflammation condition.

4. The method of claim 3, wherein uPA-mediated lung inflammation condition is acute lung injury or asthma.

5. The method of claim 1, wherein the antibody or antigen-binding region is selected from the group consisting of a monoclonal antibody, a human antibody, a humanized antibody, a chimeric antibody, an antigen binding region of a human antibody, an scFv, a Fab, a F(ab')2, an Fv, an scFv-Fc fusion, a diabody, a linear antibody, a Fab', an IgG antibody, an antigen binding region of an IgG antibody and a single chain antibody.

6. A method for treating a urokinase-type plasminogen activator (uPA)-mediated lung inflammation condition comprising, administering to a subject in need thereof a therapeutically effective amount of an antibody or antigen-binding region capable of binding the amino acid sequence of SEQ ID NO:2 of uPA and treating uPA-mediated lung inflammation in the subject.

7. The method of claim 6, wherein the uPA-mediated lung inflammation condition is selected from the group consisting of, uPA-mediated acute lung inflammation, chronic inflammatory lung disorders, asthma, and chronic asthma.

8. The method of claim 6, wherein the uPA mediated lung inflammation condition is uPA-mediated acute lung inflammation or asthma.

9. The method of claim 6, wherein the antibody is a human or humanized antibody.

10. The method of claim 6, wherein the antibody or antigen-binding region blocks uPA from interacting with integrins.

* * * * *